United States Patent
Kozak et al.

(10) Patent No.: US 10,829,786 B2
(45) Date of Patent: Nov. 10, 2020

(54) AVIAN ONCOLYTIC VIRUS HAVING MODIFIED SEQUENCES AND USES THEREOF

(71) Applicant: ARV Pharma Inc., Calgary (CA)

(72) Inventors: Robert Kozak, London (CA); Byram Bridle, Guelph (CA); Eva Nagy, Puslinch (CA); Bradley Thompson, Calgary (CA)

(73) Assignee: ARV Pharma Inc., Calgary (CA)

( * ) Notice: Subject to any disclaimer, the term of this patent is extended or adjusted under 35 U.S.C. 154(b) by 119 days.

(21) Appl. No.: 16/220,732

(22) Filed: Dec. 14, 2018

(65) Prior Publication Data

US 2020/0190538 A1 Jun. 18, 2020

(51) Int. Cl.
*C12N 15/863* (2006.01)
*A61K 48/00* (2006.01)

(52) U.S. Cl.
CPC ...... *C12N 15/8633* (2013.01); *A61K 48/0058* (2013.01); *C12N 2710/24043* (2013.01)

(58) Field of Classification Search
None
See application file for complete search history.

(56) References Cited

FOREIGN PATENT DOCUMENTS

WO WO 2009158618 * 12/2009

OTHER PUBLICATIONS

Sequence alignment of SEQ ID No. 1 with Geneseq database accession No. AXV17358 by Dorsey et al in WO2009158618 (Dec. 2009).*
Kozak et al. (Viruses. 2017; 9 (90); doi:10.3390/v9040090).*
Kozak et al., "Replication and oncolytic activity of an orthoreovirus in human hepatocellular carcinoma cells", Viruses, 2017, 9(4), 90; doi:10.3390/v9040090.
Benavente, J.; Martinez-Costas, J., "Avian reovirus: structure and biology" Virus Res 2007, 123, 105-119.
Zamarin, D.; Palese, P., "Oncolytic Newcastle disease virus for cancer therapy: old challenges and new directions" Futur. Microbiol 2012, 7, 347-367.
Kim S.H., Samal, S.K., "Newcastle Disease Virus as a Vaccine Vector for Development of Human and Veterinary Vaccines", Viruses. Jul. 4, 2016;8(7). pii: E183. doi: 10.3390/v8070183.

* cited by examiner

*Primary Examiner* — Shanon A. Foley
(74) *Attorney, Agent, or Firm* — Gowling WLG (Canada) LLP

(57) ABSTRACT

The present disclosure relates to one or more modified avian-virus based agents, therapies, treatments, and methods of use of the modified avian-virus based agents and/or therapies and/or treatments for cancer. The disclosure also provides for methods of generating modified avian-virus based agents.

5 Claims, 2 Drawing Sheets

Specification includes a Sequence Listing.

AVIAN ONCOLYTIC VIRUS HAVING MODIFIED SEQUENCES AND USES THEREOF

SEQUENCE LISTING

This application contains a Sequence Listing electronically submitted via EFS-WEB to the United States Patent and Trademark Office as an ASCII text file entitled "A8141967US_ST25.txt" created on 2019-07-29 and having a size of 96,589 bytes. The information contained in the Sequence Listing is incorporated by reference herein.

TECHNICAL FIELD

The present disclosure generally relates to the creation and use of agents to treat and prevent cancer. In particular, the present disclosure relates to modified avian viral-agents, treatments and/or therapies that are based upon modified avian viral-agents, and methods of use of modified avian viral-agents for the treatment of cancer.

BACKGROUND

Oncolytic viruses are known to be useful in treating cancer. A number of viruses have been tested as virotherapy agents for the treatment of cancer. Oncolytic viruses derived from humans and non-human mammals have been tested but they demonstrate side effects such as fever and/or autoimmune responses.

Avian viruses, including avian reovirus and Newcastle's disease virus, have both been suggested for use as therapeutic agents for the treatment of cancers in humans.

SUMMARY

Some embodiments of the present disclosure relate to an oncolytic agent that comprises a modified avian-virus based agent that has an increased oncolytic activity as compared to a non-avian oncolytic-virus based agent.

Some embodiments of the present disclosure relate to a method of making an agent/target cell complex, the method comprises a step of administering a therapeutically effective amount of the agent to a subject. In some embodiments of the present disclosure the agent comprises a modified avian-virus based agent that has an increased oncolytic activity as compared to a non-avian, oncolytic-virus based agent and the target cell is a cancer cell.

Some embodiments of the present disclosure relate to a pharmaceutical composition that comprises an agent, a pharmaceutically acceptable carrier and/or an excipient. The agent comprises a modified avian-virus based agent that has an increased oncolytic activity as compared to a non-avian, oncolytic-virus based agent.

Some embodiments of the present disclosure relate to a method of treating cancer. The method comprises a step of administering to a subject a therapeutically effective amount of an agent that comprises a modified avian-virus based agent that has an increased oncolytic activity as compared to a non-avian, oncolytic-virus based agent.

Some embodiments of the present disclosure relate to a kit used for treatment of cancer or for delivery of an anti-cancer therapy to a subject. The kit comprises a unit dosage of an agent, a carrier for the unit dosage, and instructions for administering the unit dosage to the subject. Wherein in some embodiments of the present disclosure the agent comprises a modified avian-virus based agent that has an increased oncolytic activity as compared to a non-avian, oncolytic-virus based agent. The carrier may be a solid carrier, such as a pill or tablet, or a liquid. The instructions may describe how the solid carrier may be administered to a subject for an optimal effect. The instructions may also describe how the liquid carrier may be administered to a subject by various routes of administration.

Some embodiments of the present disclosure relate to a method of treating cancer. The method comprises a step of administering to a subject a therapeutically effective amount of an agent that comprises a modified avian-virus based agent that has an increased oncolytic activity as compared to a non-avian, oncolytic-virus based agent.

Without being bound by any particular theory, therapies or treatments that comprise the use of a modified avian-virus based agent as a part of an oncolytic virotherapy may provide increased lysing of cancer cells as compared to a non-avian oncolytic-virus based agent.

Other embodiments of the present disclosure relate to methods of making an avian virus that demonstrates superior oncolytic properties as compared to existing non-avian oncolytic viruses. Such methods generally include, but are not limited to, the steps of isolating the virus from avian samples in a line of cells that normally the virus does not normally infect, confirming the genus of the virus and that it is an avian virus, and confirming it has a unique nucleotide sequence by determining that the modified-virus has at least one nucleic acid with a different nucleotide sequence than a corresponding nucleic acid of the wildtype virus. Such methods also generally include, but are not limited to, selecting one or more improved avian viruses with respect to the virus's oncolytic ability. In other embodiments of the present disclosure, the modifying step includes culturing the avian virus in a human cancer cell line, and comparing its oncolytic activity and multiplicity of infection (MOI) to those of known and/or existing non-avian oncolytic viruses of the same group.

Avian viruses that are in the same group as non-avian viruses suggested for use as oncolytic viral agents include avian pox virus (group I, dsDNA), chicken parvovirus (group II, (+)ssDNA), avian reovirus (group III, dsRNA), infectious bursal disease virus (group III, dsRNA) duck hepatitis A virus (group IV, (+)ssRNA), and Newcastle's disease virus (group V, (−)ssRNA). Non avian viruses suggested for use as oncolytic viral agents include members of group I (herpes virus, poxvirus, vaccinia virus, and adenovirus), group II (parvovirus), group III (reovirus), group IV (Semliki forest virus, ECHO(7), Senecavirus, poliovirus, and Cocksacckie virus), and group V (Maraba virus, influenza virus, measles virus, and vesicular stomatitis virus (VSV)).

BRIEF DESCRIPTION OF THE DRAWINGS

These and other features of the present disclosure will become more apparent in the following detailed description in which reference is made to the appended drawings.

DETAILED DESCRIPTION

Definitions

Figure 1:
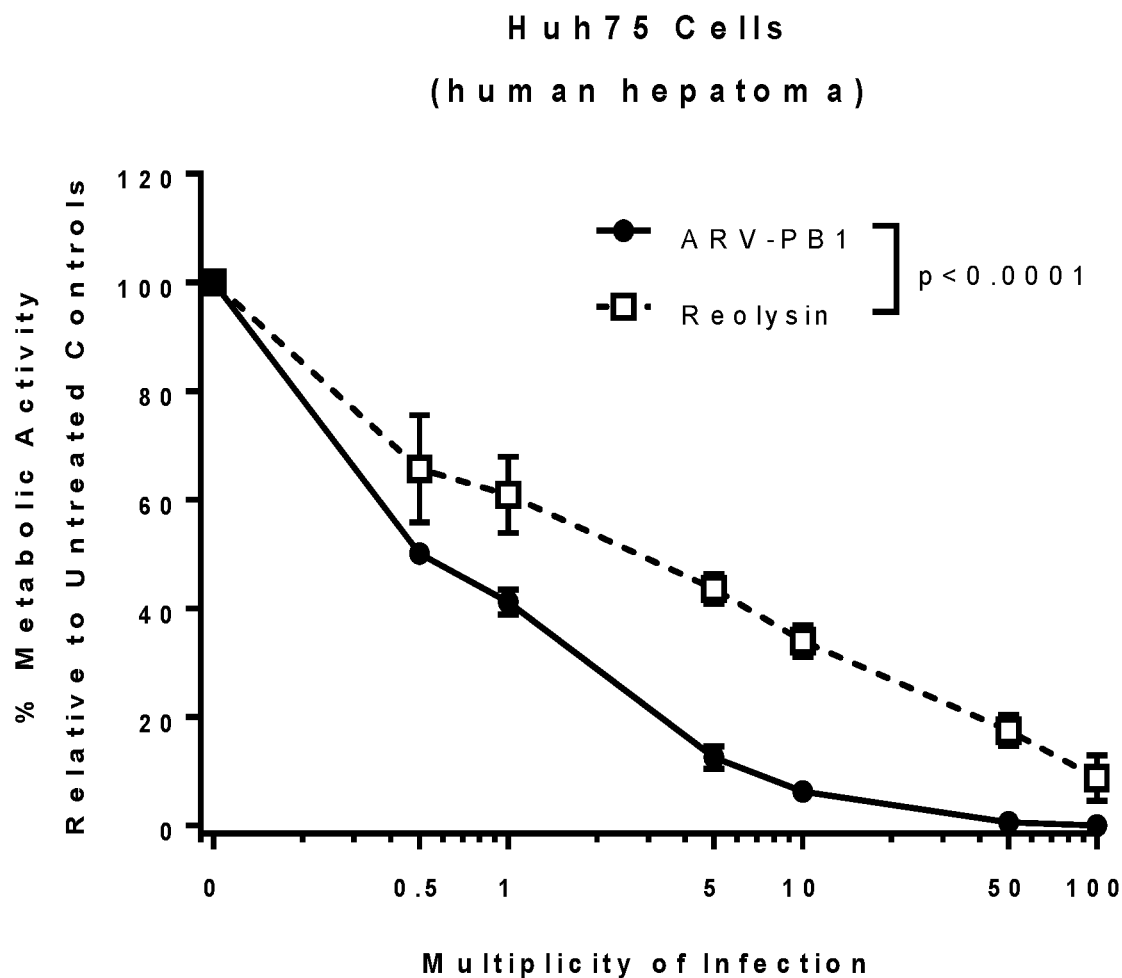
FIG. 1 is a line graph that depicts metabolic activity of a first population of human hepatoma cells following exposure to a modified avian reovirus of the present disclosure and an isolate of a human oncolytic reovirus.

Unless defined otherwise, all technical and scientific terms used herein have the meanings that would be commonly understood by one of skill in the art in the context of the present description. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

As used herein, the singular forms "a", "an", and "the" include plural references unless the context clearly dictates otherwise. For example, reference to "an agent" includes one or more agents and reference to "a subject" or "the subject" includes one or more subjects.

As used herein, the terms "about" or "approximately" refer to within about 25%, preferably within about 20%, preferably within about 15%, preferably within about 10%, preferably within about 5% of a given value or range. It is understood that such a variation is always included in any given value provided herein, whether or not it is specifically referred to.

As used herein, the term "agent" refers to a substance that, when administered to a subject, causes one or more chemical reactions and/or one or more physical reactions and/or or one or more physiological reactions and/or one or more immunological reactions in the subject.

As used herein, the term "cell" refers to a single cell as well as a plurality of cells or a population of the same cell type or different cell types. Administering an agent to a cell includes in vivo, in vitro and ex vivo administrations or combinations thereof.

As used herein, the term "complex" refers to an association, either direct or indirect, between one or more particles of an agent and one or more target cells. This association results in a change in the metabolism of the target cell. As used herein, the phrase "change in metabolism" refers to an increase or a decrease in the one or more target cells' production of deoxyribonucleic acid (DNA), ribonucleic acid (RNA), one or more proteins, or any post-translational modifications of one or more proteins.

As used herein, the term "excipient" refers to any substance, not itself an agent, which may be used as a component within a pharmaceutical composition or a medicament for administration of a therapeutically effective amount of the agent to a subject. Additionally, or alternatively, an excipient may alone, or in combination with further chemical components, improve the handling and/or storage properties and/or to permit or facilitate formation of a dose unit of the agent. Excipients include, but are not limited to, one or more of: a binder, a disintegrant, a diluent, a buffer, a taste enhancer, a solvent, a thickening agent, a gelling agent, a penetration enhancer, a solubilizing agent, a wetting agent, an antioxidant, a preservative, a surface active agent, a lubricant, an emollient, a substance that is added to mask or counteract a disagreeable odor, fragrances or taste, a substance added to improve appearance or texture of the composition and a substance used to form the pharmaceutical compositions or medicaments. Any such excipients can be used in any dosage forms according to the present disclosure. The foregoing classes of excipients are not meant to be exhaustive but are provided merely as illustrative of what a person of skill in the art would know and would also recognize that additional types and combinations of excipients may be used to achieve delivery of a therapeutically effective amount of the agent to a subject through one or more routes of administration.

As used herein, the terms "inhibit", "inhibiting", and "inhibition" refer to a decrease in activity, response, or other biological parameter of a biologic process, disease, disorder or symptom thereof. This can include but is not limited to the complete ablation of the activity, response, condition, or disease. This may also include, for example, a 10% reduction in the activity, response, condition, or disease as compared to the native or control level. Thus, the reduction can be a 10%, 20%, 30%, 40%, 50%, 60%, 70%, 80%, 90%; 100%, or any amount of reduction in between the specifically recited percentages, as compared to native or control levels.

As used herein, the term "subject" refers to any therapeutic target that receives the agent. The subject can be a vertebrate, for example, a mammal including a human. The term "subject" does not denote a particular age or sex. The term "subject" also refers to one or more cells of an organism, an in vitro culture of one or more tissue types, an in vitro culture of one or more cell types; ex vivo preparations; and a sample of biological materials such as tissue and/or biological fluids.

As used herein, the term "medicament" refers to a medicine and/or pharmaceutical composition that comprises the agent and that can promote recovery from a disease, disorder or symptom thereof and/or that can prevent a disease, disorder or symptom thereof and/or that can inhibit the progression of a disease, disorder, or symptom thereof.

As used herein, the terms "modify", "modified" and "modification" inclusive of all tenses, refers to a mutation of one or more nucleic acids of an avian virus to create a viral-agent that demonstrates an increased oncolytic activity as compared to a non-avian oncolytic virus.

As used herein, the term "patient" refers to a subject that is afflicted with cancer. The term "patient" includes human and veterinary subjects.

As used herein, the term "pharmaceutical composition" means any composition for administration of an agent to a subject in need of therapy or treatment of a disease, disorder or symptom thereof. Pharmaceutical compositions may include additives such as pharmaceutically acceptable carriers, pharmaceutically accepted salts, excipients and the like. Pharmaceutical compositions may also additionally include one or more further active-ingredients such as antimicrobial agents, anti-inflammatory agents, anaesthetics, analgesics, and the like.

As used herein, the term "pharmaceutically acceptable carrier" refers to an essentially chemically inert and non-toxic component within a pharmaceutical composition or medicament that does not inhibit the effectiveness and/or safety of the agent. Some examples of pharmaceutically acceptable carriers and their formulations are described in Remington (1995, The Science and Practice of Pharmacy (19th ed.) ed. A. R. Gennaro, Mack Publishing Company, Easton, Pa.), the disclosure of which is incorporated herein by reference. Typically, an appropriate amount of a pharmaceutically acceptable carrier is used in the formulation to render the formulation isotonic. Examples of suitable pharmaceutically acceptable carriers include, but are not limited to: saline solutions, glycerol solutions, ethanol, N-(1(2, 3-dioleyloxy)propyl)-N,N,N-trimethylammonium chloride (DOTMA), diolesylphosphotidylethanolamine (DOPE), and liposomes. Such pharmaceutical compositions contain a therapeutically effective amount of the agent, together with a suitable amount of one or more pharmaceutically acceptable carriers and/or excipients so as to provide a form suitable for proper administration to the subject. The formulation should suit the route of administration. For example, oral administration may require enteric coatings to protect the agent from degrading within portions of the subject's gastrointestinal tract. In another example, injectable routes of administration may be administered in a liposomal formulation to facilitate transport throughout a subject's vascular system and to facilitate delivery across cell membranes of targeted intracellular sites.

As used herein, the phrases "prevention of" and "preventing" refer to avoiding an onset or progression of a disease, disorder, or a symptom thereof.

As used herein, the terms "promote", "promotion", and "promoting" refer to an increase in an activity, response, condition, disease process, or other biological parameter. This can include but is not limited to the initiation of the activity, response, condition, or disease process. This may also include, for example, a 10% increase in the activity, response, condition, or disease as compared to the native or control level. Thus, the increase in an activity, response, condition, disease, or other biological parameter can be a 10%, 20%, 30%, 40%, 50%, 60%, 70%, 80%, 90%, 100%, or more, including any amount of increase in between the specifically recited percentages, as compared to native or control levels.

As used herein, the term "prophylactic administration" refers to the administration of any composition to a subject, in the absence of any symptom or indication of a disease or disorder, to prevent the occurrence of and/or the progression of the disease or disorder within the subject.

As used herein, the term "target cell" refers to one or more cells and/or cell types that are deleteriously affected, either directly or indirectly, by a disease or themselves are a product, either directly or indirectly, of a disease.

As used herein, the terms "treat", "treatment" and "treating" refer to obtaining a desired pharmacologic and/or physiologic effect. The effect may be prophylactic in terms of completely or partially preventing an occurrence of a disease, disorder or symptom thereof and/or the effect may be therapeutic in providing a partial or complete amelioration or inhibition of a disease, disorder, or symptom thereof Additionally, the term "treatment", refers to any treatment of a disease, disorder, or symptom thereof in a subject and includes: (a) preventing the disease from occurring in a subject which may be predisposed to the disease but has not yet been diagnosed as having it; (b) inhibiting the disease; and (c) ameliorating the disease.

As used herein, the term "therapeutically effective amount" refers to the amount of the agent used that is of sufficient quantity to ameliorate, treat and/or inhibit one or more of a disease, disorder or a symptom thereof. The "therapeutically effective amount" will vary depending on the agent used, the route of administration of the agent and the severity of the disease, disorder or symptom thereof. The subject's age, weight and genetic make-up may also influence the amount of the agent that will be a therapeutically effective amount.

As used herein, the terms "unit dosage form" and "unit dose" refer to a physically discrete unit that is suitable as a unitary dose for patients. Each unit contains a predetermined quantity of the agent and optionally, one or more suitable pharmaceutically acceptable carriers, one or more excipients, one or more further active-ingredients, or combinations thereof. The amount of agent within each unit is a therapeutically effective amount.

As used herein, the term "wildtype" refers to a naturally occurring organism or lifeform as found in nature. When used in reference to polynucleotides or polypeptides, "wildtype" refers to the native (unmodified) form of the polynucleotide or polypeptide as found within, or expressed by, the wildtype organism.

In one embodiment of the present disclosure, the pharmaceutical compositions disclosed herein comprise an agent as described herein in a total amount by weight of the composition of about 0.1% to about 95%. For example, the amount of the agent by weight of the pharmaceutical composition may be about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%>, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%. about 4.9%, about 5%, about 5.1%, about 5.2%, about 5.3%, about 5.4%., about 5.5%, about 5.6%, about 5.7%, about 5.8%, about 5.9%, about 6%, about 6.1%, about 6.2%, about 6.3%, about 6.4%, about 6.5%, about 6.6%, about 6.7%, about 6.8%, about 6.9%, about 7%, about 7.1%, about 7.2%, about 7.3%, about 7.4%, about 7.5%, about 7.6%, about 7.7%, about 7.8%, about 7.9%, about 8%, about 8.1%, about 8.2%, about 8.3%, about 8.4%, about 8.5%, about 8.6%, about 8.7%, about 8.8%, about 8.9%, about 9%, about 9.1%, about 9.2%, about 9.3%, about 9.4%, about 9.5%, about 9.6%, about 9.7%, about 9.8%, about 9.9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 85%, about 90% or about 95%.

Where a range of values is provided herein, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also, encompassed within the disclosure, subject to any specifically excluded limit in the stated range. Where the stated range includes one or both of the limits, ranges excluding either or both of those included limits are also included in the disclosure.

The present disclosure relates to one or more modified avian-virus based agents, therapies, treatments, and methods of use of the modified avian-virus based agents for treating and, optionally, preventing cancer. Some embodiments of the present disclosure relate to methods for making a complex between at least one particle of a modified avian-virus based agent and at least one target cell of a subject where the complex causes the modified avian-virus based agent to pass through the phospholipid bilayer of the target cell, copy itself therein and then interfere with one or more metabolic functions of the target cell. In some embodiments of the present disclosure, the modified avian-virus based agent may lyse the target cell. Embodiments of the present disclosure can be used as a therapy and/or a treatment for a patient with cancer.

In some embodiments of the present disclosure, the condition may be a cancer of one the following non-limiting examples: lung cancer, small cell lung cancer, non-small cell lung cancer, large cell lung cancer, renal cancer, colorectal cancer, bile duct cancer, penile cancer, melanoma cancer, non-melanoma skin cancer, cervical cancer, endometrial cancer, pancreatic cancer, breast cancer, oral cancer, brain cancer, glioma, astrocytoma, neuroblastoma, prostate cancer, adrenal cancer, anal cancer, thyroid cancer, bone cancer, osteosarcoma, soft tissue sarcoma, uterine cancer, fallopian tube cancer, spinal cancer, testicular cancer, head and neck cancer, ovarian cancer, vaginal cancer, vulvar cancer, stomach cancer, squamous cell cancer, sinus cancer, throat cancer, oral cancer, ocular cancer, liver cancer, intestinal cancer, gall bladder cancer, cancers of the lymph node, esophageal cancer or combinations thereof.

In some embodiments of the present disclosure, the agent can be administered to the subject by an intravenous route, an intramuscular route, an intraperitoneal route, an intrathecal route, an intravesical route, a topical route, an intranasal route, a transmucosal route, a pulmonary route, or combinations thereof.

In some embodiments of the present disclosure, the agent can be administered to the subject by pipetting a dose of the agent into an in vitro cell culture; perfusing or immersing an ex vivo cell or tissue preparation with a solution that comprises the agent; mixing a biological fluid sample with a solution or substrate that comprises the agent, or combinations thereof.

Some embodiments of the present disclosure relate to an agent that can be administered to a subject with the condition. When a therapeutically effective amount of the agent is administered to the subject, the agent is a modified avian-virus based agent that may enter into one or more cancer cells within the subject. The agent will then kill the cancer cells by replicating therein and then rupturing the integrity of the cancer cells' phospholipid membrane.

The embodiments of the present disclosure also relate to administering a therapeutically effective amount of the agent. The therapeutically effective amount of the agent will not substantially increase any deleterious conditions within the subject. For example, the therapeutically effective amount will not cause cytokinesis, hypercytokinemia, or any other uncontrolled, or partially controlled, upregulation of the subject's immune system. In some embodiments of the present disclosure, the therapeutically effective amount of the agent that is administered to a patient is between about 10 and about $1 \times 10^{16}$ TCID$_{50}$/kg (50% tissue culture infective dose per kilogram of the patient's body weight). In some embodiments of the present disclosure the therapeutically effective amount of the agent that is administered to the patient is about $1 \times 10^{13}$ TCID$_{50}$/kg. In some embodiments of the present disclosure, the therapeutically effective amount of the agent that is administered to a patient is measured in TPC/kg (total particle count of the agent per kilogram of the patient's body weight). In some embodiments the therapeutically effective amount of the agent is between about 10 and about $1 \times 10^{16}$ TCP/kg.

Some embodiments of the present disclosure relate to a method for making an agent/target cell complex within a subject. The method comprises a step of administering a therapeutically effective amount of the agent to the subject. The complex comprises at least one particle of an agent and one or more target cells. In some embodiments of the present disclosure, the complex is formed when at least one particle of the agent has passed through the phospholipid membrane of the target cell. In some embodiments of the present disclosure the agent is a modified avian-virus based agent that can replicate within the target cell to such an extent that the target cell lyses.

Some examples of a target cell that can form the agent/target cell complex include, but are not limited to: a lung cancer cell; a small cell lung cancer cell; a non-small cell lung cancer cell; a large cell lung cancer cell; a renal cancer cell; a colorectal cancer cell; a penile cancer cell; a bile duct cancer cell; a melanoma cancer cell; a non-melanoma skin cancer cell; a pancreatic cancer cell; a breast cancer cell; a cervical cancer cell; an endometrial cancer cell; a fallopian tube cancer cell; a throat cancer cell; an oral cancer cell; a prostate cancer cell; a brain cancer cell; a glioma cell; an astrocytoma cancer cell; a neuroblastoma cancer cell; an adrenal cancer cell; an anal cancer cell; a thyroid cancer cell; a bone cancer cell; an osteosarcoma sarcoma cell; a soft tissue sarcoma cell; a uterine cancer cell; a spinal cancer cell; a testicular cancer cell; a head and neck cancer cell; an ovarian cancer cell; a vaginal cancer cell; a vulvar cancer cell; a stomach cancer cell; a squamous cell cancer cell; a sinus cancer cell; a throat cancer cell; an ocular cancer cell; a liver cancer cell; an intestinal cancer cell; a lymph node cancer cell; a gall bladder cancer cell; an esophageal cancer cell; or combinations thereof.

Some embodiments of the present disclosure relate to a therapy that can be administered to a subject with cancer. The therapy comprises a step of administering to the subject a therapeutically effective amount of an agent that will form an agent/target cell complex and the agent will then lyse the target cell.

In some embodiments of the present disclosure, the agent is a modified viral-agent that is derived from an avian virus. The modified viral-agent has had at least one modification of a nucleic acid as compared to a wild type nucleic acid sequence of an avian virus. Modifications of a nucleic acid include, without limitation, single or multiple nucleotide transitions (purine to purine or pyrimidine to pyrimidine) or single or multiple transversions (purine to pyrimidine or vice versa) and single or multiple nucleotide-deletions or insertions. A modification in a the nucleotide sequence of a nucleic acid can result in one or more conservative or non-conservative amino acid substitutions within the encoded polypeptide, a shift in the reading frame of translation ("frame-shift") resulting in an entirely different polypeptide encoded from that point on, a premature stop codon resulting in a truncated polypeptide ("truncation"), or a modification in an avian reovirus nucleic acid that does not change the encoded polypeptide at all ("silent" or "nonsense"). In some embodiments of the present disclosure, the modification of the viral agent is caused by one or more known molecular biology techniques and the result is a modified avian-virus based agent that demonstrates increased oncolytic activity as compared to a non-avian oncolytic-virus based agent.

In some embodiments of the present disclosure, the modification may be caused, at least in part, by exposing a wildtype avian virus to one or more agents and/or an environment that increases a mutation rate by causing mutations in one or more nucleic acid nucleotide sequences. In some embodiments of the present disclosure, increases in the mutation rate may be caused by ionizing radiation (X-ray and gamma), non-ionizing radiation (ultraviolet radiation), one or more mutagenic chemical agents, and/or by culturing a wildtype avian virus on a foreign-cell type, where a foreign-cell type is one that the wildtype avian virus are not exposed to in nature.

In some embodiments of the present disclosure the agents and/or environments that increase the mutation rate may also be generated by one or more conventional methodologies taken from one or more scientific fields of: molecular biology, microbiology, biochemistry, and other recombinant DNA techniques.

While the examples below refer to specific viruses, cell types and methodologies, the person skilled in the art will appreciate that the examples are provided as illustrations rather than limitations of the scope of the present disclosure.

EXAMPLES

Example 1

An avian reovirus was identified from a chicken field sample by visualization of its cytopathic effect in chicken hepatocellular carcinoma cells (CH-SAH cells). The avian reovirus was then isolated by plaque purification, and subsequently underwent a second round of plaque purification, with the largest plaques being selected in both rounds. After this, the avian oncolytic virus was passaged twice on CH-SAH cells in order to make the working stock of one example of a modified viral-agent, referred to herein as ARV-PB1.

Without being bound by any particular theory, the exposure of the wildtype avian reovirus to the CH-SAH cells constituted an environment that increased the mutation rate resulting in one or more mutations in the wildtype avian reovirus to generate the modified viral-agent, ARV-PB1. As will be appreciated by one skilled in the art, the CH-SAH cells are not the type of cells that the chicken field sample is typically exposed to in nature and this may have resulted in the increase in the mutation rate of the wildtype avian reovirus.

Example 2

Example 2 demonstrates the differences in nucleotide sequences between two reference strains of the avian reovirus and the ARV-PB1 modified viral agent of Example 1. The sequence of the 10 genome segments was compared to vaccine strain S1133 (Genbank KF741756-KF741765) and strain 1733 (Genbank KF741706-KF741715) using the commercially available GENEIOUS® software, version 9.1.8 (GENEIOUS is a registered trademark of Biomatters Ltd.). The inventors used a method similar to that described by Tang, Y. et al. ((2016) Detection and characterization of two co-infection variant strains of avian orthoreovirus (ARV) in young layer chickens using next-generation sequencing (NGS). Sci Rep, 6, 24519).

Ten different segments of the avian reovirus genome were compared between the reference vaccine strains (S1133 and 1733) and ARV-PB1. The ten segments are: L1, L2, L3, M1, M2, M3, S1, S2, S3 and S4. The sequence identity at the nucleotide level between vaccine strain S1133 and strain 1733 ranges from 99.21-99.92%. The ARV-PB1 gene segments have a sequence identity ranging from 82.30 to 92.30% at the nucleotide level with vaccine strain S1133. ARV-PB1 gene segments have a sequence identity ranging from 82.21 to 92.30% at the nucleotide level with strain 1733. Table 1 below summarizes nucleotide homology percentages.

TABLE 1

Percent nucleotide homology based upon sequencing ten genome segments of avian reovirus strains S1133, and 1733 as compared with the modified viral-agent ARV-PB1.

| ARV-PB1 | % Nucleotide Homology S1133 | 1733 |
|---|---|---|
| L1 | 89.24 | 89.27 |
| L2 | 90.08 | 90.18 |
| L3 | 89.97 | 90.10 |
| M1 | 90.89 | 90.98 |
| M2 | 84.99 | 85.09 |
| M3 | 90.63 | 90.48 |
| S1 | 82.64 | 82.45 |
| S2 | 92.30 | 92.30 |
| S3 | 87.11 | 87.11 |
| S4 | 82.30 | 82.21 |

In addition to these differences of nucleotide sequence matching, it is also noted that the modified viral-agent, ARV-PB1 did not demonstrate 100% nucleotide sequence matching with any known virus when a basic local alignments search tool (BLAST) search was conducted against a database of known viruses.

Example 3

After the ARV-PB1 genome was sequenced, the relatedness of ARV-PB1s to known viruses was assessed using BLAST. The genus that was the closest match to the ARV-PB1 was Orthoreovirus. That and the taxonomic criteria of the Ninth Report of the International Committee on Taxonomy of Viruses were used to determine the closest taxonomy of ARV-PB1:

Family: *Reoviridae*, Subfamily: *Spinaviridae*, Genus: *Orthoreovirus*, Species: *Avian Orthoreovirus*.

Example 4

Following the genome sequencing and taxonomic characterization of the modified viral-agent ARV-PB1, the oncolytic activity of ARV-PB1 was compared with another group III non-avian virus, a clinically tested, human oncolytic reovirus (REOLYSIN®). Reolysin is a modified human reovirus, type 3 Dearing, which is also referred to as pelareorep.

Figure 2:
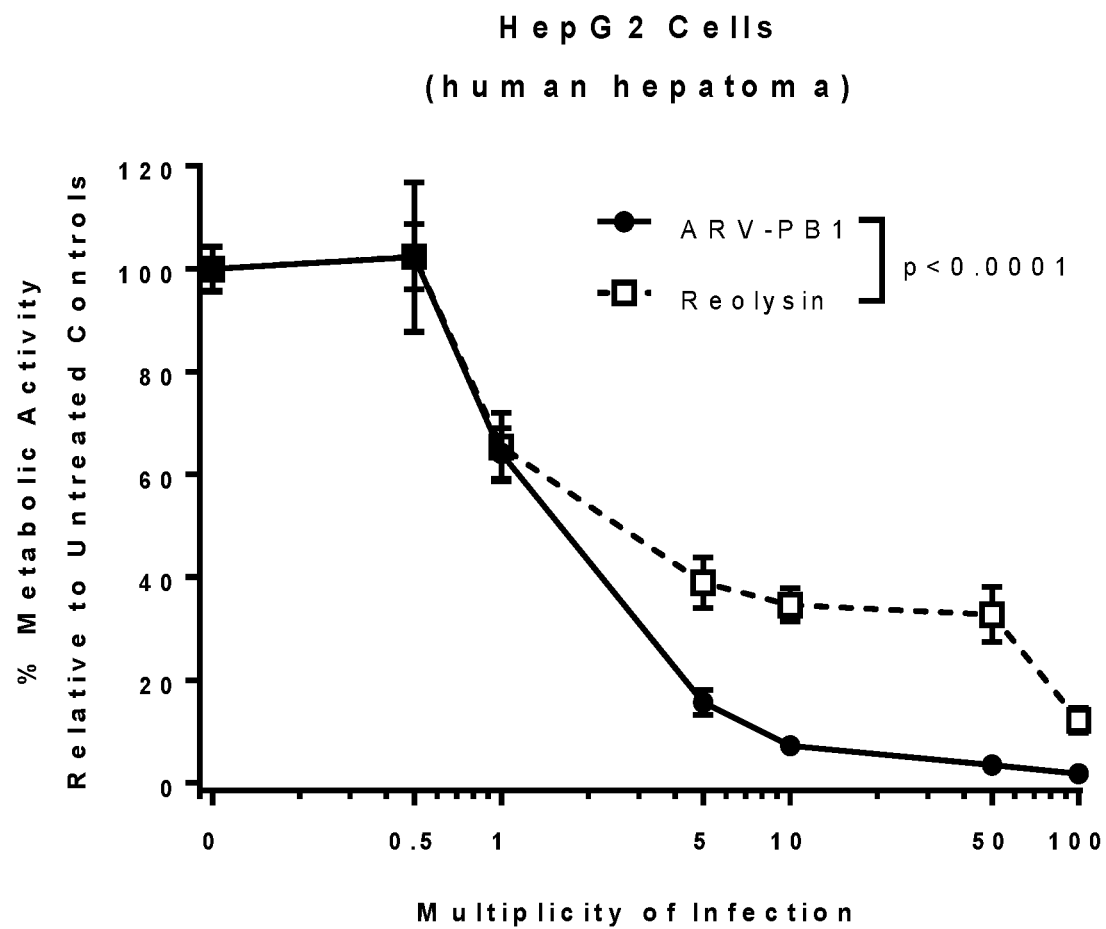
FIG. 2 is a line graph that depicts metabolic activity of a second population of human hepatoma cells following exposure to a modified avian reovirus of the present disclosure and an isolate of a human oncolytic reovirus.

Using a resazurin dye-based metabolic assay to determine cell viability, the oncolytic activity of ARV-PB1 was compared with Reolysin in two human hepatoma cell lines, Huh75 cells and HepG2 cells. Resazurin is converted to a highly fluorescent metabolite (resarufin) in metabolically active (live) cells. The fluorescence was then quantified using a plate reader. The ARV-PB1 and Reolysin were added at various multiplicity of infection (MOI). The cells' metabolic activity was assessed 96 hours later with a lower metabolic activity reflecting a higher oncolytic activity and vice versa. FIG. 1 shows the experimental data observed in the Huh75 cells and FIG. 2 shows the experimental data observed in the HepG2 cells. Each line graph represents pooled data from two experimental replicates with triplicate technical replicates per experiment. Shown are means and standard errors. Data were analyzed by two-way ANOVA, with ARV-PB1 causing statistically significant lower metabolic activity in the two cell types as compared to the Reolysin.

Example 5

Table 2 below provides the nucleotide sequence listings for the modified viral-agent ARV-PB1 as follows: SEQ NO. 1—segment L1; SEQ NO. 2—segment L2; SEQ NO.

3—segment L3; SEQ NO. 4—segment M1; SEQ NO. 5—segment M2; SEQ NO. 6—segment M3; SEQ NO. 7—segment S1; SEQ NO. 8—segment S2; SEQ NO. 9—segment S3; SEQ NO. 10—segment S4. Table 2 below also provides the nucleotide sequences listings for the same segments of the avian orthoreovirus strain S1133 (SEQ NO. 11 through SEQ NO. 20) and the avian orthoreovirus strain 1733 (SEQ NO. 21 through SEQ NO. 30).

TABLE 2

Nucleotide Sequence Listings

| SEQ NO. | Sequence Description | Nucleotide Sequence |
|---|---|---|
| 1 | modified viral-agent segment 11 | gcttttctccgaacgccgaaatgagttcgcgcaaagtggctagacgtcgtcataaggat gctactgaatctaaagacactaagaacactactaagtctaagccttcttccgctgacgtt aaagaatctgtagacaacgccacagacaaaaaagtgaccgtcccaacgccagataatcca gctgcctctactccctcctctactgatggggcttcacaaacctcagtcgctaagcagacg aatgataatgataactcagttaaggaatcggctcccaaacctactgtgtctagtgatggg aaagatgggatgcacagtgcggtgaagtcgcaagacgccaaagcgaccacagctgtagat aataataaggataggaacgtagtatttggtggtgcgggttctggtgataagaatgctatt acgaagactgggtctgttgacaatgatggaggtgttaaggttgttccagctaaagacgct acgatatcttcagctaaggctatgatggagcaaaaacagcttgtagctggccttccgaag caaccgaagtccgctaatcatttgtgtactgtctgcatggcccagttcgcgtcatctgac gctcttgctattcaccagactacgcattctattggttccaatgctgctctgacaagcttt tcgatttctactgctgtcgaagaattcattcagtcatgggctactgccacgtctacagcc aacactaagacggctttgactgtgtctgacgttgactcactgatgatgactgaagggata cgcctcataacttgggattccgggttatgtacgtctttcgaacttgtcccgattgtccat tcaaatactgttcaagatgttatttcgtattcatggtttacgtcaagctataacatcact accccctttccacaggcgactgtcgtgcgaatcgttttacgtaccaactgggctgctaag ttggattcaccctcgtcatcgcgggaatgtgatcttcgtcttgcacctcctacggagagt aacgctagatcattctcgatgctactcaacacgggtgcgactccagaaggcactttcaac ccaaacacccttcgtatgaatgtgctgcagatgtgtcttcagtatgtgctgtctaactta cacttaaaccgtagtactcaatttaccatggatttgactgccgaggctcctaatctttcc gcgtctcaactccgtattgttccagaggataaggagggtaaatggttccctgtcatgtat ccatcccgagtgaacatcccccttgttcaataagactgctgatttcgtcaatcagtgcatt cgtgataggataggccgatatgatcgtgctcagactttcgctggcgcaccttctgaatgg gctgatatgtgggagacagcggactcgctaactcttccgtccgtgaaatgtggatgtcg cgtatttctcagatgaatatcactcccgctgacattgctgacgctatctccagatgttca cagtccttgctcactgtggctgcacctacggctccctctgtggctcgcttgttgccttgg cgtgttagttctgatgagaggcagctcctccaattgttaatgtacctaaatgttggaccc agtgccgactacgttcagccgattctgtctgcgtttgctcggactctgtctcgtgtgtca ccactgcgcattaatcccaccctgatcgctaacgctatgtcgacgattgtcgagagcact actaacacccagagtcctgccgcggctatcttgtcaaagcttaaacctgtggcctctgat ttttccgacttcaggttggcgtgtgccgcctggctatataacggttgcgttcagacatac ctatctgaggattcatatccaagcagtggtgggtctgtcactagcatcgacacgttggtt gatatgttcgtgtgtctattggcgttacctttagtcactgatcctaatgctccgtgccaa gcctttatggttgttgctaacgccatggttggctacgagaatctgcctatggacgatcct aattttactcagcagaggttggctgcagcgttcaacaatcctaccacctggcctcagtgc ttcctccacctcaaaatattgatcgtcgccagtgtcccatcctctcttggtgggctcaa caaatccaccgtaattggcctacaccatctcagattacttacggtgcacctgatatcatt ggatccgccaacctgttcactcccctgatgtgctgctgcttccattacaacacaggcc atacgtattaccaatcccactttgaacttcgataatgagttgacgacctggcgtaacacc gtggtcgatttagtcttacgcatcatcgacagtggtcggtaccagcctaattggaatcag tccattcgcgcatccatgcgaaacgcgatgacgaatttcaggattatcaagtcttacact cctgcctacatagcggaactgctgcccgttgaattggcggctatcgcccccaactttaccc ttccagccttttccaggtaccgtttgctcgtttggatcgtgacgctatcgtcactcacgtc aatgtatctcggcaagctcccaacaatcttgctcaacctgcgttgaacatgtctatgacg taccagcgcacgggagttccaatctctctcagcgcccgtcccttagcggtcgctcttctg tcaggccagtaccccactgatcctcctctccagaccaacgtttggtacgtgaacactctc acacctctgtattccaatgatggtctcttaacaacgtgcaacatgcgatggtcgcctct gaagcttacgccactttgatcactatgctggctcagtgtactgacatgcagtaccccgtg gatcgcccctctgaactggctgcgtcagattaatttggctgctaatgaggcgacgattttt ggtcgctcgattaattcactttccaaactgcctttgacctctcgccttccactgtgttg cttcaacctttcttagaatctgatccacgtgcaacgcaactagccatttcttacgttcgc tataatggagacagtgagaccttcgtaccgacagtacggccatctatgatctcagaagcg acattgctcgttgaacgcactcttcgcacgaatacaatcttttcggtttatgtcgtggt gatatcattctggggcaacacatgactcctactgcgttcaatcccttagctcctcctcct tctgtcatttttaacaggggtgacgctgatgtttatgaattcggatctcgtagcttcgct aacttcggtatgaatggagaggagattttggttatggacgcgaacggtgtgcgtcgtcca ctacttggccggtgggttatgccgctccagcttttgatggtgaatattggtgtatttccc aagctgctgttggatcgtatcttgaaaggacgtctatatatcagacttgaagttggcgcg tatccatacacggtgcagtactaccagggacgtgagttcactgacggtttcacattgctt gagcaatggatgtccaaggtgtcacccatgggtatccctcctgttccttttctcatgcca cagtccgagggacacaatatcacttcaggcatggtcactcattatatctggtccactgag tacaatgatgggtcactctttgccacgaacactgacctgccggttactgtatttgggcct gaccgcaccattcctatcgagcgctatcgtgcactcgttgacccaggcgccctccctgcc actaaccaactgccgcacactatcgacctttattgctcactaagacgctactatctggag acacctcccattactgcctactcacttatgcgatggactcccgcgctgaaccat tagagcggcgaggctagacgcgagctgatcgcgtcgactctcgttggagattattcatc |
| 2 | modified viral-agent segment 12 | gcttttcctccaccatgcatgtcaacgggtttgatgatgctactctctcctacgcacaat ccatctcgggggttatcccaatgacaaataagctatttgagcaagcatctgcatcgatac gtgccctacctcgctcacatgtttataccttattagataatgtaaattttctctgtttcat |

TABLE 2-continued

Nucleotide Sequence Listings

| SEQ NO. | Sequence Description | Nucleotide Sequence |
|---|---|---|
|  |  | gcgtgatcccaaatcgtatcttccatcattccgaccactctgagtattttacatcgacg<br>cggttaatagggttagacggaaacaagttattgatgctgacgatgtattcgtgccaaatt<br>gcaacctgcagggtcttgtcactccaatgaaagattgccaaactatggtcagttgtctg<br>agactatttcgtcgaacgctcgggacggcttgccatccgcacgcgtagcagctacatttt<br>ataacatctcggtatctcaggctcgtcaggttaaagccccacttgaaacattttgttac<br>ctttgttactaactgaaacctgcccgttatcggatgatccctgcggacttgacacctcag<br>cttctcccccgatccatgctaatctagcactatgggtgttacgtgaaattagtcgaacta<br>tttgtggatcttcaaaagaccgttcgccctggttattactcgattcaggggttgcatggt<br>tcatgtctccactgatgtcatcagctattccacctctcatggctgacttaactaatctgg<br>caatctataaacagatttgttcagtgcccgacgagcttcactctcttgcagttcaagtag<br>ttttgcaggctgcagcgtcacaatcatatggtcattacatattgcaaacgaagtcgatat<br>ttccacagaatacgttacataacatgtttcgtacactcactgatggcatcgttccggtca<br>tagagtggttggaaccgcgttccaactatcgcttcatgcttcaaggtgcgcgtaaagtga<br>cttcagatgacgcgaatcaagctccggataatacagaagccgccgagcaacttggccgaa<br>aaatgggtgcttggatgttgtacgctctttacggaagatgtctgcgtccatcacggtgc<br>attcacatgatgccatgactttcgtgcgtgacgctatgtcttgtactagcggcatctta<br>ttacacgtcaaccgactgagactgttttgaaagagtacactcaagctcctaccattgaag<br>ttcccattccgcaatccgattggtcaccacctattggatcttacgatatctctcggacg<br>cctgctccctccctgctgtatatttggctagagcttggcgaagagccgcttctgctgtag<br>tagataacccacatacctgggaccccttatatcaagctatcctccgctctcagtatgtga<br>cgtcacgtggtgggtctgagtgctgcattaagagatgctttgaaggctgcagaagttgaac<br>ttcctcagtatcctgggggttagtgtcaaggtagcaaccaagatttatcaagcggctcaga<br>ctgcggacgtgccttttgacaagttgtctcgagctgttctggctcctttgtcgatgggat<br>tgcgtaatcaggttcaacgacgtcccaggaccatcatgcctatgaatgtcgttcaacagc<br>agatttcagcggctcacactctatctgctgactacatcaattatcatatgaacttatcga<br>caacatcgggtagcgcggttattgaaaaggtggttccgttaggtatgtacgcgtcttgcc<br>ctcctgctcaagcagttaacattgacatcaaggcctgtgatgcatctatcacatatcagt<br>attttctttctgttatcgtcggtgctatacatgaaggtgcagcgggccgtcgtgtttcat<br>cttcattcatgggagttccaccaagtgtgttatctgttgttgatgctagcggcgtgacgt<br>cctcagtgcctatttctggtttccaagttatgtgtcagtggttagctaagctttaccagc<br>gaggttttgagtaccaagtgacggacacgttctccccaggtaacattttacgcaccata<br>ctactactttcccctccggctcgacagcgacgtctacagagcatactgcgaataatagta<br>cgatgatggatggatttctgcgtgcttggattccttcttccggtgcgtctgatgtactga<br>agaagttctgtaaatccatttcaatacaacggaattacgtttgtcagggtgacgacgggt<br>taatgattgttgatgggctatcatcaggtaaattgtcaggcgagataatcgatgaattcg<br>ttaaagagttgagagcttatggcaaatcatttgggtggaattatgacatagagtttaccg<br>gaaacgctgaatacctcaagttgtatttcttaaacggttgccgtatacccaacgtttccc<br>ggcatccgatttgtggcaaagagcgcgcttcggggggacaagttagaaatgtggccatca<br>ctattgacatcttcaatggcatatttgtgaacggtgtgcatgatggcttaccatggcgca<br>ggtggttacgttattgttgggcccttgcacttatgtattctgggaaaaccgtacgtcacg<br>acgactctgatgtgttgatacagtaccctatgtggtcctttgtgtattgggtttgcctc<br>ccgtgagcgcgttcggtctgatccatggatctttctccctacatgcccactggtgatc<br>atggtttctattcaatgttaacttagtgcgccctctggtcactaacttatcccgtctt<br>cagacactttgggattatttggtcaatgtgatcacaacgttctgttcaacttcgagctag<br>tctaccagggctattacatggctcaatgcccacgacaaccctctcgttcgaatcgtaggg<br>atgatcctgattctgtacagcgcttttgttaaggcttagagtcttatctttatatctccc<br>ctgagctaaaatcacgagtcgacttggtcatgaccgatggcagaagttagttgggtata<br>cggagaaatctccccgtcgcttgacgatgtagccttcaaatggttccgtagcgcacaag<br>aagctgaccttccaacgcctctgaaattcaaagcatggatctgaccttgctgtctgcca<br>gacgtcgaacgtatcagggtttctccaaattgttaaacatctacttgagggtgacttggg<br>acttatccgatcctgttgcgcacgctgtcgatcctcgtgtcccctttatgcgctggtgttt<br>ctccatcgaatagcgagccatttctcaaattgtactctgttggcccaatgatgcaatcta<br>cgcgtaaatactttagtaatacattattcatccatcgaactgtgtcgggtcttgacgttg<br>atgttgttgaccgtgcgttgcttaggctacgtgctcttaacgcgcctgatgatgtggttg<br>tagcccaacttttgatggtaggtttgtccgaagctgaagccgcaacgttagcagcgaaaa<br>tccggacgatggatattaatgccgtgcaattggccagagtcgtcaatctgtccattcctg<br>attcgtggatgaccatggacttcgaccgcttaatacgagatatcgtgtccatcactcctc<br>taaccgtccgatccctaaccaccgatctaccttctggtgtaccatgggctcgcgcgatat<br>tgcagttcctaggtgcgggtgttgcgatgacagctgttggaccccctgcgtcgtccttact<br>tgcactcagttgccgggggcatgtcctcattcattaagcaattccgccggtggatgcgtg<br>ccgaaacgaggtagcgtccgtgcctggcatggctcgaggaattactcatc |
| 3 | modified viral-agent<br>segment 13 | gcttttccacccatggctcagattcgaggccttcggttgtctacgacactctcagctccg<br>ccaccacgaaagattgtaacttctcatacgtatgatgaactaatctctgctttaaagttg<br>acaaccaaaccttggcgccctttgacatcacgcggagatgactcgattacagcagtacag<br>cttctctttccccttaatggttatattgagcccatgttcatgttggagaaggacatgact<br>cacgacgctttcgagtcttggattacgccccttctgtctgctctggctgaccagttgctc<br>agacgctacccctattgctgcttatcatggacaattaattaaccccttgttagccaatgct<br>gttgttgccgctttcttatcgaatgtaccctatgcacatgcgctggaccacctctttctg<br>gttcgtggaaacgttgaggatattatggatgcgggaattacaattcagaatcatttatgg<br>tttgatcgtggcgtatcgtaactccggctgggcagaagtttgttcagttgactggttac<br>aatttctcatccaacgatccgtgtttattctctaagcaattacgctgctatggtcttgtt<br>tactattttctcaacatgtctgattgtctgacgtattgttggcgtcatctatctaactca<br>actcctctgatacattttgatcgtccttcaacgggattcattgtttggtaccctccgaa<br>tccacgacacctatcgcgggttcgctacctgtgtcagccctcagctctattctgttggag<br>tcttgccttcagcagtctttactcaatgctcttactcctacaggctcgccagtcattagg |

TABLE 2-continued

Nucleotide Sequence Listings

| SEQ NO. | Sequence Description | Nucleotide Sequence |
|---|---|---|
| | | caggtggaggtgctactacctctatcgtcaccattcttcgaacgtctgaatactctagaa<br>tattctcttttttgctctttcgaacgctctgattaacggctaccagttagtagatttacgt<br>tccggacatccagattgcgccaccgtcgccgctatttttaactaggttaactgatttctcg<br>aaaggtatcactgttattcaaccacgtcctgctcttttcactatcaataatgatagtcct<br>ctgacgtatagtggagagaacgccaatttcatccagcgcttggcgtccatgtctggaaga<br>tctattggcccagtcgttattgggaaatctgttaatcatgccgtcggttggatgccccag<br>tttgatcccgctacgtcatacaatcctgacttatcattggattcgctttcacgagccacg<br>acgctgccacttcgcgctaagtactctactttctggtctggccccgcactcttttcctttt<br>gcttcgtgtgacaggcacaatggcgtgtatgacattcaattcatggctcagtttcctcct<br>acgtattttaatgatgatgacaccttttctcggtcgaggttctcttcctaccgtgctgtt<br>aaagatcgatcgctgttaaaagataccgccaacttgatgtatatctcaaacttatcaagt<br>tcgcatgaccaccgtcttgtccctgattctaagaccatgatctacgtgggatcgtctggt<br>acgcatgcagataaccaaccttccatcattaaacctcttctagctgggtctcttccaggt<br>gttttccgtccccccgtccgtaaagcagatcggttgggaggttactaacgggactatttgt<br>gacattgaactgcctttggctaccggtaccttcttttttcgtgtacagtgacgtggatcgg<br>gttcactcgggcgactccgacctacacgcttcctctcgtcgcttttgctctcatttggac<br>atgttaatgaaattgacgtttaggggggttctttggtcgtcaagtgcaacttttccaact<br>aacttggtttggcgtcacatcttttcgaccgtttctccctatttctcatctattcatcag<br>atgaaccctcttgtgtcaaataatttggaactgtatttattatttgcggagcgtttgcct<br>gtccctgatgttgcttttcctccgtcggcggactttgtcttttcgggcgatcccatttg<br>caacgctatcgagtattgcgtgactcattctccaacgtgccctccatggcctccactctt<br>accttggatgattcattgacggtatctattctgaattttgtcgatgttacttccctatcc<br>tccatcgaggatcaaagagctttatccgctttctcggtccttacctctttggggtctcag<br>aagttgtcgcttcatccctactttgatagttatcgcacgcatctcaccggaataatcact<br>ccacattctcgcaacattttagataggttagcatacgttccgcgtgtctttccttcaacg<br>attgacgttcaacatcgtgttatggcttcctcagatccagagatttttggctttcgctcc<br>aactcttggactcaattgtcttttttctatgacgctacgttaactgcaacgattttact<br>gatgtgaagcattggttggatttgggaactgggcccgaagcacgcccgttgtcctttctg<br>ccgactgatctccctatcaccttgtgcgatactcgaccttttcgttttcccgtccggctgt<br>tgggctacttttcactgatttcttaagttacgattaccttgttacgaatgtcgtcttatcg<br>actggtgccgacgttgtgtcctgtattctctccctaggggcagcttgtgctgacgctaac<br>atgactctacatgagggcgcgcggcagctaatctcccagtgcgtagatgccagtgttaag<br>acgctgtttctacagcttaattgtccccttccatcagcgggtgacgtgtctcgagagatt<br>cttgaggtggttcagactaactcaacgtacatatttcatacctttgggtcgtgtcgagccg<br>tttattccatattccgccctcttagaaatagtcgaggatttgtgccctggtatcgtcgtt<br>gagattaaaacgatggattcttctctttcctggcttgactacgctgttcaatctaatgca<br>tcggtgacatcagatgacattgtcctggcgatgcggttgtctcacttctgtcctctttt<br>gtgtttcatttgatcgtcagtctgctcaattcccagatgacgcgcgtgttggtgctcct<br>ttcaccgtcacactgctagattatgaagcacactcgatcatatgaggtgactttagataat<br>gttactattgccactattaccgcgggcgctttggtcggattttcatctggtgtgaccgtc<br>acctcgtccaacaaccagctggttctgactattgaccctgcgagtccaggaattctgtcc<br>gtcatccaagtcctccccgcccgtatctcactaggcagttgcgtgataagagctcccgac<br>ccatccctctctctgatctttcctgctacgttagatacttccttatcaggaaccgatctg<br>gagttgtttttgtctgactggtatgacgttgctctattctatgtcgacgaagcgcactct<br>cgactgctgccagtatccgacaccaagtatgagatttatcgtaaggatcaaacgccaaat<br>agtcgaataatcaactatatctcgatcgttctgacgtgttctttaaattggtgctgtgt<br>gacgtttcgccatctgaataggtcgtttcatctaccgtgagttaccagagctgagttct<br>ccggtatggcctgacgacgtgcgtactttcttatccataccattttgaatccctatggtg<br>attgtatcgccggacggaccgtaaattatgacggtgtcaatttcacccctccaacttca<br>tggcttacgttgacggcagcacttgcgttgtagacggccgtccttcgttttatgtgccc<br>cctggccgatatggtctggtgagagtctaaacgaccgcgggcctccagtagaagggtgtt<br>attcatc |
| 4 | modified viral-agent segment M1 | gctttttctcgacatggcctatctagccacacctgtgctaggagtcggttctcgcattacc<br>gccttagatcgtactattgacgccattacgttgaaacctcgaatcgacctccaagatgtg<br>tatacaattgatcccacacactaactctgcgtcagatagagtttaatctcttcggggacttca<br>atggacgacattgctcgtggattgttacatcgggactggcgtcgtcaatccaccatcgtc<br>ttgctcccttctcgtcgctcgctccttgagtacctattgtctaatccttctgtctgtccg<br>gacggcttaaatcgttctcgccttaaaggattccaaaaacgcccaaatgattttcgtgtc<br>caaaacttcttctctccactgattacggactcaacatcaattgctacgtattctcggtgg<br>cttaatgctcatcctattgtgtactctaccactcacaaagtcgctggtgctcgggtacgt<br>ctctttggacctgctaaattatacattctgtcacccgatgttctccgtgaattatccatt<br>ttgaaatccactgatcgcatcttagttgtacccacggcgcgctcctcacttcctgtatatcggttgtttc<br>cccagtgcttctactagtaattgcgtactcactgcgcgcgaacgctggaatgccctgat<br>gttcaccctgtcgtaaaggcaatcaattagcttatgaccatcaatatcgtgtcactgcc<br>cgctatctcagaccctcttatctcggctcttcttcttgggaaccggtcggtgaagacg<br>ttgaaggtacagccagtggaagctagagcagcacggtcagttggtattcgcgttcaagcg<br>atgacacctcctcgtggtattaacacctcaattatccaggtcgttgatctcaggttgcaa<br>tgccggcattcccttattcccaccgaaaggccattcccgctaacgttcatcggcctccca<br>tcgtgtctgcttcaacatttggatctaacattatccgatgattgggtgcccattcgtgat<br>catacaggcatgtttgaaatgtggtttatgattctttacgctcactcttgtgataagatcctt<br>gacggacggggaaatgccgctttcctattcccagctctactaacgcgttgtcagttaac<br>tatgtacagctcacgtcgactgcatctccacgtcctcaatcgttggcggtaacgcatct<br>gggcggatagattccattgggctgtgcatgcctaaaggatccttcaagtcaactatgatt<br>aaaatttctcactggattggagatttgcggcactcgagtgatgtatccagacgtcgtgatg<br>gatagtgatgatgtgggcgatgctttggatcctacttttgaaaccgcgctacacgatgca |

TABLE 2-continued

Nucleotide Sequence Listings

| SEQ NO. | Sequence Description | Nucleotide Sequence |
|---|---|---|
| | | ttgttggctcttgatccgccttttgacgttgacaaattagctagccccaccgatttagtc<br>aaccaggaatatgtcgcgtctcacatgtacccaacattcttacggctcgtcaatgagttg<br>ctaacgcctaaagcttcagaattgtactcagagcgtagcgttgaattccgatctcttacc<br>tacgcgcatgctgattctgaatttcttaacgcatgttggaccgctcgcttgatgcgatgc<br>tttatcaactatcatgaagagcaaaacatcctgcttcgtcctggacgcgttggcggtgtg<br>ttattccaagtcgcgttgagtcgctgctataagatgttcgctacttccactcctgcctcc<br>cctttatcactgttcctcaagtcgttgttcgttccttggattgaatctgctccactacta<br>gcgaacttgactccaaacgagtcctctcgcgtgttagcgtggtacataccttcttcgtat<br>tggagtgacaatggttggtgcacttgcgacacccatcgtcatgttaccttctctttcatt<br>cgcggtcttcctgcggacctgtcggtgttagatctgtttgattggtctcggttccgcgca<br>actataaacgtagatgcgtctctagtagagctaggcgctgatattcgtgcggttaaggtg<br>tcagttcattggacatctcagaagccactgtggacgtctttgataatcgcgcgcttttc<br>actccctttcagcattaccacttaagcctccactgtaactgtgcgcctggtcgccctttc<br>ttcgcgaaaaatatgaaactgtatctgtcgacggttggaggcgagcactgacgggccgtg<br>gggcggtgacacccagggagggtatgctggtaaccctgggttagtcgtcttgagatactc<br>atc |
| 5 | modified viral-agent<br>segment M2 | gcttttcagtgccagtctttctcacaagatgggtaacgcgacgtctgttgtgcagaact<br>tcaatatccaaggtgatggtaatcattttgctccatctgctgagactacttcatccgccg<br>tgccgtcattatctttgaatcccggactgctgaatccaggtggtaaggcgtgggttctaa<br>tcgatccttctctaaatgcctccgatccttcctccctacgtctgatgacttcggctgatc<br>tgtcaacacttccccaatccgcgattagtaattctactgggtttctcccaacttctggta<br>tgtatgccatcgctactaaagagacgttgagtgtaatcactgagcacgcaatttcccagt<br>tcgataaattgcagatggcttgtgagttggaccgcgattatctggacgctagaggggttt<br>ctcctgagtctgtgaatattcatagttatatagcatatgttgattgcttcgtgggtgtat<br>ctgcaaggcaagctgcgttaaactttaagcaacacgtgccagttattactaaatctcgca<br>tgacacaattcatgacatccgcgcagaatatgttgcaagtactcggaccttgggagcgtg<br>atgttcgtgagttactcactattcttcctacctctactaccgctggtaaaattacgtgcg<br>atatgaagtctgtcgtcgcttttattgatgatcagctctctgataccagtttgtgccgtc<br>tgtaccctgactgtgctgctgcggcagtggctagacgtaatggtggcattagatggaaga<br>cacctgatactgacgaagctccttcgcttgcaactaacgacattgctgcctcaactatgg<br>gtacgcttgcgaatactacaccactggctgagaagtcgaactcgggcgaggagtcaatgc<br>gcttagtgagtgacgttggtgtggacatcgtctgttctcgtagccctataagttcttcag<br>tttggtcacgtacggttgaacctaaatcgtacaatattagaaccttcgtgtagaagagg<br>cgctttggctacgtgagtgccaggcgactactgggtttgatgtacagtacacactgcctg<br>accagactacacataaacatttctggcttcagaaagggtcagttgtcataaatcttgagc<br>aaacgggtagtatgatgtttgatgtgaacatagcgggtaaagattataagaagggtacct<br>ttaatcctgataatcataagttggtccttttggttatgcagtcaaagatcccttttcgagt<br>cttggactgtcgcttctcagattactggcatcgctcaagtggctgaggttactgtgcatg<br>ctgctgatagttcgactcctaaccagaagataataggtgagacttcgctatcttatttgt<br>ttgagagagagacagtgaccacatcaaacactgaagtcaatacatatctcctgtgtactt<br>ggcaacttgataacgaacagagcaatgatgcaaacgtctggccagacgcatgggatggga<br>tcacaacattgactccgcttacttccggtaccgtgaccatcaaggggacttcggtggatt<br>ccgtcgtaccgtctgatttagttggcgcttatacacctgaagctttggctgccgcgcttc<br>ctaacgacgctgggttaattctagctaataaggcaaccagactggctgacgctatcaaga<br>aagaagatgattctgtgatcgatgagtcttctccttttagcactcccattcaagggtcc<br>tggctgttcaacaacttgataccgtggggacgcgtggtatacgtgcactccagcatccgt<br>ccattctgaaacgtatcgcttcacgagctctccatatgttccttggcgatccaaagtcta<br>ttctgaaacaagcgacgcccgtattgagagaccctgacgtttggaccggttttgttcaag<br>gcgttagagacggcatacggactaagtcgctatccgctggagtacggtctgtgtataata<br>acgttaccgccactcaatccgtgcaaatgtggaagcaggggttcctgacgaaaatacaga<br>cgttgttcaagccatcgtgaggtgctaaggcctctctctgcggcgggtcggtgggcacgt<br>cgtggtgacgctgaatgcacggggaagtgacgctccctggattggcacgttattcatc |
| 6 | modified viral-agent<br>segment M3 | gcttttgagtcctagcgtggatcatggcgtcaaccaagtggggagaaaagccgatgtcg<br>ctctcaatgtctcacgatggatcatctatccgcagtgctgcctcacaattttgtcggtt<br>cctctgtctcattcaacgcctatcccacctcaacggaagactgtactattgaactttatg<br>attggtgatgaactggttactgttcagggtgctcttgccccgttcgacgaatactggtat<br>gacaatcaacctctgttggctcaggctgttgagatgctagcgtctgaggatcgtttgcgt<br>caatttgagcattatgagaaattcctactcaagaagggtcaccaaatagctgagatcatg<br>aaccgactacgtctcttttcacggatgtcctcaaaaccaagatggaagctgacgcttta<br>ccggctttagctcaatacctaatggctggaactttggaggccgtttctactgtccactca<br>cctgatgcttgcgtcccagtcacttcgaagatcttagccaagcagcagaccattgccaag<br>gctcctggacttctcgatgaggaagagtacaatgtcatccgatctcgtttccttacgcat<br>gaagtctttgacctaacgtctgacctacctggggtgcaaccgttcatggacatgtactac<br>gctactgttccccgtgctgactctacaggatggtgtgtgtatcgtcgaaagggcctgctt<br>atccactctcctgatgagcaattctcggatctgaccattttctccacacgtcttactgcg<br>tcacatgagctgcagctggtggctggcgatgttgtcgtagcctgttttggtctcatggac<br>gtctctgacattgcgccatctcatcatgcatcggtccaggaagaacgtactctagggacc<br>agtaagtattcgaatgtaacggctaatgagcatcctctggtattcttctcacctaatgcg<br>ctccgttgggcaattgaccatgcctgtactgattccctggtttctcccccggaatattcgt<br>gtttgtgttggcatcgatcctctggtaactcgatgaccgagacgcgtacaagaggca<br>gccattcttatggatgataagcttccatcagtaggtcgtgcgcgtatggcgctgcgaaca<br>ttgcttctcgctagacgctcaccaatgccatccttcttgctcggtgccctgaaacagtcc<br>ggcggtcagctaatggagcactatcgatgtgatgcggctaatagatacggatctcccacc<br>gtcccgatctcccatccgccaccatgctcaaagtgtcctgaactaaaagaacaaattgcc |

TABLE 2-continued

Nucleotide Sequence Listings

| SEQ NO. | Sequence Description | Nucleotide Sequence |
|---|---|---|
| | | aagctctcttcatcgcccatacctaaagttgattcatccgttggtccagccgctctgctg<br>tctaaaattgctgaccttcagcgtgctaacagagaactgtcattgaagctggtcgatgtt<br>caacccgctcgggaagatcacttgttggcttatttcaacgaacatgtgtgtgtgaacggt<br>aaagatcatgaaaaaggcctgcttgctcgttgcaatgtgtctggcgattcaatcacctct<br>atccttagccagcgtgtgaagaaccgtgagagatttgaaacccgattgcgtcatgaggct<br>agtgttgaatgggaacctcgtgtggaagcgttaaatcaagaactggctaaagcgcgtgtc<br>gagcagcaggatatgatgactcaatccctacagtacctcaacgaacgtgatgaactgctc<br>catgaagtggatgagctcaagcgtgaactggctactctacgttctgccaatgtacgattg<br>aatgctgacaatcatcggatgagtcgtgcgacacgtgttggagaagctttcgtcagtgat<br>gtcgagcctctaccttctggcatacctggtgaatcgaaactaactatggaagaattggtg<br>gatgatctgtgagctttgacctgtgactcgacttctctctgattccatgtacccacggcg<br>gactcggttattcatc |
| 7 | modified viral-agent segment S1 | gcttttttcaatcccttgtttgtcgatgctgcgtatgcctcccggttcgtgtaacggtgct<br>acagctatatttggtaacgtccattgtcaggcagctcaaaatactgcaggtggtgacttg<br>caagcgacctcatccataattgcatattggccctatctggcggcgggtggcggtttctta<br>ctgattatcattatctttgccatcttctactgttgtaaggctaaagttaaagcagacgct<br>gcgcggagtgtttttcaccgtgaacttgtagcactgagttctggtaagcacaatgcaatg<br>gctccgccatacgacgtttgaagtacgacgctttgatttctgcccaatatcccttcgtga<br>gcttgctactccatcatttactgctgtaactgggattgacccatcgcagtattttaacat<br>tgagcttccgcatactcatcctctctactctaaactgccgactctgttatctcagccctg<br>cagagttcacgtgcgtttaattcgccgattcgctctccgctcaacgttgtcgggcatctg<br>tgagtacgattgtgcgttactgttctcccacacgccatcgttccattatcctcatccga<br>ccagcagtcttatcttatagttcattgggatggcgggtctcagtccatcacagcgaagag<br>aggtcgtcagcttgatactgtcattgacttcgaacgcgactataaatcctggcgatctga<br>tgtcaatccatgagcggttgaacaattggaagcgtctacagaatcactatatcgctcca<br>tttccagcatgtccactaccgtttccgacatttccgcagatttgcagaacgtgactcgcg<br>ctttggatgatgtgaccgttaacttaaatggtatgagagtcaccattactacgtttcaag<br>attctatttccactctctcaacaactgtgactgacttatccagtacttcttctgcgcact<br>cggaagctctatcttcactccgaactacagttaatgggaactccaccatcattaacaatt<br>tgaaaagtgatgtatcgtcaaacggtctagctattacagacctgcagaatcgcgttaaat<br>ccttggagtctacttcgagtcatggactgtcctttttctctcccccttagtgtcgctgacg<br>gcgtagtgtcgttgaatatggaccgtactttgctctcagcgagtctctttgacgtctt<br>actcagcagaggcacaactaatgcggttccaatggatggccagggactaacggatcgt<br>cggacgacattgacatgaacgttaatgctcactgtcatgggagacgcacggattacataa<br>tgtcgtccacgggaggtcttacagtcactcgtaatgccgtgtctttaaccttcgacttga<br>gttacattacaagcctcccatcagacctctcgcgtcttattcctagtgcaggatttcaag<br>tcgcgtcgtttcctgtggatgtatccttcaccagagattccacaatccatacgtatcaag<br>cttatggagtatactctagttcgcgtgtgttttactattacttcccgactggtggtgacg<br>gtcccgcaaatattcgtttcctgaacgtgcgtaccggcatcgacacttaaggtgtggcgc<br>cgtacggggattggttattcatc |
| 8 | modified viral-agent segment S2 | gcttttctcccacgatggcgcgtgccgtatacgacttcttttctacgcctttcgggaat<br>cgtggtctagcaacgaatcgtactcaactgtcatcactactatcaagctcgaattcccca<br>tggcaacgatttctatcatcaatgactccattgacagcgccaggtatagtctcaacacct<br>gaagcaccctatccaggctcgttaatgtatcaagagtctatgcttcacagtgccactgtc<br>cccggagtgctcggcaatcgcgatgcttggcgtacatttaatgtcttcggactttcatgg<br>actgatgaaggactgtcaggactggtagctgcccaagatcctcctcccgctgccccgtat<br>cagccagcctctgctcagtggtcggacctcctcaactaccctagatgggcgaacagacgt<br>cgtgagctgcaatctaaataccctcttctgcttcgtactacgcttcttttctgccatgcga<br>gccggtcctgttctttatgttgagacgtgccgaacatgatctcaggccgattggctgat<br>tggtttatgtcccaatatggcaacaatttcgttgacatgtgtgctaggctgacccaatct<br>tgttcgaacatgcctgttgagcctgatggaaattatgatcagcagatgcgtgccttaatt<br>agtttgtggctccttttcatacatcggggtagttaaccagacaaataccatcagcggttc<br>tacttctcctcgaagactaggggtcaagcgttggacagttggactctattttatgccacc<br>aacactaaccgtgtccaaattacgcagaggcatttcgcttacgtctgcgcgcggtctcct<br>gactggaatgtagataaatcgtggatagctgcagcaaacttaaccgctatcgtcatggct<br>tgccgtcaaccgccgatgttcgccaatcaaggtgttatcaatcaggcacaaaaccgacct<br>ggcttctccatgaatgggggactcccgtccacgagctcaacttgttaactaccgcacag<br>gaatgcatccggcagtgggtggtggccggtctggtgtcagcagcgaaggggcaagcacta<br>acgcaggaggctaatgatttctcaaaccttatccaggcggatctaggacagattaaggcg<br>caggatgatgcactgtacaaccagcagccaggatacgcaagaagaatcaaacccttcgtt<br>aacggtgattggacaccaggtatgactgcgcaagctctggccgttctagccacttttacc<br>gcttaggcgtagggtcgtacgctgcccgagtccagccctccggcagcacgtggatgtatt<br>catc |
| 9 | modified viral-agent segment S3 | gcttttgagtccttagcgtgcaagccgcaatggaggtacgtgtgccaaactttcactcg<br>ttcgttgaaggaataacgtctagctacttaaagactcctgcttgttggaatgcacaaacg<br>gcctgggacactgtaacctttcacgttcctgacgtaattagagtcggtaatgcgtactgt<br>tgctctcagtgttgtggcgtactttactacggaaccctgccatccgacggaaattacttc<br>ccgcatcacaagtgccaccagcaacagtttaggactgataccccgctactacgatacgtg<br>agaatcggtaggacaactgagcagttgctggatcaatatgctgtcgctctggagtctatc<br>gccgagcactatgatgagattagccaacgtatggttgacgagcctgagaatgatgaagtt<br>acgccccttgacatcgtaacgcgtaccgagtccatcagaagtgacaaggcagtagacccg<br>gatttctggactcaccccttgagcgacgctctgatgattctcgtcgagacatcgcctca<br>gcatgttggaggatgattgacgcatcatcacgtagtttgactcttcccaattgtcttgtt |

TABLE 2-continued

Nucleotide Sequence Listings

| SEQ NO. | Sequence Description | Nucleotide Sequence |
| --- | --- | --- |
| | | tccccatctgtgcatccacgctccgtctttggtcaaatgcaaacgaccaccaccatatat<br>gacgtcgctgcgtccggaaaggctgttaagttttccccgatggttgctacccttgctcaa<br>cgcgatgccggacctgtgatgctcgcgaacgctgatccagccgacgcgtatattcattt<br>tggacatctcatttcgcagtttcgccgctaattggaggagtcgggattacgggacagtac<br>gctcgtgagtcctaccaccacgtgggtcatccagtcgttgggagtggtaagaaggcgtcg<br>cactacagaaacctgttcatggaagcgtggcgtggatggtcaaagtcagcttttgcatgc<br>gctacaggaatggaaccagccgaatgcgagtctcgtttgaggggtcacgctcgcactatg<br>ctcggacggtctctgccgaatgtctgtgatgatgacgtctctcaacagtctggtgctgtg<br>ctagcgtctctgcagaagactaccaaattcactgttgtggagtgcagttggtaagtacct<br>ccgggtcaaaatgcacataggctccccacctatgtgacggttagcgggactcacctattca<br>t |
| 10 | modified viral-agent segment S4 | gcttttttgagtccttgtgcagccatggacaacacagtgcgtgttggagtttcccgcaaca<br>catccggcgcagctggtcagactgtttttagaaacttttacttactacgatgcaacatct<br>cagccgacggtcgtaatgcaacaaaagctgtgcaatcccacttttccattcctttctcgtg<br>ctgttcgctgcttatctcctctagctgctcattgcgctgataggactctacgtcgtgaca<br>atgtgaagcagattcttactcgtgagatgccattcgcatcggacctaattaattacgcgc<br>accatgtgaattcatcctcccttactacttctcagggtgtcgaggcagcacgtctagtgg<br>cccaagtttacggagaacaactgtcgtttgaccatatctaccccactggttctgcgactt<br>actgccctggagcgattgcgaacgcgatttcccgcatcatggctggtttcgttcccatg<br>aaggcgataactttaccccagacggttctattgactatctcgctgcagacctggttgcgt<br>acaaattttgtgcttccttacatgctagatattgtggacggacgtccgcagattgtacttc<br>catcgcacactgtcgaggagatgctgtccaacacgagcttgcttaattccattgacgctt<br>catttggtattgaatctaagagcgatcaacgcatgacccgtgatgcggctgaaatgagtt<br>ctcgttcacttaatgagcttgaggatcacgagcgagggggtcgaatgccttggaaaatca<br>tgacggcaatgttcgcggcgcaattgaaggtggagttggatgctctggctgatgaacggg<br>ttgagtctcaggctaatgctcatgtgacatcttttgggtctcgtctgttcaaccagatgt<br>ctgcttttgtcccaattgatcgcgagttgatggagctggctctactcattaaggaacaag<br>gtttcgcgatgaatccaggccaagtcgcatctaaatggtcgctgatacgacgatctggtc<br>ccactcgcccactgtcaggcgctcgccttgagatcagaaatggcaactggacgattcgtg<br>aaggcgaccagacgcttctgtctgtctctccagctaggatggcgtaaacgggacccatgg<br>tgcgggtgaggggccgccacaccctctgccgcgacctggactcttattcatc |
| 11 | Avian orthoreovirus strain S1133 segment 11 (KF741756) | gcttttctctccgaacgccgaaatgagttcgcgcaaagtggctagacgtcgtcataaggat<br>gctactgaatctaaggacactaaagacactaataaatctaagccatcttctattgatgct<br>aaagaatctacggatagcgctacggataagaaagtcactgctccaccaccaaataatccg<br>gctgcttctactccctcctccactgatggggcttcccaaacatctgtcgctaagcagacg<br>aatgataatgacgcctcagttaaggaatcagctcccaagcctactgtctccagcgacggg<br>aaagatgggatgcacggtgctgtgaagtcgcaagacgctaaggctaccgtagctgtagat<br>aataataaggatagagatgtagtatttggtggtgcaggttctggtgacaaaaatgctatc<br>acgaaaactggctccgttgacaatgatgggggtgttaaggtcgttccagccaaggatgct<br>acgatatcttcggccaaagccatgatggacaaaagcagttagtcgctggtcttccgaaa<br>caaccgaagtctgctaatcatctgtgtaccgtctgcatggctcagtttgcgtcagctgac<br>gctcttactattcaccaaactacgcattctattggttccaacgcggctctgacgagtttt<br>tcgatctctactgctgttgaagaattcattcaatcatgggctgctgccacatccacggct<br>aacaccaagacggctttgactgtgtctgacgttgactcactgatgatgactgaaggaata<br>cgccttataacttgggattctgggttatgcacgtcttttgagcttgtcccgatcgtccat<br>tcaaacactgttcaagatgttatttcatattcatggtttacgtcaagctataacatcacg<br>actccttcccacaagcgactgtcgtgcggattgtcttgcgtactaactgggctgccaaa<br>ttggattctccctcttcgtcgcgtgaatgtgatcttcgtcttgctccacctacagagagc<br>aatgctcgatcattctcaatgctactcaatacgggtgcgactccagaaggcactttcaac<br>cccaacaccccttcgtatgaacgtgctgcagatgtgtcttcagtatgttctagctaacttg<br>cacctgaaccgtagcactcagtttaccatggatttgactgccgcggctcccaatctatct<br>gcgtctcaactccgtatcgttccagaggataaggagggtaaatggtttcctgtcatgtat<br>ccatcccgagtgaacatcccactgttcaacaagacggctgattttgttaatcagtgcatt<br>cgtgatagagttggtcgatacgatcgcgcccagacttttgctggtcgcaccttctgaatgg<br>gctgacatgtgggaaacagcagacgcgttaactctccgtccgcgaaatgtggatgtca<br>cgcatttctcaaatgaacattactcccgctgatattgctgacgctatctccagatgttct<br>cagtcttctgctcactgttgccgcgccgacagctccttctgtggctcgttttgttaccttgg<br>cgggttagttctgatgagaggcagctgctccaactgctgatgtacttaaatgttggtact<br>agtgctgactacgttcaaccgattctgtctgcgttcgctcgaactctgtctcgtgtgtca<br>ccactgcgaattaatcctaccctaatcgctaatgctatgtcgacaattgtcgagagcact<br>actaatactcagagtcctgctgcggctatcttgtcaaagcttaaacctgtcgcatctgat<br>ttttccgactttaggtctggcatgtgccgcttggttatataatggttgtgtccagacatac<br>ttgtctgaggattcgtatccgagcagcggtgggtctgtcactagcatcgacacgttgatt<br>gatatgtttgtgtgtttgctggcgttgcctctggttactgatcctaacgctccttgtcaa<br>gccttatggttgtcgctaatgctatggttggttacgagaacctgcctatggacgaccct<br>aattttactcagcagagactggctgcagcgttcaataatcctactacctggcctcaatgc<br>ttcctccaccctcaaaatattgatcggcgccagtgtccgattcttcatggtgggctcag<br>cagattcatcgtaattggcctacaccatctcagattacttatggtgcgcctgatatcatc<br>ggctccgctaacttgttcactcccctgatgtgttgttgctgattccattacaacataggcc<br>atccgtatcaccaatcccaccctgaacttcgataatgagttgacgactggcgtaacacc<br>gtggtgatttagtcctgcgcattattgacagtggtcggtaccagcctaattggaatcag<br>tctattcgtgcgtctatgcggaatgcgatgacgaatttcaggattattaagtcctataca<br>cctgcttacatagcggaattgctacctgtggaactggcggctatcgctccaactctaccc<br>ttccagcctttccaggtgccgtttgctcgcttagatcgtgacgctatcgtcacccatgtc |

TABLE 2-continued

Nucleotide Sequence Listings

| SEQ NO. | Sequence Description | Nucleotide Sequence |
|---|---|---|
| | | aatgtgtccagacaagctcccaacaatcttgctcaacctgcattgaacatgtccatgacg<br>taccagcgcacaggagttccaatctctcttagtgcccgtcccttggccgtcgctctttta<br>tcaggtcagtatcctactgatcctcctcttcagaccaatgtttggtacgtgaacactctc<br>acacctctatattccaatgatggtctcttaacagcgtgcagcatgctatggttgcttct<br>gaagcttacgcaactttgatcactatgctggctcagtgcactgacatgcagtacccgtg<br>gatcggccattgaactggcttcgtcagattaatttggctgccaatgaagcgacgattttt<br>ggtcgctcaattaactcacttttccaaacgcttttgacctctcaccctctactgtgttg<br>cttcagcctttcttggagtctgatccacgtgcaacgcagctcgccatttcttacgtccgt<br>tataatggtgatagtgagaccttcgtgccaacagtgcgtccgtctatgatctcagaggcg<br>acattgctcgttgagcgtactctctcgcacgaatacaaccttttcggtttatgtcgtggt<br>gacatcattctggggcagcacatgactcctactgcgttcaatcctctggctccgcctccc<br>tctgtcatttttaatagggtgatgctgacgtttatgagtttggcccacgtagcttcgcc<br>aacttcggtatgaatgggaggagatcttggtcatggatgcgaacggcgtgcgtcgtcca<br>ttacttggccgttgggttatgccactgcagcttctgatggtgaatattggcgtctttccc<br>aagttgttgttggatcgtatcttgaagggacgcttatacatccgacttgaagttggcgcg<br>tatccctacactgtgcagtattaccagggacgtgagttcacagatggtttcactctgctt<br>gagcaatggatgtctaaggtgtcacccatgggtatccctcccgtcccttcctcatgcca<br>cagtccgaaggacacaacatcacttcaggcatggttactcattacatctggtccactgaa<br>tacaatgacgggtcactcttcgccacgaacactgacctgccggttactgtgtttggtcct<br>gaccgtaccatcccaatcgaacgctaccgggcactcgttgatccaggcgctcttcctgct<br>accaaccaactgccgcacaccatcgacctttactgctcactgagacggtattatctggaa<br>acacctcctatcaccgctactgttaccacttatggcgatggactccccgcgctgaaccat<br>tagagcggcgaggctagacgcgagttgatcgcgtcgactctcgttggagattattcatc |
| 12 | Avian orthoreovirus strain S1133 segment 12 (KF741757) | gctttttcctcaccatgcatgtcaacgggtttgatgatgctactctctcttacgcacaat<br>ccatctcggggttattccaatgacaaataagttatttgagcaagcatctgcatcgatac<br>gtgccttaccgcgctcacacgtttatgctctattagatgatgtgaattttctgttacat<br>gtgtgatcccgaatcgcatcttccatcaccctgatcactctgagtatttttatgttgatg<br>cagttaataggttagacgaaaacaagttatcgatcctgatgatgtattcgttccaaatt<br>gtaacctgcagggtcttatcactccaatggagaggttaccaaattatggtcagttgctg<br>agattatttcatcgaacgctcgggatggcttgccatctgcacgcatagcagctacattt<br>ataacatttcggtatctcaggctcgtcaagttaaagctccacttgaatcatttttgttac<br>ctttgctgttatctgaaacctgcccattatcggatgatccttgcggatttgacaccacag<br>cttctccccaatccatgcaaatctgacgcgttatgggtgctacgtgaaatcagtcggacta<br>tttgtggatcctcgaaagaccgttcaccctggttattgcttgattcaggggtcgcgtggt<br>tcatgtctccgttaatgtcatcagccattccgcctctcatggctgacttaacgaatctag<br>caatctataaacaaatttgttctgtgtcggacgagcttcattctcttgcggttcaagtgg<br>tgttgcaggctgcagcgtcacaatcatatggccactacatattgcagacgaagtcaatat<br>tccccagaatacattgcataacatgtttcgtacactcaccgatggcatcgttccggtta<br>tagattggctggaaccgcgttctaactatcgctttatgcttcaaggtgcgcgtaaagtga<br>cttcagacgatgcgaatcaagctccggataacacagacgctgccgagcaacttggccgta<br>gaatggggtgccttgatgtcgtacgctctctacgcaagatgtcttcatctatcactgtcc<br>attcacacgatgctatgaccttgtacgtgatgctatgtcgtgcactagtggcatattta<br>ttacgcgacaacctactgagactgttttaaaagagtacacgcaagcccctaccattgaag<br>ttcctattccacagtcagattggtcaccgcctattggatctttgcgatatctctcggatg<br>cctgctctctccccgctgtatatttggctagggcttggcgaagagctgcttctgctgtag<br>tggataaccacgtacctgggacccctttatatcaggcatccttcgctctcagtatgtga<br>cgtcacgtggtgggtctggtgctgcgttaagagatgctttgaaggctgcagaagttgaac<br>ttcctcagtatcctggggtcagtgttaaggtggcgaccaagatttatcaggcggctcaga<br>ctgccgacgtaccttttgacaagttatctcgggctgttctagctccgttgtcaatgggct<br>tacgtaaccaagttcagcgacgtccaaggaccattatgcctatgaatgtcgttcaacagc<br>agatctcagcggctcacactctctccgctgactacatcaattatcacatgaacttgtcga<br>cgacatcgggtagcgctgttattgagaaggtggttccattaggtatgtatgcgtcctgtc<br>cccctgctcaagcggttaacattgatatcaaagcttgtgacgcgtctatcacgtaccagt<br>attttctttccgttatagtcggtgctattcatgagggtgcagcaggccgccgcgtctcgt<br>cctcattcatgggagttccaccaagtgtgctatctgttgttgatgctagcggagtaacgt<br>cctcaatgcctatctcaggttttccaggttatgtgtcagtggttggctaagctctaccagc<br>gaggttttgagtatcaagtaacggacacgttctcgccaggcaatattttcactcatcata<br>ccactactttccctctggctcaacagcgacgtctacagaaacatactgcaaataatagta<br>cgatgatggatggattttttgcgtgcttggattccttcctccggtgcgtctgatgtgctga<br>agaagttctgcaaatccatttcaatacaacggaattacgtttgtcagggtgacgacggtt<br>taatggtcgttgatgggctatcaacaggtaaattatcaggcgagataatcgatgaattcg<br>tcaaagagttgagagcctatggtaaatcgtttgggtggaactacgacatagagtttaccg<br>gaaatgctgagtacctaaaattatatttcctaaatggttgccgtataccgaatgtttctc<br>ggcatccgatctgtggcaaagagcgcgcttcaggggataagttagaaatgtggccatcca<br>ctattgacatcttcaatggcatatttgtgaacggtgtgcatgatggtttaccgtggcgca<br>gatggttgcgttattgttgggctctcgctctcatgtgttctgggaaaaccgtacgtcacg<br>acgattctgaggtgctgatccaatacccctatggtccttgtgtattggggtttgcctc<br>ccgtgagtgcgtttgggtctgatccatggatcttttctccatacatgcccactggtgatc<br>atggtttttactcaatgttaacttagtgcgtcctctgatcactaacttgtccccgtctt<br>cagacacttcaggattattttgtcaactgatcataacgtcttgttcaactctgagctgg<br>tttatcagggctattacatggctcaatgcccacggcaaccctctcgttcgaatcgtaggg<br>atgatcctggctctgtacagctgtttcgttaaggctttagagtcttatctttatatttccc<br>ctgagctaaagtctcgagtgcgacttggtcgcgaccgatggcaaaagttggttgggtata<br>cagaaaaatctcctccgtcgcttgatgacgtggctttcaaatggtcccggagtgcacagg<br>aagctgatcttccaactgctacagagagattcaaagcatggatctggctttactggcagcca |

TABLE 2-continued

Nucleotide Sequence Listings

| SEQ NO. | Sequence Description | Nucleotide Sequence |
|---|---|---|
| | | gacgtcggacgtatcaaggtttctccaagttgttaaacacctacttgagggtgacttggg<br>atttatctgatcctgttgaacacgctgtagatcctcgtgttctcttgtgtgctggtgttt<br>ctccatcgaatagcgaaccgtttcttaaactgtactccgttggtccaatgatgcaatcta<br>cgcgtaaatatttcagcaatacgctattcatccatcggactgtgtctggtcttgacgtcg<br>atgtcgttgatcgtgcgcttctcaggttgcgtgctcttaatgcgcctgatgatgtggttg<br>tggctcaacttttgatggtagggttgtctgaagccgaagctgctacgttggcagcgaaaa<br>tacgacgatggatattaacgccgtgcaattggccagagttgttaatctatctattcctg<br>actcgtggatgaccatggacttcgatcgcttgatacgagatcgtgtctatcactcctc<br>taaccgtccggtccctaaccaccgatctaccctctggtgtgccgtgggctcgcgcgatac<br>tgcagttcctaggtgcgggtgttgctatgacggctgttggacccttgcgtcgtccttact<br>tgcactcagttgccggaggtatgtcctcatttattaagcagttccgccggtggatgcgtg<br>ccgaaacgaggtagcgtccgtgctcggcatggctcgaggaattactcatc |
| 13 | Avian orthoreovirus<br>strain S1133 segment<br>13 (KF741758) | gcttttccacccatggctcagattcgaggccttcggttgtctacgacactctcagctcca<br>ccaccaagaaagattgtaacctcgcatacgtatgatgaactaatctccgctttaaagctg<br>acaaccaaaccttggcgctctttaaagtcacgcggcaatgactcaatcacagcagtccgg<br>cttctatttcccccttaatggttacattgagcccatgcttatgttagagaaggacatgaca<br>tacgatgcttttgagtcttggattacgccccttctttctgctctagctgaccagttgctt<br>agacactaccctattgctgcttatcacgggcggttgattaacccgttgttaaccaatgct<br>gttgttgccgctttcttatcgaatgtgccctatgcgcatgcattggatcatcttttctg<br>gttcgtgggaacgttgaggatattatggatgcaggaatcacaattcagaatcatttatgg<br>tttgaccgtggtgctatagtaactccggccgggcagaagtttgttcagttgactggctat<br>aattttcatccaatgatccgtgcttattttctaagcaattgcgttgttatggtcttgtt<br>tactattttcttaacatgtccgattgtctgacgtactgttggcgtcatctctctaactcg<br>actcctctgatacatttgatcgtccgtccaacgggattcattgcttggtgccctccgaa<br>tccacgacacctatcgccggttcattacctgtgtcagctctcagctccattctgctggag<br>tcttgtcttcagcaatcctcacttaatgctcttactcctactggctaccagtcgttagg<br>caggtggaggtgttgctacctctatcgtcaccattttcgaacgtcaaaatactctggaa<br>tattctctttttgctctttcgaatgctctgattaatggttatcaattcgttgatttacgt<br>cccggacatccagattgcgctaccgttgctgctgttttagctaggttaactgatttctcg<br>aaaggtatcactgttattcaaccacgccctgctcttctcactgttaatcatgatagtcct<br>ctgacgtacagtggagagaatgctaatttcatccaacgcttagcttctatgtctggaaga<br>tctattggtcccgtcgttatttgggaaatctgtcgatcatgccgtcggttggatgcctcag<br>tttgatcccgctacatcgtacaatcctgatttatccattagattcaatctcacgagctacg<br>acactgccactccgtgctaagtattctactttctggtctggccccgcgctcttttcctt<br>gcttcgtgtgacaggcacaatggcgtgtatgacattcagttcatggcccaatttcctcct<br>acgtatttcagcgatgatgatgccttttctaggtccaggttttcttcctatcgtgctgtt<br>aaagatcgatcgttgttaaaagatactgccaatctgatgtacatttcaaacttatcgagc<br>tcgcatgaccatcgtcttgtcccctgattctaagaccatgatttacgtagggtcttccggt<br>acgcatgcagataaccaaccttccattattaaacctcttttagctgggtctcttccaggt<br>gttttccgcccctatccgtgaagcagattggttgggaggttactaacgggactatttgt<br>gacattgagctgcctttagctacggcacattcttcttcgtgtacagtgacgtagaccag<br>gttcagtcaggcgattccgacctagacgcttcctcccgacgcttttgctctcaattggat<br>atgttaatgaaattgacgtttactggcggttccttagttgtcaagtgcaattttccgact<br>aacttggtttggcgtcatatctttctaccatttctccctatttctcgtccattcatctg<br>atgaagcctcttgtgtcgaataattttggagttgtacttattatttgcagagcgtttgcct<br>gtccctgatgccgcattccgtccgtcggcggatgttgtcgttttctggcgatctcaactg<br>caacgctaccgggtattgcgcgactcattctctaatgtaccctctatcggctctactctt<br>accttagatgactcattgactgtatctgttctgaattttgtcgatgtcacttcccttttcc<br>tccattgaggatcaacgagctttatccgcttttctcagtccttacctccttggggtctcag<br>aagttatcgcttcatccctactttgatagttatcgcacacagctcactggaataatcact<br>ccccattctcgtaacatcttaaatagattagcgtacgtcccgcgtgtcttcccttcaacg<br>atcgacgttcaacatcgtgtcatggctgcctcagatcccgagattttggttttcgctcc<br>aattcgtggactcaattgtccttcttctacgatgctacgttgactgcgacggattttact<br>gatgtgaagcattggttggatctgggaactggaccccgaagcgcgaccgttgtcttttctg<br>ccgactgatcttcctgtcacattgtgcgacactcggcctttcgttttttccgtctggctgt<br>tgggccacgttcactgacttcttaagttatgattacctcgttacgaacgtcgttttatca<br>actggtgccgatgttgtgtcctgcattctctccctaggggcagcctgcgctgacgctaac<br>atgactctacatgagggcgtgcgtcaactaatttcccagtgcgtagatgctagtgttaaa<br>acgctgtttttgcagcttaattgtcccttccatcagcgggtgatatgtctcgggagatc<br>ctcgagttggttcagactaattcaacctacgtattccataccttaggtcgcattgagccg<br>ttcatcccatatccgctctcttggaaatagtcgaggatttgtgccctggcatcgtcgtt<br>gagattaaaacgatggattcttctctttcatggcttgactacgctgtccaatctaatgca<br>tcagtgacgtcggacgacattgtcttagcgatgcgtttgtctcacttctgtcctctttt<br>gtgtttcattttgaccgtcattctgctcaattcccggatgatgcgcgtgttggtgctccc<br>ttcaccgtcacattgttggattatgaagatactcgatcatatgaggtgacttagacaat<br>gtcactattgctactattactgcaggcgctctggtcggatttcatctggtgtaagtgtc<br>acctcatccaacaatcagctggttatgactattgatcctgcgagtccaggaattcttct<br>gtcattcaggtactcccgctcgcatctcattaggcagctgcgtgatagaggcgccggac<br>ccatcccttctctgatttttcctgctacattagatacttccttgtcagggaccgacctg<br>gagttacgtctgtctctggtatgacgtcgctctcttctacgtcgacgaagcgcactct<br>cgactgctgccccgtatccgataccaagtacgagatttatcgtaaggatcaagcgccgaat<br>agtcgagtaatcaactatatctttgatcgttctgacgtgttctttaaattggtgctgtgc<br>gacgtctctccatcggaataggtcgcttcatctatcgtgagttaccggagctaagttcc<br>cctgtatggcctgatgatgcgcgtactttcttatccataccatttgaatccctatggtg<br>attgtatcgccggacggaccccgttaactatgacggtgccaatttcactcctccaacttca |

TABLE 2-continued

Nucleotide Sequence Listings

| SEQ NO. | Sequence Description | Nucleotide Sequence |
| --- | --- | --- |
|  |  | tggcttacagttgacggcagcacctgcgtcatagatggccgtccctcattttacgtgccc cctggccgatatggtctggtgagagtctaaacgaccgcgggcctccagtaaaagggtgtt attcatc |
| 14 | Avian orthoreovirus M1 (KF741759) strain S1133 segment | gcttttctcgacatggcctatctagccacacctgtgctaggagtcggttctcgtattacc gccttagatcgtactattgatgccatcacgttgaaacctcgaatcgacctccaagatgtg tacacaattgatcctacactgactctgcgccagatagagttaatctcttcgggcacttca atggacgacattgctcgtggattgttgcatcgggactggcgtcgtcaatctaccatcatc ttgcttccttctcgtcgttctcttcttgagtacctattgtcaaatccttctgtctgtcca gacggtttagatcgttctcgacttaaaggattccaaaagcgtccaaacgattttcgtgtt caagacttcttttctccactgattacggattcaacgtcaattgctacatactctcggtgg cttaatgctcatcctattgtgtactctactacttacaaggtcgctggcgctcgggtgcgt ctcttttggacctgccaaattgtacattctgtcgcctgatgctcttcgtgaattatccatt ttgaaatccactgatcgcatcttcgttgtacctacagcacgtgtatatgtcggttgtttt cctagcgcttctactagcaattgtgtccttactgcacgcgaacgctggaatgcccctgac gttcatcccgtcgtaaaagcaatccaattagcctatgaccatcaatatcgtgtcactgct cgttatctctcagaccctcttatctcagctcttcttcttgggaaccggtcggtgaagacg ttgaaggtacagccagtagaagccagagcagcacggtcagttggcatccgcgttcaagcg atgacacctcctcgtgggatcaacacatcaatcatccaggtcgttgatcttaagttgcaa tgtcggcattccctcattcccaccgaaaggccattcccactaacgtttatcggcctccca tcctgtttgcttcaacatttggatctaacattatctgatgatttgggtgcccattcgtgat catacaggtatgtttgaaatgtggtttatgattcttacgctcacttgtgacaagatccttt gatgacgggggaacgctgtttttctcattcccagttctactaatgcactatcagttaat tatgtacagctcacgtcaactgtatccccacgtcctcagtcactggcggctaatgcgtcc gggtggatagattccattggactgtgtatgcctaaaggttctttcaagtcaactagtgatt aaatttctcactggattgtggagatttgtggtacgcagtaatgtattcagacgtcgtgatg gacagtgatgatgtgggtgatgctttggatcccacttttgagaccgcactatatgacgca ctgttggctcttgatccgccctttgacgttgataagttggctagtcccaccgatttagtt gatcaggagtatgtcgcatctcacatgtacccaacattttttacggcttgtcaatgagttg ctaacgcctaaagcttcagaattatactcagagcgtagtggtggagtttcggtctcttact tacgcgcatgctgactctgaatttcttaacgcttgctggaccgctcgcttgatgcgctgc ttcatcaactatcacgaagagcagaatatcctactccgtcctggacgcgttggtggtgtg ctattccaggtcgcgttgagtcgctgctacaagatgtttgctacttctactcctgcttcc cctctgtcattgttcctcaagtcgttgtttgttccttggattgaatctgcacctttgtta gcgagtctgacgccgaacgagtcctctcgtgtgttagcatggtatattccttcctcgtac tggagtgacaatggctggtgcacttgtgacactcatcgtcacgtcaccttctcttttcatt cgcggtcttccagcagacctatcggtgttagatctgtttgactggtctcgattccgcgcg actataaacgtagacacgtctctagtcgagctaggcgctgacattcgtgcggttaaggtg tcggttcattggacatcccagaagccactgtggacgtcttttgacaatcgcgcgcttttc actcccttccagcactaccacttgagtctccattgtaattgcgcgcctggtcgcccttttc ttcgcaaaaaatatgaaactgtatctgtcgacggttggaggcgagcactgacgggccgtg gggcggtgacacccaggggggggtatgctggtaaccctgggttagtcgtcttgagatattc atc |
| 15 | Avian orthoreovirus strain S1133 segment M2 (KF741760) | gcttttcagtgccagtctttctcacaaaatgggaaacgcaacgtctgtcgtgcagaact ttaacatccaaggtgatgcaatcattttgccccatccgctgagactacttcatccgcag taccctcgttatctctgaatcctggactgttgaatccaggtggtaaggcgtgggtctga ttgactcatcgctaaatgcttcggatccttcatcattaagattgatgacttcggctgatc tatcgacgctctctcagtcggctattggtaattctactgggtctcttctcacctccggta tgtacgccgtgactgctaaagagacgttaagtgtaataactgagcatgcaatttcccagt ttgataagttgcaaatggcctgtgagttgaccgtgattacctggatgccagaggcgttt ctcccgagtccgtgaatattcataattacatcgtctatgttgattgttttgtgggtgtgt ccgcgaggcaggccgcgtcgaattcagacagcacgtgcccgttatcacaaaatctcgta tgacacaattcatgacatctgctcagaacgtgttacaagtgctcggacctttgggaacgtg acgttcgtgaactactcactattcttcccacttctactaccgctggcaagatcacatgcg acatgaggtccgttgtcactttcattgatgatcagctttccgacaccagtttatgccgta tgtaccctgaatgtgctgctgcggcggtggctagacgtaatggtggcatccgatggaaga cacctgagaccgacgaggctccttcacttgctactaatgacattgctgcctcgaccatgg gtgcacttgcaaataccacgccgttagctgagaaatcgaattcgtggtgaggaatcaatgc gcttggtgaatgatgttggcgtcgatatcgtttgttcccgggcccccgattagctcctcgg tctggtcacgtacagttgaaccgagatcatacaacattagaaacacttcgcgtagaagaag ctctctggttgcgtgagtgtcaggcaactactggctttgacgtgcagtacacgctccctg accaagctactcataaacatttctggctccagaaggggtcagttgtcattaatctagagc aaacgggcagcatgatgtttgatgtaaacatagcaggtaaagattacaagaaagggcactt ttaatcctgataatcgtaaactagttcttctggttatgcagtcgaaaataccttttgaat cttggactgtcgcttctcagatcactggtatcgcccaagtggctgaagtcactgtgcacg ccgctgatagctcgactcccaaccaaaagataattggtgggacttcgctgtcgtatctgt ttgagagagagacagtgaccacgtccgataccgaaatcaatacatacctactgtgcactt ggcaacttgacgataaacaaagcaatgacgcaaatgtctggccagatgcatgggatggaa ttacaacattgacgccactcacttctggtaccgtaactattaaggggacttcggtggact ctgtcgtaccgtctgatctcgttggcgcttatactcctgagtcgttggccgctcgcacttc ctaatgatgctggtttgatcttggctaacaaagcaactaaactggctgacgctatcaaaa aagaggatgactctgtggtcgatgagtcttctccctttagcactcctattcaaggggtcc tggccgttcaacaacttgacaccgtagggacacgtgggagcacgcgcactccaacctcctt cgattctgaagcgcattgcttcgcgagctcttcacatgttcttgggtgacccgcgttcca ttttgaaacaggcgatacccgtgttgagagaccctgacgtatggactggttttgtccaag |

TABLE 2-continued

Nucleotide Sequence Listings

| SEQ NO. | Sequence Description | Nucleotide Sequence |
|---|---|---|
|  |  | gcgttagagatggcattcggactaagtcgttgtccgctggggtgcggtcggtgtacaaca<br>acgttaccgccacgcaatctgtccaaacatggaagcaggggttcctgacaaaaatacaga<br>cgttgttcaaaccatcgtgaggtgctaaggcctctctctacggcgggtcggtgggcacgt<br>cgtggtgatgctgaatgcacggggaggtgacgctccctggattggcacgttattcatc |
| 16 | Avian orthoreovirus<br>strain S1133 segment<br>M3 (KF741761) | gcttttgagtcctagcgtggatcatggcgtcaaccaagtggggagacaagccgatgtcg<br>ctctcaatgtctcacgatggatcatctatccgcagtgctgcctcacaattcttatcggtt<br>cctctgtctcactcaacgcctatcccacctcaacggaagactgtgctgttgaagtttatg<br>attggtgacgaactggttaccgttcagggtgctctcgctccgttcgacgaatattggtat<br>gacaaccagcccctgttagctcaggctgttgagatgctcgcctctgcagatcgtttgcgt<br>caatttgagcattatgagaaattcctactcaagaaaggtcaccagataactgagatcatg<br>aacaggttacgtctcttttttacggatgttctcaaagttaagatggaagctgacgcttta<br>cccgctttagcccaatatctgatggttggaaccttggaggctgtgttccaccgctgattcc<br>cccgatgcctgcgtcccagtcacctcaaagatcttagctaagcagcagactattgctaag<br>tctcctggacgtctcgacgaggaagaatataatgttattcgatcacgtttcctcacgcat<br>gaagtcttcgacttaacgtccgatttacccggagtacaaccgtttatggacatgtactac<br>gccactgtccccgtgctgattctacaggatggtgtgtgtatcgtcgaaagggtctgctt<br>atctacgctcctgatgagcaattctcggatctgactatcttctccacacgtcttactgca<br>tcacgtgagctgcagcttgtggctggagatgttgtcgtagcctgctttgatctcatggac<br>gtctctgacattgctccatctcatcatgcatcagtgcaggaagagcgtactctcgggacc<br>agtaagtattcgaatgtgacggctaatgatcatcctctggtattcttctcacccagtgcg<br>ctccgttgggcaattgaccatgcttgtactgactcctggtttctacccggaatattcgt<br>gtctgcgttggcatcgatcctctggtaactcggtggacccgagatggtgtgcaagaggct<br>gctattctcatggatgacaagctaccctcagcaggtcgtgcgcgtatggcgttgcgaaca<br>ttgcttctcgctagacggtctccaatgccatccttcttactcggtgcgctaaaacagtca<br>ggcggtcagttactggagcactaccgatgcgatgcagctaatagatatggatctcccacc<br>gttccgatctcccatccgccaccatgctcaaagtgtcctgagctaaaagaacaaattgcc<br>aagctctcgtcatcgcctatcccaaagtcgattcgtccgttggtccagccgtactgctg<br>tctaaaattgctgaccttcagcgtgctaatagagaactgtcactgaaactggttgatgtt<br>caacctgctcgggaagatcacttgttggcttatctcaatgaacacgtgtgtaaacgct<br>aaagatcatgaaaagggcctgctcgctcgttgtaacgtatctggtgattcaatctcctct<br>atccttggccagcgcatgaagaatcgggaaaggtttgaaactcgactgcgtcatgaggct<br>agtgctgagtgggaaccccgtgtggaagcgttaaaccaagaattggctaaagctcgtgtc<br>gaacagcaggacatgatgactcaatccctacagtacctgaacgagcgtgatgaactactc<br>caggaagtggatgagcttaagcgtgagctgactaccctgcgttccgctaacgtacgcttg<br>aatgctgacaatatcggatgagtcgtgcgacacgtgtcggagacgccttcgtcagtgac<br>gtcgagccgctaccctctggcatacctggtgaatcgaaaccatctatggaagaattggtg<br>gatgatctgtgagctttgacctgtgactcgacttctctctgattccatgtacccacggcg<br>gactcggttattcatc |
| 17 | Avian orthoreovirus<br>strain S1133 segment<br>S1 (KF741762) | gcttttcaatcccttgttcgtcgatgctgcgtatgcctcccggttcgtgtaacggtgcg<br>actgctgtatttggtaacgttcattgtcaggcagctcaaaacacggcaggtggtgatttg<br>caagctacgtcatccataattgcatattggccttatctagcgcgggtggtggtttctta<br>ttaattgttatcattttcgctcttctatactgttgtaaggctaaggtcaaggcggacgct<br>gcacgtagtgtcttccatcgtgagctagtagcgttgagttctggtaagcacaatgcaatg<br>gctccgccatacgacgtttgaagtgcaacgatttaatttctgtccgctatcacttcgcg<br>acttgctatcccatcatttactgctataactggggctgacccatcacagtattttaacat<br>tgagctcccacacactcatcctctctattccaaattgcctactctgttatctcaaccttg<br>tagggtccacgtgcggctgattcgccggttcgctctctattcaacattgtcaagtatttg<br>tgagtacgattgtgctgtactattctccccacacgctatcgttccattgcctgcatccga<br>tcggcggtcttgtcttatagttcattgggatggcgggtctcaatccatcgcagcgaagag<br>aggtcgtcagcttgatactgtcattgacttcgaacgtgactataagtcatggcgatttga<br>cgccgatctatgaacggctgaccaatctagaagcgtctacggagttattacatcgctcca<br>tttccgatatatccactactgtctcaaatattctgcaagtttacaagacatgacccata<br>cctggatgatgtaactgctaatttagacggttgaggaccactgttactgcacttcagg<br>attccgtctccattctgtctacaaatgtgactgacttaacgaacacatcctctgcgcacg<br>cggcgacactatcttcacttcaaactacggttgacggaaacttcactgccatctccaatt<br>tgaagagtgatgtatcgtcgaacggtttagctattacagatctgcaggatcgtgttaaat<br>cattggagtctaccgcgagtcatgtctatcttttttcgcctccacttagtgtcgctgacg<br>gcgtggtttcattagacatggaccccctacttctgttctcaacgagtttctttaacatcat<br>actcggcggaggctcaactaatgcaatttcggtggatggcacggggtactaacggatcat<br>ctgataccattgacatgaccgttaacgctcactgtcatggaagacgcactgattatatga<br>tgtcgtccacgggaaatctcacggtcactagtaacgtcgtgttattaaccttcgatttaa<br>gttacataacgcctatcccatcagacctagcacgtcttgttcccagtgcgggattccaag<br>ctgcgtcgttccctgtggacgtatcattcacccgcgattctgcgactcatgcgtaccaag<br>cgtatggggtgtactcgagctcacgtgtcttcacaattactttcccaaccggaggtgatg<br>gtgcagcgaacattcgttccttgaccgtgcgtaccggcatcgacacctaaggtgtggcgc<br>cgtacggggattggttattcatc |
| 18 | Avian orthoreovirus<br>strain S1133 segment<br>S2 (KF741763) | gctttttctcccacgatggcgcgtgccatatacgacttcttttcaacgcctttcgggaat<br>cgtggtctagcgacgaatcgtactcaactgtcatcactactatcgagctcgaattcccca<br>tggcaacggtttctatcatcaatgactccattgacagcgccaggtatcgtttcaacgcct<br>gaagcacccatccaggtcgttgatgtatcaagagtctatgctccacagtgctactgtc<br>cctggagtactcggtagtcgtgatgcttggcgtacatttaatgtcttcgggcttcgtgg<br>actgatgaaggattgtcaggactagtagctgcccaagatcctcccctgccgccccgtat<br>cagccagcctctgctcagtggtcggatctcctcaactaccctagatgggcaaacagacgt |

TABLE 2-continued

Nucleotide Sequence Listings

| SEQ NO. | Sequence Description | Nucleotide Sequence |
| --- | --- | --- |
| | | cgtgagctgcaatctaaatacccacttctgcttcggtccacgctgctttctgccatgcga gctggtcctgttctctacgttgagacgtggccgaatatgatctcaggacgattagctgac tggttcatgtcccaatatggcaacaatttcgttgacatgtgcgcaggttgacccagtct tgttcgaacatgcctgttgagcctgatggaaattatgatcagcagatgcgtgctttaatt agtttgtggcttctttcatacattggggtggtcaatcagaccaacaccatcagcggcttc tacttctcctcgaagactcggggtcaagcgttggacagttggactttattctacactaca aacactaatcgtgttcaaattacgcagaggcatttcgcttacgtgtgtgctcggtctccc gactggaacgtggataaatcatggatcgctgcagcgaacttaaccgctatcgtcatggct tgccgtcaaccgccggtgttcgccaatcaaggcgttattaaccaagcgcagaaccgacct ggcttttccatgaatggggggacgcccgtccatgagctcaacttactgactaccgcgcag gaatgtattcggcagtgggtgatggccggtttggtgtcagcagcgaaggggcaagcctta acgcaggaggctaatgacttctcaaacctcatccaggcggatctaggacaaatcaaagcg caggatgatgctctgtacaaccagcagccagggtacgcgaggagaataaaaacccttcgtt aacggtgactggacaccaggtatgaccgcgcaagtctggccgttctagccactttttacc gcctaggcgtagggtcgtacgctgcccgagtccagccctccggcagcacgtggatgtatt catc |
| 19 | Avian orthoreovirus strain S1133 segment S3 (KF741764) | gcttttgagtccttagcgtgcaagccgcaatggaggtacgtgtgccaaactttcactcg ttcgttgaaggaataacatctagctatttgaagactcctgcttgctggaatgcacagaca gcctgggacactgtgacttttcacgtccctgatgtaattagagttggcaatgcgtattgt tgctctcaatgttgtggtgtactttattacgggactctgccccgcggatgaaattacttc cctcatcacaaatgccatcagcaacagtacaggaccgataccccactgctccggtatgtg cgaattggcagaacgactgagcatctgttggaccaatatgctgttgcgctggagtctatt gctgatcactatgatgaaatcagtcaacgcatggtcgatgagccagagaacgatgaagtc gcgcccttgacattgtaacgcgtactgaatctatccgaagtgataagacggttgacccg gactttggacttaccgcttgagcgacgttctgatgattctcgtcgtagacatcgccgca tcatgctggagaatgattgatgcatcatcacgtagtctcactcttccaaattgtcttgtg tccccgtctttgcattctcgttccgtctttggtcaaatgcaaacgaccaccaccatatac gatgttgcggcgtcgggaaaggccgttaaatttttctccgatggtggctacactatcgcaa cgtgatgctggccctgtaaagcttgcgaatgctgaccagcggaaggtgtatattcattt tggacgtcgcacttcgccttctcaccgctcattggtggagttgggattacgggacagtac gctcgtgagtcataccatcacgtgggtcatccagtcgattgggagtggtaagaaggcgtca cactacaaaaatctgtttatggaatcatggcgtgggtggtcaaagtcagctttcgcatgc gctacaggaatggagccagctgaatgtgaatctcgtctgagggggacatgctcgcactatg cttggacgctctctgccgaacgtctgtgacgacgaggttgctcagcagtctggcgccgtg ctaacgtccctgcagaagactaccaagttcactgttgtggagtgtggttggtaagtacct ccgggtcaaaatgcacataggctcccacctatgtgacggttagcgggactcgccattca tc |
| 20 | Avian orthoreovirus strain S1133 segment S4 (KF741765) | gcttttgagtccttgtgcagccatggacaacaccgtgcgtgttggagtttcccgcaaca catccggcgcagctggtcagacactctttagaaacttctatttactacgatgtaatattt cagctgatggccgtaatgcaacgaaggcggtacaatcccacttccattcctttcacgtg ctgtgcgatgcctatcgcctcttgccgctcactgtgctgatagaaccccttcgccgtgaca acgtgaaacagattcttactcgtgaactgccattttcctcggatctaatcaactacgcac accatgtcaattcatcatccccttactacctctcaaggcgtcgaagcggctcgtttggtag ctcaagtttatggggaacaagtaccgttcgatcacatttatcctactggttcagcgacat actgtcctggtgcaatcgcaaatgctatttctcgcattatggctggctttgtacctcgtg aaggtgatgactttgctccgagtggccctattgactacctcgctgctgacctgatcgcgt ataagtttgtgctcccttacatgcttgacatggtagatggtcgtcctcagattgtcctgc cgtctctcataccgtagaagaaatgttgaccaacaccagcttgctgaactcgattgatgctt catttggtatcgaagcgcgcagtgatcaaaggatgactcgtgatgctgctgagatgagtt ctcgctccctcaatgaacttgaggatcatgatcagagaggtcgtatgccttggaagatca tgctagcgatgatggcggcccaattgaaggttgagttggacgcgctggcggacgagcgta cggagtcacaagctaatgctcacgttacatccttcggatcccgtttatttaatcagatgt cggcgtttgttactattgatcgtgaactgatggaactggccctctctcatcaaggaacagg gcttcgccatgaatccgggtcagattgcatctaagtggtcgctgatacgtcgttccggtc ctactcgtccacttctcaggtgcccgtcttgaaatcaggaatggtaattggatgatccgtg agggtgaccaaacgctactgtctgtctctccagctaggatggcgtagacgggacccatgg tgcgggtgaggggtcgccacacctctgccgcgacttggactcttattcatc |
| 21 | Avian orthoreovirus strain 1733 segment 11 (KF741706) | gcttttttctccgaacgccgaaatgagttcgcgcaaagtggctagacgtcgtcataaggat gctactgaatctaaggacactaaagacactaataaatctaagccatcttctattgatgct aaagaatctacggatcgctacggataagaaagtgctgctccaccaccaaataatccg gctgcttctactccctcctccactgatggggcttcccaaacatctgtcgctaagcagacg aatgataatgacgcctcagttaaggaatcagctcccaagcctactgtctccagcgacggg aaagatgggatgcacgtgctgtgaagtcgcaagacgctaaggctaccgtagctgtagat aataataaggatagagatgtagtatttggtggtgcaggttctggtgacaaaaatgctatc acgaaaactggctccgttgacaatgatgggggtgttaaggtcgttccagccaaggatgct acgatatcttcggccaaagccatgatggagcaaaagcagttagtcgctggtcttccgaaa caaccgaagtctgctaatcatctgtgtaccgtctgcatggctcagtttgcgtcagctgac gctcttactattcaccaaaactacgcattctattgttccaacgcggctctgacgagtttt tcgatctctactgctgttgaagaattcattcaatcatgggctgctgccacatccacggct aacaccaagacggctttgactgtgtctgacgttgactcactgatgatgactgaaggaata cgccttataacttgggattctgggttatgcacgtcttttgagcttgtcccgatcgtccat tcaaacactgttcaagatgttatttcatattcatggtttacgtcaagctataacatcacg actccctccacaagcgactgtcgtgcgattgtcttgcgtactaactgggctgccaaa |

TABLE 2-continued

Nucleotide Sequence Listings

| SEQ NO. | Sequence Description | Nucleotide Sequence |
| --- | --- | --- |
|  |  | ttggattctccctcttcgtcgcgtgaatgtgatcttcgtcttgctccacctacagagagc<br>aatgctcgatcattctcaatgctactcaatacgggtgcgactccagaaggcactttcaac<br>cccaacaccccttcgtatgaacgtgctgcagatgtgtcttcagtatgttctagctaacttg<br>cacctgaaccgtagcactcagtttaccatggatttgactgccgcggctcccaatctatct<br>gcgtctcaactccgtatcgttccagaggataaggagggtaaatggtttcctgtcatgtat<br>ccatcccgagtgaacatcccactgttcaacaagacggctgattttgttaatcagtgcatt<br>cgtgatagagttggtcgatacgatcgcgcccagacttttgctggtgcaccttctgaatgg<br>gctgacatgtgggaaacagcagacgcgttaactctctccgtccgtgaaatgtggatgtca<br>cgcatttctcaaatgaacattactcccgctgatattgctgacgctatctccagatgttct<br>cagtcttgctcactgttgccgcgccgacagctccttctgtggctcgtttgttaccttgg<br>cgggttagttctgatgagaggcagctgctccaactgctgatgtacttaaatgttggtact<br>agtgctgactacgttcaaccgattcttctgcgttcgctcgaactctgtctcgtgtgtca<br>ccactgcgaattaatcctaccctaatcgctaatgctatgtcgacaattgtcgagagcact<br>actaatactcagagtcctgctgcggctatcttgtcaaagcttaaacctgtcgcatctgat<br>ttttccgactttaggttggcatgtgccgcttggttatataatggttgtgtccagacatac<br>ttgtctgaggattcgtatccgagcagcggtgggtctgtcactagcatcgacacgttgatt<br>gatatgtttgtgtgtttgctggcgttgcctctggttactgatcctaacgctccttgtcaa<br>gcctttatggttgtcgctaatgctatggttggttacgagaacctgcctatggacgaccct<br>aatttttactcagcagagactggctgcagcgttcaataatcctactacctggcctcaatgc<br>ttcctccaccctcaaaatattgatcggcgccagtgtccgattctttcatggtgggctcag<br>cagattcatcgtaattggcctacaccatctcagattacttatggtgcgcctgatatcatc<br>ggctccgctaacttgttcactcccctgatgtgttgctgcttccattacaacataggccc<br>atccgtatcaccaatcccaccctgaacttcgataatgagttgacgacttggcgtaacacc<br>gtggttgatttagtcctgcgcattattgacagtggtcggtaccagcctaattggaatcag<br>tctattcgtgcgtctatgcggaatgcgatgacgaatttcaggattattaagtcctataca<br>cctgcttacatagcggaattgctacctgtggaactggcggctatcgctccaactctaccc<br>ttccagcctttccaggtgccgtttgctcgcttagatcgtgacgctatcgtcacccatgtc<br>aatgtgtccagacaagctcccaacaatcttgctcaacctgcattgaacatgtccatgacg<br>taccagcgcacaggagttccaatctctcttagtgcccgtcccttggccgtcgctctttta<br>tcaggtcagtatcctactgatcctcctcttcagaccaatgtttggtacgtgaacactctc<br>acacctctatattccaatgatggtctctttaacaacgtgcagcatgctatggttgcttct<br>gaagcttacgcaactttgatcactatgctggctcagtgcactgacatgcagtaccccgtg<br>gatcggccattgaactggcttcgtcagattaatttggctgccaatgaagcgacgattttt<br>ggtcgctcaattaactcactttttccaaaccgcttttgacctctcaccctctactgtgttg<br>cttcagcctttcttggagtctgatccacgtgcaacgcagctcgccatttcttacgtccgt<br>tataatggtgatagtgagaccttcgtgccaacagtgcgtccgtctatgatctcagaggcg<br>acattgctcgttgagcgtactctctcgcacgaatacaaccttttcggtttatgtcgcggt<br>gacatcattctggggcagcacatgactcctactgcgttcaatcctctgctccgcctccc<br>tctgtcattttttaatagggggtgatgctgacgtttatgagtttggcccacgtagcttcgcc<br>aacttcggtatgaatggggaggagatcttggtcatggatgcgaacggcgtgcgtcgtcca<br>ttacttggccgttgggttatgccactgcagcttctgatggtgaatattggcgtctttccc<br>aagttgttgttggatcgtatcttgaagggacgcttatacatccgacttgaagttggcgcg<br>tatccctacactgtgcagtattaccagggacgtgagttcacagatggttcactctgctt<br>gagcaatggatgtctaaggtgtcacccatgggtatccctcccgtccctttcctcatgcca<br>cagtccgaaggacacaacatcacttcaggcatggttactcattacatctggtccactgaa<br>tacaatgacgggtcactcttcgccacgaacactgacctgccggttactgtgtttggtcct<br>gaccgtaccatcccaatcgaacgctaccgggcactcgttgatccaggcgctcttcctgct<br>accaaccaactgccgcacaccatcgacctttactgctcactgagacggtattatctggaa<br>acacctcctatcaccgctactgttaccacttatggcgatggactccccgcgctgaaccat<br>tagagcggcgaggctagacgcgagttgatcgcgtcgactctcgttggagattattcatc |
| 22 | Avian orthoreovirus strain 1733 segment 12 (KF741707) | gcttttttcctcaccatgcatgtcaacgggtttgatgatgctactctctcttacgcacaat<br>ccatctcgggggttattccaatgacaaataagttatttgagcaagcatctgcatcgatac<br>gtgccttaccgcgctcacacgtttatgctctattagatgatgtgaatttttctgttacat<br>gtgtgatcccgaatcgcatcttccatcaccctgatcactctgagtattttttatgttgatg<br>cagttaatagggttagacgaaaacaagttatcgatcctgatgatgtattcgttccaaatt<br>gtaacctgcagggtcttatcactccaatggagaggttaccaaattatggtcagttgtctg<br>agattatttcatcgaacgctcgggatggcttgccatctgcacgcatagcagctacattt<br>ataacatttcggtatctcaggctcgtcaagttaaagctccacttgaatcattttttgttac<br>ctttgctgttatctgaaacctgccattatcggatgatccttgcggatttgacaccacag<br>cttctccccaatccatgcaaatctggcgttatgggtgctacgtgaaatcagtcggacta<br>tttgtggatcctcgaaagaccgttcaccctggttattgcttgattcaggggtcgcgtggt<br>tcatgtctccgttaatgtcatcagccattccgcctctcatggctgacttaacgaatctag<br>caatctataaacaaatttgttctgtgtcggacgagcttcattctcttgcggttcaagtgg<br>tgttgcaggctgcagcgtcacaatcatatggccactacatattgcagacgaagtcaatat<br>ttccccagaatacattgcataacatgtttcgtacactcaccgatggcatcgttccggtta<br>tagattggctggaaccgcgttctaactatcgctttatgcttcaaggtgcgcgtaaagtga<br>cttcagacgatgcgaatcaagctccggataacacagacgctgccgagcaacttggccgta<br>gaatgggtgccttgatgtcgtacgctctctacgcaagatgtcttcatctatcactgtcc<br>attcacacgatgctatgaccttgtacgtgatgctatgtcgtgcactagtggcatattta<br>ttacgcgacaacctactgagactgttttaaaagagtacacgccctaccattgaag<br>ttcctattccacagtcagattggtcaccgccattggatcttgcgatatctctcggatg<br>cctgctctctcccgctgtatatttggctagggcttggcgaagagctgcttctgctgtag<br>tggataaccacgtacctgggaccctttatatcaggccatccttcgctctcagtatgtga<br>cgtcacgtggtgggtctggtgctgcgttaagagatgctttgaaggctgcagaagttgaac<br>ttcctcagtatcctgggggtcagtgttaaggtggcgaccaagatttatcaggcggctcaga |

TABLE 2-continued

Nucleotide Sequence Listings

| SEQ NO. | Sequence Description | Nucleotide Sequence |
|---|---|---|
| | | ctgcggacgtaccttttgacaagttatctcgggctgttctagctccgttgtcgatgggct
tacgtaaccaagttcagcgacgtccaaggaccattatgcctatgaatgtcgttcaacagc
agatctcagcggctcacactctctccgctgactacatcaattatcacatgaacttatcga
cgacatcgggtagcgctgttattgagaaggtggttccattaggtatgtatgcgtcctgtc
cccctgctcaagcggttaacattgatatcaaagcttgtgacgcgtctatcacgtaccagt
attttctttccgttatagtcggtgctattcatgagggtgcagcaggccgccgcgtctcgt
cctcattcatgggagttccaccaagtgtgctatctgttgttgatgctagcggagtaacgt
cctcaatgcctatctcaggtttccaggttatgtgtcagtggttggctaagctctaccagc
gaggttttgagtatcaagtaacggacacgttctcgccaggcaatattttcactcatcata
ccactacttttccctctggctcaacagcgacgtctacagaacatactgcaaataatagta
cgatgatggatggatttttgcgtgcttggattccttcctccggtgcgtctgatgtgctga
agaagttctgcaaatccatttcaatacaacggaattacgtttgtcagggtgacgacggtt
taatggtcgttgatgggctatcaacaggtaaattatcaggcggagataatcgatgaattcg
tcaaagagttgagagcctatggtaaatcgtttgggtggaactacgacatagagtttaccg
gaaatgctgagtacctaaaattatatttcctaaatggttgccgtataccgaatgtttctc
ggcatccgatctgtggcaaagagcgcgcttcaggggataagttagaaatgtggccatcca
ctattgacatcttcaatgcatattttgtgaacggtgtgcatgatggtttaccgtggcgca
gatggttgcgttattgttgggctctcgctctcatgtgttctgggaaaaccgtacgtcacg
acgattctgaggtgctgatccaatacctatgtggtccttttgtgtattgggtttgcctc
ccgtgagtgcgtttgggtctgatccatggatcttttctccatacatgcccactggtgatc
atggttttactcaatgttaacttagtgcgtcctctgatcactaacttgtccccgtctt
cagacacttcaggattatttggtcaatgtgatcataacgtcttgttcaactctgagctgg
tttatcagggctattacatggctcaatgcccacggcaaccctctcgttcgaatcgtaggg
atgatcctgactctgtacagcgtttcgttaaggctttagagtcttatctttatatttccc
ctgagctaaagtctcgagtgcgacttggtcgcgaccgatggcaaaagttggttgggtata
cagaaaaatctcctccgtcgcttgatgacgtggctttcaaatggttccggagtgcacagg
aagctgatcttccaactgctacagagattcaaagcatggatctggctttactggcagcca
gacgtcggacgtatcaaggtttctccaagttgttaaacacctacttgagggtgacttggg
atttatctgatcctgttgaacacgctgtagatcctcgtgttcccttgtgtgctggtgttt
ctccatcgaatagcgaaccgtttcttaaactgtactccgttggtccaatgatgcaatcta
cgcgtaaatatttcagcaatacgctattcatccatcggactgtgtctggtcttgacgtcg
atgtcgttgatcgtgcgcttcttaggttgcgtgctcttaatgcgcctgatgatgtggttg
tggctcaacttttgatggtaggggttgtctgaagccgaagctgctacgttggcagcgaaaa
tacggacgatggatattaacgccgtgcaattggccagagttgttaatctatctattcctg
actcgtggatgaccatggacttcgatcgcttgatacgagatatcgtatctatcactcctc
taaccgtccggtccctaaccaccgatctaccctctggtgtgccgtgggctcgcgcgatac
tgcagttcctaggtgcgggtgttgctatgacggctgttggaccctcgcgtcgtccttact
tgcactcagttgctggaggtatgtcctcatttattaagcagttccgccggtggatgcgtg
ccgaaacgaggtagcgtccgtgctcggcatggctcgaggaattactcatc |
| 23 | Avian orthoreovirus strain 1733 segment 13 (KF741708) | gcttttccacccatggctcagattcgaggccttcggttgtctacgacactctcagctcca
ccaccaagaaagattgtaacctcgcatacgtatgatgaactaatctccgctttaaagctg
acaaccaaaccttggcgctcttttaaaatcacgcggcaatgactcaatcacagcagtccgg
cttctatttcccctaatggttacattgagcccatgcttatgttagagaaggacatgaca
tacgatgcttttgagtcttggattacgcccctctttctgctctagctgaccagttgctt
agacactacctattgctgcttatcacggcgggttgattaaccgttgttaaccaatgct
gttgttgccgctttcttatcgaatgtgccctatgcgcatgcattggatcatctttttctg
gttcgtgggaacgttgaggatattatggatgcaggaatcacaattcagaatcatttatgg
tttgaccgtggtgctatagtaactccggccgggcagaagtttgttcagttgactggctat
aattttttcatccaatgatccgtgcttattttctaagcaattgcgttgttatggtcttgtt
tactattttcttaacatgtccgattgtctgacgtactgttggcgtcatctctctaactcg
actcctctgatacattttgatcgtccgtccaacgggattcattgcttggtgccctccgaa
tccacgacacctatcgccggttcattacctgtgtcagctctcagctccattctgctggag
tcttgtcttcagcaatcctcacttaatgctcttactcctactggctcaccagtcgttagg
caggtggaggtgttgctacctctatcgtcaccattttcgaacgtcaaaatactctggaa
tattctcttttttgctcttcgaatgctctgattaatggttatcaattcgttgatttacgt
cccggacatccagattgcgctaccgttgctgctgttttagctaggttaactgatttctcg
aaaggtatcactgttattcaaccacgccctgctctttcactgttaatcatgatagtcct
ctgacgtacagtggagagaatgctaatttcatccaacgcttagcttctatgtctggaaga
tctattggtcccgtcgttattgggaaatctgtcgatcatgccgtcggttggatgcctcag
tttgatccgctacatcgtacaatcctgatttatcattagattcactctcacgagctacg
acactgccactccgtgctaagtattctactttctggtctggccccgcgctcttttcctt
gcttcgtgtgacaggcacaatggcgtgtatgacattcagttcatggcccaatttcctcct
acgtatttcagcgatgatgatgccttttctaggtcaaggttttcttcctatcgtgctgtt
aaagatcgatcgttgttaaaagatactgccaatctgatgtacatttcaaacttatcgagc
tcgcatgaccatcgtcttgtccctgattctaagaccatgatttacgtagggtcttccggt
acgcatgcagataaccaaccttccattattaaacctctttttagctgggtctcttccaggt
gttttccgcccctatccgtgaagcagattggttgggaggttactaacgggactatttgt
gacattgagctgcctttagctaccggcacattcttcttcgtgtacagtgacgtagaccag
gttcagtcaggcgattccgacctagacgcttcctcccgacgcttttgctctcaattggat
atgttaatgaaattgacgtttactggcggttccttagttgtcaagtgcaattttccgact
aacttggtttggcgtcatatctttttctaccatttctccctattctcgtccattcatctg
atgaagcctcttgtgtcgaataatttggagttgtacttattatttgcagagcgttgcct
gtccctgatgccgcattccgtccgtcggcggatgttgtcgttttctggcgatctcaactg
caacgctaccgggtattgcgcgactcattctctaatgtaccctctatcggctctactctt
accttagatgactcattgactgtatctgttctgaattttgtcgatgtcacttccctttcc |

TABLE 2-continued

Nucleotide Sequence Listings

| SEQ NO. | Sequence Description | Nucleotide Sequence |
|---|---|---|
| | | tccattgaggatcaacgagctttatccgctttctcagtccttacctccttggggtctcag aagttatcgcttcatccctactttgatagttatcgcacacagctcactggaataatcact ccccattctcgtaacatcttaaatagattagcgtacgtcccgcgtgtcttcccttcaacg atcgacgttcaacatcgtgtcatggctgcctcagatcccgagattttggttttcgctcc aattcgtggactcaattgtccttttctacgatgctacgttgactgcgacggattttact gatgtgaagcattggttggatctgggaactggacccgaagcgcgaccgttgtcttttctg ccgactgatcttcctgtcacattgtgcgacactcggcctttCgttttccgtctggctgt tgggccacgttcactgacttcttaagttatgattacctcgttacgaacgtcgttttatca actggtgccgatgttgtgtcctgcattctctccctagggcagcctgcgctgacgctaac atgactctacatgagggcgtgcgtcaactaatttcccagtgcgtagatgctagtgttaaa acgctgtttttgcagcttaattgtccccttccatcagcgggtgatgtgtctcgggagatc ctcgagttggttcagactaattcaacatacgtattccataccttaggtcgcattgagccg ttcatcccatattccgctctcttggaaatagtcgaggattttgtgccctggcatcgtcgtt gagattaaaacgatggattcttctctttcatggcttgactacgctgttcaatctaatgca tcagtgacgtcggacgacattgtcttagcgatgcgtttgtctcacttctgtcctcttttt gtgtttcattttgaccgtcattctgctcaattcccggaagatgcgcgtgttggtgctccc ttcaccgtcacactgttggattatgaagatactcgatcatatgaggtgactttagacaat gtcactattgctactattactgcaggcgctctggtcggattttcatctggtgtaagtgtc acctcatccaacaatcagctggttatgactattgatcctgcgagtccaggaattctttct gtcattcaggtactcccgctcgcatctcattaggcagctgcgtgatagaggcgccggac ccatcccttctctgattttttcctgctacattagatacttccttgtcagggaccgacctg gagttacgtctgtctgactggtatgacgtcgctctcttctacgtcgacgaagcgcactct cgactgctgcccgtatccgataccaagtacgagatttatcgtaaggatcaagcgccgaat agtcgagtaatcaactatatctttgatcgttctgacgtgttctttaaattggtgctgtgc gacgtctctccatctgaataggtcgcttcatctatcgtgagttaccggagctaagttcc cctgtatggcctgatgatgcgcgtacttttcttatccataccattttgaatccccatggtg attgtatcgccggacggacccgttaactatgacggtgccaatttcactcctccaacttca tggcttacagttgacggcagcacctgcgtcatagatggccgtccctcatttttacgtgccc cctggccgatatggtctggtgagagtctaaacgaccgcgggcctccagtaaaagggtgtt attcatc |
| 24 | Avian orthoreovirus strain 1733 segment M1 (KF741709) | gcttttctcgacatggcctctctagccacacctgtgctaggagtcggttctcgtattacc gccttagatcgtactattgatgccatcacgttgaaacctcgaatcgacctccaagatgtg tacacaattgatcctacacctgactctgcgccagatagagtttaatctcttcgggcacttca atggacgacattgctcgtggattgttgcatcgggactggcgtcgtcaatctaccatcatc ttgcttccttctcgtcgttctcttcttgagtacctattgtcaaatccttctgtctgtcca gacggtttagatcgttctcgacttaaaggattccaaaagcgtccaaacgattttcgtgtt caagacttctttttccactgattacggattcaacgtcaattgctacatattctcggtgg cttaatgctcatccctattgtgtactactactacttacaaggtcgctggcgctcgggtgcgt ctctttggacctgccaaattgtacattctgtcgcctgatgttcttcgtgaattatccatt ttgaaatccactgatcgcatcttcgttgtacctacagcacgtgtatatgtcggttgtttt cctagcgcttctactagcaattgtgtcctactgcacgcgaacgctggaatgccccctgac gttcatcccgtCgtaaaagcaatccaattagcctatgaccatcaatatcgtgtcactgct cgttatctctcagaccctcttatctcagctcttcttcttgggaaccggtcggtgaagacg ttgaaggtacagccagtagaagccagagcagcacggtcagttggcatccgcgttcaagcg atgacacctcctcgtggtatcaacacatcaatcatccaggtcgttgatcttaagttgcaa tgtcggcattccctcattcccaccgaaaggccattcccactaacgtttatcggcctccca tcctgtttgcttcaacatttggatctaacattatctgatgattgggtgcccattcgtgat catacaggtatgtttgaaatgtggtttatgattcttacgctcacttgtgacaagatcctt gatgacgggggaacgctgttttttctcattcccagttctactaatgcactatcagttaat tatgtacagctcacgtcaactgtatccccacgtcctcagtcactggcggctaatgcgtcc gggcggatagattccattggactgtgtatgcctaaaggttctttcaagtcaactatgatt aaatttctcactggattggagatttgtggtacgcgagtaatgtattcagacgtcgtgatg gacagtgatgatgtgggtgatgctttggatcccacttttgagaccgcactatatgacgca ctgttggctcttgatccgcccttgacgttgataagttggctagtcccaccgatttagtt gatcaggagtatgtcgcatctcacatgtacccaacatttttacggcttgtcaatgagttg ctaacgcctaaagcttcagaattatactcagagcgtagtgtggagtttcggtctcttact tacgcgcatgctgactctgaatttcttaacgcttgctggaccgctcgcttgatgcgctgc ttcatcaactatcacgaagagcagaatatcctactccgtcctggacgcgttggtggtgtg ctattccaggtcgcgttgagtcgctgctacaagatgtttgctacttctactcctgcttcc cctctgtcattgttcctcaagtcgttgtttgttccttggattgaatctgcacctttgtta gcgagtctgacgccgaacgagtcctctcgtgtgttagcatggtatattccttcctcgtac tggagtgacaatggctggtgcacactcatcgtcacgtcaccttctctttcatt cgcggtcttccagcagacctatcggtgttagatctgtttgactggtctcgattccgcgcg actataaacgtagacacgtctctagtcgagctaggcgctgacattcgtgcggttaaggtg tcggttcattggacatcccagaagcccactgtggacgtctttgacaatcgcgcgcttttc actccctttccagcactaccacttgagtctccattgtaattgcgcgcctggtcgcccttt ttcgcaaaaaatatgaaactgtatctgtcgacggttggaggcgagcactgacgggccgtg gggcggtgacacccaggggggatgtgtggtaaccctgggttagtcgtcttgagatattc atc |
| 25 | Avian orthoreovirus strain 1733 segment M2 (KF741710) | gcttttttcagtgccagtctttctcacaaaatgggcaacgcaacgtctgtcgtgcagaact ttaacatccaaggtgatggcaatcattttgccccatccgctgagactacttcatccgcag taccctcgttatctctgaatcctggactgttgaatccaggtggtaaggcgtgggttctga ttgactcatcgctaaatgcttcggatccttcatcattaagattgatgacttcggctgatc tatcgacgctctctcagtcggctattggtaattctactgggtttcttcccacctccggta |

TABLE 2-continued

Nucleotide Sequence Listings

| SEQ NO. | Sequence Description | Nucleotide Sequence |
| --- | --- | --- |
|  |  | tgtacgccgtgactgctaaagagacgttaagtgtaataactgagcatgcaatttcccagt ttgataagttgcaaatggcctgtgagttggaccgtgattacctggatgccagaggcgttt ctcccgagtccgtgaatattcataattacatcgtctatgttgattgttttgtgggtgtgt ccgcgaggcaggccgcgtcgaatttcagacagcacgtgcccgttatcacaaaatctcgta tgacacaattcatgacatctgctcagaacgtgttacaagtgctcggaccttgggaacgtg acgttcgtgaactactcactattcttcccacttctactaccgctggcaagatcacatgcg acatgaggtctgttgtcactttcattgatgatcagctttccgacaccagtttatgccgta tgtaccctgaatgtgctgctgcggcggtggccagacgtaatggtggcatccgatggaaga cacctgagaccgacgaggctccttcacttgctactaatgacattgctgcctcgaccatgg gtgcacttgcaaataccacgccgttagctgagaaatcggattctggtgaggaatcaatgc gcttggtgaatgatgttggcgtcgatatcgtttgttcccgggccccgattagctcctcgg tctggtcacgtacagttgaaccgagatcatacaacattagaacacttcgcgtagaagaag ctctctggttgcgtgacgtgtcaggcaactactggctttgacgtgcagtacacgctccctg accaggctactcataaacatttctggctccagaaggggtcagttgtcattaatctagagc aaacgggcagcatgatgtttgatgtaaacatagcaggtaaagattacaagaagggcactt ttaatcctgataatcgtaaactagttcttctggttatgcagtcgaaaatacctttgaat cttggactgtcgcttctcagatcactggtatcgcccaagtggctgaagtcactgtgcacg ccgctgatagctcgactcccaaccaaaagataattggtgagacttcgctgtcgtatctgt tgagagagagacagtgaccacgtccgataccgaaatcaatacatacctactgtgcactt ggcaacttgacgataaacaaagcaatgacgcaaatgtctggccagatgcatgggatggaa ttacaacattgacgccactcacttctgtaccgtaactattaaggggacttcggtggact ctgtcgtaccgtctgatctcgttggcgcttatactcctgagtccttggccgctgcactcc ctaatgatgctggtttgatcttggctaacaaagcaactaaactggctgacgctatcaaga aagaggatgactctgtggtcgatgagtcttctcccttttagcactcctattcaaggggtcc tggccgttcaacaacttgacaccgtagggacacgtggagcacgcgcactccaacctcctt cgattctgaagcgcattgcttcgcgagctcttcacatgttcttgggtgacccgcgttcca ttttgaaacaggcgatacccgtgttgagagaccctgacgtatggactggttttgtccaag gcgttagagatggcattcggactaagtcgttgtccgctggggtgcggtcggtgtacaaca acgttaccgccacgcaatctgtccaaacatggaagcaggggttcctgacaaaaatacaga tgttgttcaaaccatcgtgaggtgctaaggcctctctctacggcgggtcggtgggcacgt cgtggtgatgctgaatgcacggggaggtgacgctccctggattggcacgttattcatc |
| 26 | Avian orthoreovirus strain 1733 segment M3 (KF741711) | gcttttttgagtcctagcgtggatcatggcgtcaaccaagtggggagacaagccgatgtcg ctctcaatgtctcacgatggatcatctatccgcagtgctgcctcacaattcttatcggtt cctctgtctcactcaacgcctatcccacctcaacggaagactgtgctgttgaagttcatg attggtgacgaactggttaccgttcagggtgctctcgctccgttcgacgaatattggtat gacaaccagcccctgttagctcaggctgttgagatgctcgcctctgcagatcgtttgcgt caatttgagcattatgagaaattcctactcaagaaaggtcaccagataactgagatcatg aacaggttacgtctcttttttacggatgttctcaaagttaagatggaagctgacgcttta cccgctttagcccaatatctgatggttggaaccttggaggctgtttccaccgctgattcc cccgatgcctgcgtcccagtcacctcaaagatcttagctaagcagcagactattgctaag tctcctggacgtctcgacgaggaagaatataatgttattcgatcacgtttcctcacgcat gaagtcttcgacttaacgtccgatttacccggagtacaaccgtttatggacatgtactac gccactgtccccgtgctgattctacaggatggtgtgtgtatcgtcgaaagggtttggtt atctacgctcctgatgagcaattctcggatctgactatcttctccacacgtcttactgca tcacgtgagctgcagcttgtggctggagatgttgtcgtagcctgctttgatctcatggac gtctctgacattgctccatctcatcatgcatcagtgcaggaagagcgtactctcgggacc agtaagtattcgaatgtgacggctaatgatcatcctctggtattcttctcacccagtgcg ctccgttgggcaattgaccatgcttgtactgactccttggtttctacccggaatattcgt gtctgcgttggcatcgatcctctggtaactcgatggacccgagatggtgtgcaagaggct gctattctcatggatgacaagctaccctcagcaggtcgtgcgcgtatgcgcgttgcgaaca ttgcttctcgctagacggtctccaatgccatccttcttactcggtgcgctaaaacagtca ggcggtcagttactggagcactaccgatgcgatgcagctaatagatatggatctcccacc gttccgacctcccatccgccaccatgctcaaagtgtcctgagctaaaagaacaaattgcc aagctctcgtcatcgcctatacccaaagtcgattcgtccgttggtccagccgtactgctg tctaaaattgctgaccttcagcgtgctaatagagaactgtcactgaaactggttgatgtt caacctgctcgggaagatcacttgttggcttatctcaatgaacacgtgtgtaaatgct aaagatcatgaaaagggcctgctcgctcgttgtaacgtatctggtgattcaatctcctct atccttggccagcgcatgaagaatcgggaaaaggtttgaaactcgactgcgtcatgaggct agtgctgagtgggaaccccgtgtggaagcgttaaaccaagaattggctaaagctcgtgtc gaacagcaggacatgatgactcaatccctacagtacctgaacgagcgtgatgaactactc caggaagtggatgagcttaagcgtgagctgactacccctgcgttccgctaacgtacgattg aatgctgacaatcatcggatgagtcgtgcgacacgtgtcggagacgccttcgtcagtgac gtcgagccgctaccctctggcataccctggtgaatcgaaaccatctatggaagaattggtg gatgatctgtgagctttgacctgtgactcgacttctctctgattccatgtacccacggcg gactcggttattcatc |
| 27 | Avian orthoreovirus strain 1733 segment S1 (KF741712) | gcttttttcaatcccttgttcgtcgatgctgc

TABLE 2-continued

Nucleotide Sequence Listings

| SEQ NO. | Sequence Description | Nucleotide Sequence |
|---|---|---|
| | | tgagtacgattgtgctctactattctccccacacgctatcgttccattgcctgcatccga tcggcggtcttgtcttatagttcattgggatggcgggtctcaatccatcgcagcgaagag aggtcgtcagcttgatactgtcattgacttcgaacgtgactataagtcatggcgatttga cgccgatctatgaacggctgaccaatctagaagcgtctacggagttattacatcgctcca tttccgatatatccactactgtctcaaatattctgcaaatttacaagacatgacccata tcttggatgatgtaactgctaatttagacggtttgaggaccactgttactgcacttcagg atttcgtctccattctgtctacaaatgtgactgacttaacgaacacatcctctgcgcacg cggcgacactatctttacttcaaactacggttgacggaaactccactgccatctccaatt tgaagagtgatgtatcgtcgaacggtttagctattacagatctgcaggatcgtgttaaat cattggagtctactgcgagtcatggtctatcttttttcgcctccgcttagtgtcgctgacg gcgtggtttcattagacatggaccccctacttctgttctcaacgagtttctttaacatcat actcggcggaggctcaactaatgcaatttcggtggatggcacggggtactaacggatcat ctgataccattgacatgaccgttaacgctcactgtcatgaagacgcactgattatatga tgtcgtccacgggaaatctcacggtcactagtaacgtcgtgttattaaccttcgatttaa gtgacataacgcatatcccatcagacctagcacgtcttgttcccagtgcgggattccaag ctgcgtcgttccctgtggacgtatcattcacccgcgattctgcgactcatgcgtaccaag cgtatggggtgactcgagctcacgtgtcttcacaattactttcccaaccggaggtgatg gtacagcgaacattcgttccttgaccgtgcgtaccggcatcgacacctaaggtgtggcgc cgtacggggattggttattcatc |
| 28 | Avian orthoreovirus strain 1733 segment S2 (KF741713) | gcttttctcccacgatggcgcgtgccatatacgacttcttttctacgcctttcgggaat cgtggtctagcgacgaatcgtactcaactgtcatcactactatcgagctcgaattcccca tggcaacgatttctatcatcaatgactccattgacagcgccaggtatcgtttcaacgcct gaagcacccatccaggttcgttgatgtatcaagagtctatgctccacagtgctactgtc cctggagtactcggtagtcgtgatgcttggcgtacatttaatgtcttcgggctttcgtgg actgatgaaggattgtcaggactagtagctgcccaagatcctcccccgtgccgccccgtat cagccagcctctgctcagtggtcggatctcctcaactaccctagatgggcaaacagacgt cgtgagctgcaatctaaatacccacttctgcttcggtccacgctgctttctgccatgcga gctggtcctgttctctacgttgagacgtggccgaatatgatctcaggacgattagctgat tggttcatgtcccaatatggcaacaatttcgttgacatgtgcgccaggttgacccagtct tgttcgaacatgcctgttgagcctgatggaaattatgatcagcagatgcgtgatttaatt agtttgtggcttctttcatacattgggtggtcaatcagaccaacaccatcagcggcttc tacttctcctcgaagactcggggtcaagcgttggacagttggactttattctacactaca aacactaatcgtgttcaaattacgcagaggcattcgcttacgtgtgtgctcggtctccc gactggaacgtggataaatcatggatcgctgcagcgaacttaaccgctatcgtcatggct tgccgtcaaccgccggtgttcgccaatcaaggcgttattaaccaagcgcagaaccgacct ggcttttccatgaatgggggacgcccgtccatgagctcaacttactgactaccgcgcag gaatgtattcggcagtgggtgatgccggtttggtgtcggcagcgaagggcgaagcctta acgcaggaggctaatgacttctcgaacctcatccaggcggatctaggacaaatcaaagcg caggatgatgctctgtacaaccagcagccagggtacgcgaggagaataaaaccttcgtt aacggtgactggacaccaggtatgaccgcgcaagctctggccgttctagccacttttacc gcctaggcgtagggtcgtacgctgcccgagtccagccctccggcagcacgtggatgtatt catc |
| 29 | Avian orthoreovirus strain 1733 segment S3 (KF741714) | gcttttgagtccttagcgtgcaagcc TABLE 2-continued Nucleotide Sequence Listings

| SEQ NO. | Sequence Description | Nucleotide Sequence |
|---|---|---|
| | | cgtctcataccgtagaagaaatgttgaccaacaccagcttgctgaactcgattgatgctt<br>catttggtatcgaagcgcgcagtgatcaaaggatgactcgtgatgctgctgagatgagtt<br>ctcgctccctcaatgaacttgaggatcatgatcagagaggtcgtatgccttggaagatca<br>tgctagcgatgatggcggcccaattgaaggttgagttggacgcgctggcggacgagcgta<br>cggagtcacaagctaatgctcacgttacatccttcggatcccgtttatttaatcagatgt<br>cggcgttcgttactattgatcgtgaactgatggaactggcccttctcatcaaggaacagg<br>gcttcgccatgaatccgggtcagattgcatctaagtggtcgctgatacgtcgttccggtc<br>ctactcgtccactttcaggtgcccgtcttgaaatcaggaatggtaattggatgatccgtg<br>agggtgaccaaacgctactgtctgtctctccagctaggatggcgtagacgggacccatgg<br>tgcgggtgaggggtcgccacaccctctgccgcgacttggactcttattcatc |

The invention claimed is:

1. An oncolytic agent comprising a modified avian-virus that has an increased oncolytic activity as compared to a non-avian, oncolytic-virus based agent from the same group, wherein the modified avian virus is an avian reovirus with a nucleotide sequence that comprises SEQ NO. 1, SEQ NO. 2, SEQ NO. 3, SEQ NO. 4, SEQ NO. 5, SEQ NO. 6, SEQ NO. 7, SEQ NO. 8, SEQ NO. 9 and SEQ NO. 10.

2. The oncolytic agent of claim 1, wherein the modified avian-virus exhibits oncolysis at lower multiplicity of infections (MOIs) than a non-avian oncolytic-virus based agent from the same group.

3. The oncolytic agent of claim 1, wherein the modified avian-virus exhibits oncolysis at higher temperatures than a non-avian oncolytic-virus based agent from the same group.

4. The oncolytic agent of claim 1, where the modified avian virus is one of an avian pox virus, an avian reovirus, a Newcastle's disease virus, a duck hepatitis virus, an infectious bursal disease virus, a chicken parvovirus and a combination thereof.

5. A method of making an agent/target cell complex, the method comprising a step of administering a therapeutically effective amount of an oncolytic agent to a subject, wherein the oncolytic agent comprises a modified avian virus that has an increased oncolytic activity as compared to an non-avian oncolytic virus-agent from the same group, and wherein the target cell is a cancer cell and wherein the modified avian virus is an avian reovirus with a nucleotide sequence that comprises SEQ NO. 1, SEQ NO. 2, SEQ NO. 3, SEQ NO. 4, SEQ NO. 5, SEQ NO. 6, SEQ NO. 7, SEQ NO. 8, SEQ NO. 9 and SEQ NO. 10.

* * * * *

SEQUENCE LISTING

<160> NUMBER OF SEQ ID NOS: 30

<210> SEQ ID NO 1
<211> LENGTH: 3959
<212> TYPE: DNA
<213> ORGANISM: Artificial Sequence
<220> FEATURE:
<223> OTHER INFORMATION: Synthetic Sequence

<400> SEQUENCE: 1

```
gcttttctc  cgaacgccga  aatgagttcg  cgcaaagtgg  ctagacgtcg  tcataaggat     60
gctactgaat  ctaaagacac  taagaacact  actaagtcta  agccttcttc  cgctgacgtt    120
aaagaatctg  tagacaacgc  cacagacaaa  aaagtgaccg  tcccaacgcc  agataatcca    180
gctgcctcta  ctccctcctc  tactgatggg  gcttcacaaa  cctcagtcgc  taagcagacg    240
aatgataatg  ataactcagt  taaggaatcg  gctcccaaac  ctactgtgtc  tagtgatggg    300
aaagatggga  tgcacagtgc  ggtgaagtcg  caagacgcca  aagcgaccac  agctgtagat    360
aataataagg  atagggacgt  agtatttggt  ggtgcgggtt  ctggtgataa  gaatgctatt    420
acgaagactg  ggtctgttga  caatgatgga  ggtgttaagg  ttgttccagc  taaagacgct    480
acgatatctt  cagctaaggc  tatgatggag  caaaaacagc  ttgtagctgg  ccttccgaag    540
caaccgaagt  ccgctaatca  tttgtgtact  gtctgcatgg  cccagttcgc  gtcatctgac    600
gctcttgcta  ttcaccagac  tacgcattct  attggttcca  atgctgctct  gacaagcttt    660
tcgatttcta  ctgctgtcga  agaattcatt  cagtcatggg  ctactgccac  gtctacagcc    720
aacactaaga  cggctttgac  tgtgtctgac  gttgactcac  tgatgatgac  tgaagggata    780
cgcctcataa  cttgggattc  cgggttatgt  acgtctttcg  aacttgtccc  gattgtccat    840
tcaaatactg  ttcaagatgt  tatttcgtat  tcatggttta  cgtcaagcta  taacatcact    900 acccccttc   cacaggcgac  tgtcgtgcga  atcgttttac  gtaccaactg  ggctgctaag    960
ttggattcac  cctcgtcatc  gcgggaatgt  gatcttcgtc  ttgcacctcc  tacggagagt   1020
aacgctagat  cattctcgat  gctactcaac  acgggtgcga  ctccagaagg  cactttcaac   1080
ccaaacaccc  ttcgtatgaa  tgtgctgcag  atgtgtcttc  agtatgtgct  gtctaactta   1140
cacttaaacc  gtagtactca  atttaccatg  gatttgactg  ccgaggctcc  taatctttcc   1200
gcgtctcaac  tccgtattgt  tccagaggat  aaggaggta   aatggttccc  tgtcatgtat   1260
ccatcccgag  tgaacatccc  cttgttcaat  aagactgctg  atttcgtcaa  tcagtgcatt   1320
cgtgatagga  taggccgata  tgatcgtgct  cagactttcg  ctggcgcacc  ttctgaatgg   1380
gctgatatgt  gggagacagc  ggactcgcta  actctttccg  tccgtgaaat  gtggatgtcg   1440
```

```
cgtatttctc agatgaatat cactcccgct gacattgctg acgctatctc cagatgttca    1500
cagtccttgc tcactgtggc tgcacctacg gctccctctg tggctcgctt gttgccttgg    1560
cgtgttagtt ctgatgagag gcagctcctc caattgttaa tgtacctaaa tgttgggacc    1620
agtgccgact acgttcagcc gattctgtct gcgtttgctc ggactctgtc tcgtgtgtca    1680
ccactgcgca ttaatcccac cctgatcgct aacgctatgt cgacgattgt cgagagcact    1740
actaacaccc agagtcctgc cgcggctatc ttgtcaaagc ttaaacctgt ggcctctgat    1800
ttttccgact tcaggttggc gtgtgccgcc tggctatata acggttgcgt tcagacatac    1860
ctatctgagg attcatatcc aagcagtggt gggtctgtca ctagcatcga cacgttggtt    1920
gatatgttcg tgtgtctatt ggcgttacct ttagtcactg atcctaatgc tccgtgccaa    1980
gcctttatgg ttgttgctaa cgccatggtt ggctacgaga atctgcctat ggacgatcct    2040 aatttactc agcagaggtt ggctgcagcg ttcaacaatc ctaccacctg gcctcagtgc    2100
ttccttcacc ctcaaaatat tgatcgtcgc cagtgtccca tcctctcttg gtgggctcaa    2160
caaatccacc gtaattggcc tacaccatct cagattactt acggtgcacc tgatatcatt    2220
ggatccgcca acctgttcac tccccctgat gtgctgctgc ttccattaca acacaggccc    2280
atacgtatta ccaatcccac tttgaacttc gataatgagt tgacgacctg gcgtaacacc    2340
gtggtcgatt tagtcttacg catcatcgac agtggtcggt accagcctaa ttggaatcag    2400
tccattcgcg catccatgcg aaacgcgatg acgaatttca ggattatcaa gtcttacact    2460
cctgcctaca tagcggaact gctgcccgtt gaattggcgg ctatcgcccc aactttaccc    2520
ttccagcctt tccaggtacc gtttgctcgt ttggatcgtg acgctatcgt cactcacgtc    2580
aatgtatctc ggcaagctcc caacaatctt gctcaacctg cgttgaacat gtctatgacg    2640
taccagcgca cgggagttcc aatctctctc agcgcccgtc ccttagcggt cgctcttctg    2700
tcaggccagt accccactga tcctcctctc cagaccaacg tttggtacgt gaacactctc    2760
acacctctgt attccaatga tggtctcttt aacaacgtgc aacatgcgat ggtcgcctct    2820
gaagcttacg ccactttgat cactatgctg gctcagtgta ctgacatgca gtaccccgtg    2880
gatcgccctc tgaactggct gcgtcagatt aatttggctg ctaatgaggc gacgattttt    2940
ggtcgctcga ttaattcact tttccaaact gcctttgacc tctcgccttc cactgtgttg    3000
cttcaacctt tcttagaatc tgatccacgt gcaacgcaac tagccatttc ttacgttcgc    3060
tataatggag acagtgagac cttcgtaccg acagtacggc catctatgat ctcagaagcg    3120
acattgctct tgaacgcac tctttcgcac gaatacaatc ttttcggttt atgtcgtggt    3180
gatatcattc tggggcaaca catgactcct actgcgttca atcccttagc tcctcctcct    3240
tctgtcattt ttaacagggg tgacgctgat gtttatgaat tcggatctcg tagcttcgct    3300
aacttcggta tgaatggaga ggagattttg gttatggacg cgaacggtgt gcgtcgtcca    3360
ctacttggcc ggtgggttat gccgctccag cttttgatgg tgaatattgg tgtatttccc    3420
aagctgctgt tggatcgtat cttgaaagga cgtctatata tcagacttga agttggcgcg    3480
tatccataca cggtgcagta ctaccaggga cgtgagttca ctgacggttt cacattgctt    3540
gagcaatgga tgtccaaggt gtcacccatg ggtatccctc ctgttccttt tctcatgcca    3600
cagtccgagg gacacaatat cacttcaggc atggtcactc attatatctg gtccactgag    3660
tacaatgatg ggtcactctt tgccacgaac actgacctgc cggttactgt atttgggcct    3720
gaccgcacca ttcctatcga gcgctatcgt gcactcgttg acccaggcgc cctccctgcc    3780
```

| | |
|---|---|
| actaaccaac tgccgcacac tatcgacctt tattgctcac taagacgcta ctatctggag | 3840 |
| acacctccca ttactgccac tgtcactact tatggcgatg gactccccgc gctgaaccat | 3900 |
| tagagcggcg aggctagacg cgagctgatc gcgtcgactc tcgttggaga ttattcatc | 3959 |

<210> SEQ ID NO 2
<211> LENGTH: 3830
<212> TYPE: DNA
<213> ORGANISM: Artificial Sequence
<220> FEATURE:
<223> OTHER INFORMATION: Synthetic Sequence

<400> SEQUENCE: 2

| | |
|---|---|
| gcttttcct caccatgcat gtcaacgggt tgatgatgc tactctctcc tacgcacaat | 60 |
| ccatctcggg ggttatccca atgacaaata agctatttga gcaagcatct gcatcgatac | 120 |
| gtgccctacc tcgctcacat gtttatacct tattagataa tgtaaatttc tctgtttcat | 180 |
| gcgtgatccc aaatcgtatc ttccatcatt ccgaccactc tgagtatttt tacatcgacg | 240 |
| cggttaatag ggttagacgg aaacaagtta ttgatgctga cgatgtattc gtgccaaatt | 300 |
| gcaacctgca gggtcttgtc actccaatgg aaagattgcc aaactatggt cagttgtctg | 360 |
| agactatttc gtcgaacgct cgggacggct tgccatccgc acgcgtagca gctacatttt | 420 |
| ataacatctc ggtatctcag gctcgtcagg ttaaagcccc acttgaaaca tttttgttac | 480 |
| ctttgttact aactgaaacc tgcccgttat cggatgatcc ctgcggactt gacacctcag | 540 |
| cttctccccc gatccatgct aatctagcac tatgggtgtt acgtgaaatt agtcgaacta | 600 |
| tttgtggatc ttcaaaagac cgttcgccct ggttattact cgattcaggg gttgcatggt | 660 |
| tcatgtctcc actgatgtca tcagctattc cacctctcat ggctgactta actaatctgg | 720 |
| caatctataa acagatttgt tcagtgcccg acgagcttca ctctcttgca gttcaagtag | 780 |
| ttttgcaggc tgcagcgtca caatcatatg gtcattacat attgcaaacg aagtcgatat | 840 |
| ttccacagaa tacgttacat aacatgtttc gtacactcac tgatggcatc gttccggtca | 900 |
| tagagtggtt ggaaccgcgt tccaactatc gcttcatgct tcaaggtgcg cgtaaagtga | 960 |
| cttcagatga cgcgaatcaa gctccggata atacagaagc cgccgagcaa cttggccgaa | 1020 |
| aaatggggtg cttggatgtt gtacgctctt tacggaagat gtctgcgtcc atcacggtgc | 1080 |
| attcacatga tgccatgact ttcgtgcgtg acgctatgtc ttgtactagc ggcatcttta | 1140 |
| ttacacgtca accgactgag actgttttga agagtacac tcaagctcct accattgaag | 1200 |
| ttcccattcc gcaatccgat tggtcaccac ctattggatc tttacgatat ctctcggacg | 1260 |
| cctgctccct ccctgctgta tatttggcta gagcttggcg aagagccgct tctgctgtag | 1320 |
| tagataaccc acatacctgg gaccccttat atcaagctat cctccgctct cagtatgtga | 1380 |
| cgtcacgtgg tgggtctggt gctgcattaa gagatgcttt gaaggctgca gaagttgaac | 1440 |
| ttcctcagta tcctggggtt agtgtcaagg tagcaaccaa gatttatcaa gcggctcaga | 1500 |
| ctgcggacgt gccttttgac aagttgtctc gagctgttct ggctcctttg tcgatgggat | 1560 |
| tgcgtaatca ggttcaacga cgtcccagga ccatcatgcc tatgaatgtc gttcaacagc | 1620 |
| agatttcagc ggctcacact ctatctgctg actacatcaa ttatcatatg aacttatcga | 1680 |
| caacatcggg tagcgcggtt attgaaaagg tggttccgtt aggtatgtac gcgtcttgcc | 1740 |
| ctcctgctca agcagttaac attgacatca aggcctgtga tgcatctatc acatatcagt | 1800 |
| atttctttc tgttatcgtc ggtgctatac atgaaggtgc agcgggccgt cgtgtttcat | 1860 |
| cttcattcat gggagttcca ccaagtgtgt tatctgttgt tgatgctagc ggcgtgacgt | 1920 |

```
cctcagtgcc tatttctggt ttccaagtta tgtgtcagtg gttagctaag ctttaccagc    1980
gaggttttga gtaccaagtg acggacacgt tctccccagg taacattttt acgcaccata    2040
ctactacttt ccctccggc tcgacagcga cgtctacaga gcatactgcg aataatagta    2100
cgatgatgga tggatttctg cgtgcttgga ttccttcttc cggtgcgtct gatgtactga    2160
agaagttctg taaatccatt tcaatacaac ggaattacgt ttgtcagggt gacgacgggt    2220
taatgattgt tgatgggcta tcatcaggta aattgtcagg cgagataatc gatgaattcg    2280
ttaaagagtt gagagcttat ggcaaatcat ttgggtggaa ttatgacata gagtttaccg    2340
gaaacgctga atacctcaag ttgtatttct aaacggttg ccgtataccc aacgtttccc     2400
ggcatccgat ttgtggcaaa gagcgcgctt cgggggacaa gttagaaatg tggccatcca    2460
ctattgacat cttcaatggc atatttgtga acggtgtgca tgatggctta ccatggcgca    2520
ggtggttacg ttattgttgg gcccttgcac ttatgtattc tgggaaaacc gtacgtcacg    2580
acgactctga tgtgttgata cagtacccta tgtggtcctt tgtgtattgg ggtttgcctc    2640
ccgtgagcgc gttcgggtct gatccatgga tctttctcc ctacatgccc actggtgatc     2700
atggtttcta ttcaatgtta actttagtgc gccctctggt cactaactta tccccgtctt    2760
cagacacttt gggattattt ggtcaatgtg atcacaacgt tctgttcaac ttcgagctag    2820
tctaccaggg ctattacatg gctcaatgcc cacgacaacc ctctcgttcg aatcgtaggg    2880
atgatcctga ttctgtacag cgctttgtta aggctttaga gtcttatctt tatatctccc    2940
ctgagctaaa atcacgagtg cgacttggtc atgaccgatg gcagaagtta gttgggtata    3000
cggagaaatc tcccccgtcg cttgacgatg tagccttcaa atggttccgt agcgcacaag    3060
aagctgacct tccaaccgcc tctgaaattc aaagcatgga tctgaccttg ctgtctgcca    3120
gacgtcgaac gtatcagggt ttctccaaat tgttaaacat ctacttgagg gtgacttggg    3180
acttatccga tcctgttgcg cacgctgtcg atcctcgtgt cccttatgc gctggtgttt     3240
ctccatcgaa tagcgagcca tttctcaaat tgtactctgt tggcccaatg atgcaatcta    3300
cgcgtaaata ctttagtaat acattattca tccatcgaac tgtgtcgggt cttgacgttg    3360
atgttgttga ccgtgcgttg cttaggctac gtgctcttaa cgcgcctgat gatgtggttg    3420
tagcccaact tttgatggta gggttgtccg aagctgaagc cgcaacgtta gcagcgaaaa    3480
tccggacgat ggatattaat gccgtgcaat tggccagagt cgtcaatctg tccattcctg    3540
attcgtggat gaccatggac ttcgaccgct taatacgaga tatcgtgtcc atcactcctc    3600
taaccgtccg atccctaacc accgatctac cttctggtgt accatgggct cgcgcgatat    3660
tgcagttcct aggtgcgggt gttgcgatga cagctgttgg accctgcgt cgtccttact     3720
tgcactcagt tgccggggc atgtcctcat tcattaagca attccgccgg tggatgcgtg     3780
ccgaaacgag gtagcgtccg tgcctggcat ggctcgagga attactcatc                3830
```

<210> SEQ ID NO 3
<211> LENGTH: 3907
<212> TYPE: DNA
<213> ORGANISM: Artificial Sequence
<220> FEATURE:
<223> OTHER INFORMATION: Synthetic Sequence

<400> SEQUENCE: 3

```
gcttttccac ccatggctca gattcgaggc cttcggttgt ctacgacact ctcagctccg      60
ccaccacgaa agattgtaac ttctcatacg tatgatgaac taatctctgc tttaaagttg     120
```

```
acaaccaaac cttggcgccc tttgacatca cgcggagatg actcgattac agcagtacag      180
cttctctttc cccttaatgg ttatattgag cccatgttca tgttggagaa ggacatgact      240
cacgacgctt tcgagtcttg gattacgccc cttctgtctg ctctggctga ccagttgctc      300
agacgctacc ctattgctgc ttatcatgga caattaatta ccccttgtt agccaatgct       360 gttgttgccg ctttcttatc gaatgtaccc tatgcacatg cgctggacca cctctttctg      420
gttcgtggaa acgttgagga tattatggat gcgggaatta caattcagaa tcatttatgg      480
tttgatcgtg gcgctatcgt aactccggct gggcagaagt tgttcagtt gactggttac       540 aatttctcat ccaacgatcc gtgtttattc tctaagcaat tacgctgcta tggtcttgtt      600
tactattttc tcaacatgtc tgattgtctg acgtattgtt ggcgtcatct atctaactca      660
actcctctga tacattttga tcgtccttct aacgggattc attgtttggt accctccgaa      720
tccacgacac ctatcgcggg ttcgctacct gtgtcagccc tcagctctat tctgttggag      780
tcttgccttc agcagtcttt actcaatgct cttactccta caggctcgcc agtcattagg      840
caggtggagg tgctactacc tctatcgtca ccattcttcg aacgtctgaa tactctagaa      900
tattctcttt ttgctctttc gaacgctctg attaacggct accagttagt agatttacgt      960
tccggacatc cagattgcgc caccgtcgcc gctattttaa ctaggttaac tgatttctcg     1020
aaaggtatca ctgttattca accacgtcct gctcttttca ctatcaataa tgatagtcct     1080
ctgacgtata gtggagagaa cgccaatttc atccagcgct ggcgtccat gtctggaaga      1140 tctattggcc cagtcgttat tgggaaatct gttaatcatg ccgtcggttg atgccccag       1200 tttgatcccg ctacgtcata caatcctgac ttatcattgg attcgctttc acgagccacg     1260
acgctgccac ttcgcgctaa gtactctact ttctggtctg gccccgcact cttttccttt     1320
gcttcgtgtg acaggcacaa tggcgtgtat gacattcaat tcatggctca gtttcctcct     1380
acgtatttta atgatgatga cacctttcct cggtcgaggt tctcttccta ccgtgctgtt     1440
aaagatcgat cgctgttaaa agataccgcc aacttgatat atatctcaaa cttatcaagt     1500
tcgcatgacc accgtcttgt ccctgattct aagaccatga tctacgtggg atcgtctggt     1560
acgcatgcag ataaccaacc ttccatcatt aaacctcttc tagctgggtc tcttccaggt     1620
gttttccgtc ccccgtccgt aaagcagatc ggttgggagg ttactaacgg gactatttgt     1680
gacattgaac tgccttttgg ctaccggtacc ttctttttcg tgtacagtga cgtggatcgg    1740
gttcactcgg gcgactccga cctacacgct tcctctcgtc gcttttgctc tcatttggac     1800
atgttaatga aattgacgtt tagggggggt tcttttggtcg tcaagtgcaa cttttccaact   1860 aacttggttt ggcgtcacat cttttcgacc gtttctccct atttctcatc tattcatcag     1920
atgaaccctc ttgtgtcaaa taatttggaa ctgtatttat tatttgcgga gcgtttgcct     1980
gtccctgatg ttgcttttcc tccgtcggcg gactttgtct ttttcgggcg atcccatttg     2040
caacgctatc gagtattgcg tgactcattc tccaacgtgc cctccatcgg ctccactctt     2100
accttggatg attcattgac ggtatctatt ctgaattttg tcgatgttac ttccctatcc     2160
tccatcgagg atcaaagagc tttatccgct ttctcggtcc ttacctcttt ggggtctcag     2220
aagttgtcgc ttcatcccta ctttgatagt tatcgcacgc atctcaccgg aataatcact     2280
ccacattctc gcaacatttt agataggtta gcatacgttc cgcgtgtctt ccttcaacg      2340 attgacgttc aacatcgtgt tatggcttcc tcagatccag agattttggg ctttcgctcc     2400
aactcttgga ctcaattgtc ttttttctat gacgctacgt taactgcaac ggattttact     2460
gatgtgaagc attggttgga tttgggaact gggcccgaag cacgcccgtt gtccttttctg    2520
```

```
ccgactgatc tccctatcac cttgtgcgat actcgacctt tcgtttccc gtccggctgt    2580 tgggctactt tcactgattt cttaagttac gattaccttg ttacgaatgt cgtcttatcg    2640
actggtgccg acgttgtgtc ctgtattctc tccctagggg cagcttgtgc tgacgctaac    2700
atgactctac atgagggcgc gcggcagcta atctcccagt gcgtagatgc cagtgttaag    2760
acgctgtttc tacagcttaa ttgtcccctt ccatcagcgg gtgacgtgtc tcgagagatt    2820
cttgaggtgg ttcagactaa ctcaacgtac atatttcata ccttgggtcg tgtcgagccg    2880
tttattccat attccgccct cttagaaata gtcgaggatt tgtgccctgg tatcgtcgtt    2940
gagattaaaa cgatggattc ttctctttcc tggcttgact acgctgttca atctaatgca    3000
tcggtgacat cagatgacat tgtcctggcg atgcggttgt ctcacttctg tcctcttttt    3060
gtgtttcatt ttgatcgtca gtctgctcaa ttcccagatg acgcgcgtgt tggtgctcct    3120
ttcaccgtca cactgctaga ttatgaagac actcgatcat atgaggtgac tttagataat    3180
gttactattg ccactattac cgcgggcgct ttggtcggat tttcatctgg tgtgaccgtc    3240
acctcgtcca caaccagct ggttctgact attgaccctg cgagtccagg aattctgtcc    3300
gtcatccaag tcctccccgc ccgtatctca ctaggcagtt gcgtgataga agctcccgac    3360
ccatccctct ctctgatctt tcctgctacg ttagatactt ccttatcagg aaccgatctg    3420
gagttgtttt tgtctgactg gtatgacgtt gctctattct atgtcgacga agcgcactct    3480
cgactgctgc cagtatccga caccaagtat gagatttatc gtaaggatca aacgccaaat    3540
agtcgaataa tcaactatat cttcgatcgt tctgacgtgt tctttaaatt ggtgctgtgt    3600
gacgtttcgc catctggaat aggtcgtttc atctaccgtg agttaccaga gctgagttct    3660
ccggtatggc ctgacgacgt gcgtactttc ttatccatac catttgaatc ccctatggtg    3720
attgtatcgc cggacggacc cgtaaattat gacggtgtca atttcacccc tccaacttca    3780
tggcttacag ttgacggcag cacttgcgtt gtagacggcc gtccttcgtt ttatgtgccc    3840
cctggccgat atggtctggt gagagtctaa acgaccgcgg gcctccagta aagggtgtt    3900 attcatc                                                              3907
```

<210> SEQ ID NO 4
<211> LENGTH: 2283
<212> TYPE: DNA
<213> ORGANISM: Artificial Sequence
<220> FEATURE:
<223> OTHER INFORMATION: Synthetic Sequence

<400> SEQUENCE: 4

```
gcttttctcg acatggccta tctagccaca cctgtgctag gagtcggttc tcgcattacc     60
gccttagatc gtactattga cgccattacg ttgaaacctc gaatcgacct ccaagatgtg    120
tatacaattg atcccacact aactctgcgt cagatagagt taatctcttc ggggacttca    180
atggacgaca ttgctcgtgg attgttacat cgggactggc gtcgtcaatc caccatcgtc    240
ttgctccctt ctcgtcgctc gctccttgag tacctattgt ctaatccttc tgtctgtccg    300
gacggcttaa atcgttctcg ccttaaagga ttccaaaaac gcccaaatga ttttcgtgtc    360
caaaacttct tctctccact gattacggac tcaacatcaa ttgctacgta ttctcggtgg    420
cttaatgctc atcctattgt gtactctacc actcacaaag tcgctggtgc tcgggtacgt    480
ctctttggac ctgctaaatt atacattctg tcacccgatg ttctccgtga attatccatt    540
ttgaaatcca ctgatcgcat cttagttgta cccacggcgc gcgtgtatat cggttgtttc    600
```

```
cccagtgctt ctactagtaa ttgcgtactc actgcgcgcg aacgctggaa tgcccctgat      660
gttcaccctg tcgtaaaggc aatccaatta gcttatgacc atcaatatcg tgtcactgcc      720
cgctatctct cagaccctct tatctcggct cttcttcttg ggaaccggtc ggtgaagacg      780
ttgaaggtac agccagtgga agctagagca gcacggtcag ttggtattcg cgttcaagcg      840
atgacacctc ctcgtggtat taacacctca attatccagg tcgttgatct caggttgcaa      900
tgccggcatt cccttattcc caccgaaagg ccattcccgc taacgttcat cggcctccca      960
tcgtgtctgc ttcaacattt ggatctaaca ttatccgatg attgggtgcc cattcgtgat     1020
catacaggca tgtttgaaat gtggtttatg attcttacgc tcacttgtga taagatcctt     1080
gacggacggg gaaatgccgc tttccttatt cccagctcta ctaacgcgtt gtcagttaac     1140
tatgtacagc tcacgtcgac tgcatctcca cgtcctcaat cgttggcggc taacgcatct     1200
gggcggatag attccattgg gctgtgcatg cctaaaggat ccttcaagtc aactatgatt     1260
aaatttctca ctggattgga gatttgcggc actcgagtga tgtatccaga cgtcgtgatg     1320
gatagtgatg atgtgggcga tgcttttgat cctacttttg aaaccgcgct acacgatgca     1380
ttgttggctc ttgatccgcc ttttgacgtt gacaaattag ctagccccac cgatttagtc     1440
aaccaggaat atgtcgcgtc tcacatgtac ccaacattct tacggctcgt caatgagttg     1500
ctaacgccta aagcttcaga attgtactca gagcgtagcg ttgaattccg atctcttacc     1560
tacgcgcatg ctgattctga atttcttaac gcatgttgga ccgctcgctt gatgcgatgc     1620
tttatcaact atcatgaaga gcaaaacatc ctgcttcgtc ctggacgcgt tggcggtgtg     1680
ttattccaag tcgcgttgag tcgctgctat aagatgttcg ctacttccac tcctgcctcc     1740
cctttatcac tgttcctcaa gtcgttgttc gttccttgga ttgaatctgc tccactacta     1800
gcgaacttga ctccaaacga gtcctctcgc gtgttagcgt ggtacatacc ttcttcgtat     1860
tggagtgaca atggttggtg cacttgcgac acccatcgtc atgttacctt ctctttcatt     1920
cgcggtcttc ctgcggacct gtcggtgtta gatctgtttg attggtctcg gttccgcgca     1980
actataaacg tagatgcgtc tctagtagag ctaggcgctg atattcgtgc ggttaaggtg     2040
tcagttcatt ggacatctca gaagcccact gtggacgtct ttgataatcg cgcgcttttc     2100 actcccttc agcattacca cttaagcctc cactgtaact gtgcgcctgg tcgccctttc     2160
ttcgcgaaaa atatgaaact gtatctgtcg acggttggag gcgagcactg acgggccgtg     2220
gggcggtgac acccagggag ggtatgctgg taaccctggg ttagtcgtct tgagatactc     2280
atc                                                                  2283

<210> SEQ ID NO 5
<211> LENGTH: 2158
<212> TYPE: DNA
<213> ORGANISM: Artificial Sequence
<220> FEATURE:
<223> OTHER INFORMATION: Synthetic Sequence

<400> SEQUENCE: 5 gcttttcag tgccagtctt tctcacaaga tgggtaacgc gacgtctgtt gtgcagaact       60
tcaatatcca aggtgatggt aatcattttg ctccatctgc tgagactact tcatccgccg      120
tgccgtcatt atctttgaat cccggactgc tgaatccagg tggtaaggcg tgggttctaa      180
tcgatccttc tctaaatgcc tccgatcctt cctccctacg tctgatgact tcggctgatc      240
tgtcaacact tccccaatcc gcgattagta attctactgg gttctcccca acttctggta      300
tgtatgccat cgctactaaa gagacgttga gtgtaatcac tgagcacgca atttcccagt      360
```

```
tcgataaatt gcagatggct tgtgagttgg accgcgatta tctggacgct agagggtttt    420
ctcctgagtc tgtgaatatt catagttata tagcatatgt tgattgcttc gtgggtgtat    480
ctgcaaggca agctgcgtta aactttaagc aacacgtgcc agttattact aaatctcgca    540
tgacacaatt catgacatcc gcgcagaata tgttgcaagt actcggacct tgggagcgtg    600
atgttcgtga gttactcact attcttccta cctctactac cgctggtaaa attacgtgcg    660
atatgaagtc tgtcgtcgct tttattgatg atcagctctc tgataccagt ttgtgccgtc    720
tgtaccctga ctgtgctgct gcggcagtgg ctagacgtaa tggtggcatt agatggaaga    780
cacctgatac tgacgaagct ccttcgcttg caactaacga cattgctgcc tcaactatgg    840
gtacgcttgc gaatactaca ccactggctg agaagtcgaa ctcgggcgag gagtcaatgc    900
gcttagtgag tgacgttggt gtggacatcg tctgttctcg tagccctata agttcttcag    960
tttggtcacg tacggttgaa cctaaatcgt acaatattag aaccttcgt gtagaagagg    1020 cgctttggct acgtgagtgc caggcgacta ctgggtttga tgtacagtac acactgcctg   1080
accagactac acataaacat ttctggcttc agaaagggtc agttgtcata aatcttgagc   1140
aaacgggtag tatgatgttt gatgtgaaca tagcgggtaa agattataag aagggtacct   1200
ttaatcctga taatcataag ttggtccttt tggttatgca gtcaaagatc cctttcgagt   1260
cttggactgt cgcttctcag attactggca tcgctcaagt ggctgaggtt actgtgcatg   1320
ctgctgatag ttcgactcct aaccagaaga taataggtga gacttcgcta tcttatttgt   1380
ttgagagaga gacagtgacc acatcaaaca ctgaagtcaa tacatatctc ctgtgtactt   1440
ggcaacttga taacgaacag agcaatgatg caaacgtctg gccagacgca tgggatggga   1500
tcacaacatt gactccgctt acttccggta ccgtgaccat caaggggact tcggtggatt   1560
ccgtcgtacc gtctgattta gttggcgctt atacacctga agctttggct gccgcgcttc   1620
ctaacgacgc tgggttaatt ctagctaata aggcaaccag actggctgac gctatcaaga   1680
aagaagatga ttctgtgatc gatgagtctt ctccttttag cactcccatt caagggtcc    1740 tggctgttca acaacttgat accgtgggga cgcgtggtat acgtgcactc cagcatccgt   1800
ccattctgaa acgtatcgct tcacgagctc tccatatgtt ccttggcgat ccaaagtcta   1860
ttctgaaaca agcgacgccc gtattgagag accctgacgt ttggaccggt tttgttcaag   1920
gcgttagaga cggcatacgg actaagtcgc tatccgctgg agtacggtct gtgtataata   1980
acgttaccgc cactcaatcc gtgcaaatgt ggaagcaggg gttcctgacg aaaatacaga   2040
cgttgttcaa gccatcgtga ggtgctaagg cctctctctg cggcgggtcg gtgggcacgt   2100
cgtggtgacg ctgaatgcac ggggaagtga cgctccctgg attggcacgt tattcatc     2158
```

<210> SEQ ID NO 6
<211> LENGTH: 1996
<212> TYPE: DNA
<213> ORGANISM: Artificial Sequence
<220> FEATURE:
<223> OTHER INFORMATION: Synthetic Sequence

<400> SEQUENCE: 6

```
gcttttgag tcctagcgtg gatcatggcg tcaaccaagt ggggagaaaa gccgatgtcg      60
ctctcaatgt ctcacgatgg atcatctatc cgcagtgctg cctcacaatt tttgtcggtt    120
cctctgtctc attcaacgcc tatcccacct caacggaaga ctgtactatt gaactttatg    180
attggtgatg aactggttac tgttcagggt gctcttgccc cgttcgacga atactggtat    240
```

-continued

| | |
|---|---|
| gacaatcaac ctctgttggc tcaggctgtt gagatgctag cgtctgagga tcgtttgcgt | 300 |
| caatttgagc attatgagaa attcctactc aagaagggtc accaaatagc tgagatcatg | 360 |
| aaccgactac gtctcttttt cacggatgtc ctcaaaacca agatggaagc tgacgcttta | 420 |
| ccggctttag ctcaatacct aatggctgga actttggagg ccgtttctac tgtccactca | 480 |
| cctgatgctt gcgtcccagt cacttcgaag atcttagcca agcagcagac cattgccaag | 540 |
| gctcctggac ttctcgatga ggaagagtac aatgtcatcc gatctcgttt ccttacgcat | 600 |
| gaagtctttg acctaacgtc tgacctacct ggggtgcaac cgttcatgga catgtactac | 660 |
| gctactgttc cccgtgctga ctctacagga tggtgtgtgt atcgtcgaaa gggcctgctt | 720 |
| atccactctc ctgatgagca attctcggat ctgaccattt tctccacacg tcttactgcg | 780 |
| tcacatgagc tgcagctggt ggctggcgat gttgtcgtag cctgttttgg tctcatggac | 840 |
| gtctctgaca ttgcgccatc tcatcatgca tcggtccagg aagaacgtac tctagggacc | 900 |
| agtaagtatt cgaatgtaac ggctaatgag catcctctgg tattcttctc acctaatgcg | 960 |
| ctccgttggg caattgacca tgcctgtact gattccctgg tttctcccccg gaatattcgt | 1020 |
| gtttgtgttg gcatcgatcc tctggtaact cgatggaccc gagacggcgt acaagaggca | 1080 |
| gccattctta tggatgataa gcttccatca gtaggtcgtg cgcgtatggc gctgcgaaca | 1140 |
| ttgcttctcg ctagacgctc accaatgcca tccttcttgc tcggtgccct gaaacagtcc | 1200 |
| ggcggtcagc taatggagca ctatcgatgt gatgcggcta atagatacgg atctcccacc | 1260 |
| gtcccgatct cccatccgcc accatgctca agtgtcctg aactaaaaga caaaattgcc | 1320 |
| aagctctctt catcgcccat acctaaagtt gattcatccg ttggtccagc cgctctgctg | 1380 |
| tctaaaattg ctgaccttca gcgtgctaac agagaactgt cattgaagct ggtcgatgtt | 1440 |
| caacccgctc gggaagatca cttgttggct tatttcaacg aacatgtgtg tgtgaacggt | 1500 |
| aaagatcatg aaaaaggcct gcttgctcgt tgcaatgtgt ctggcgattc aatcacctct | 1560 |
| atccttagcc agcgtgtgaa gaaccgtgag agatttgaaa cccgattgcg tcatgaggct | 1620 |
| agtgttgaat gggaacctcg tgtggaagcg ttaaatcaag aactggctaa agcgcgtgtc | 1680 |
| gagcagcagg atatgatgac tcaatcccta cagtacctca acgaacgtga tgaactgctc | 1740 |
| catgaagtgg atgagctcaa gcgtgaactg gctactctac gttctgccaa tgtacgattg | 1800 |
| aatgctgaca atcatcggat gagtcgtgcg acacgtgttg gagaagcttt cgtcagtgat | 1860 |
| gtcgagcctc taccttctgg cataccctggt gaatcgaaac taactatgga agaattggtg | 1920 |
| gatgatctgt gagctttgac ctgtgactcg acttctctct gattccatgt acccacggcg | 1980 |
| gactcggtta ttcatc | 1996 |

<210> SEQ ID NO 7
<211> LENGTH: 1643
<212> TYPE: DNA
<213> ORGANISM: Artificial Sequence
<220> FEATURE:
<223> OTHER INFORMATION: Synthetic Sequence

<400> SEQUENCE: 7

| | |
|---|---|
| gcttttcaa tcccttgttt gtcgatgctg cgtatgcctc ccggttcgtg taacggtgct | 60 |
| acagctatat ttggtaacgt ccattgtcag gcagctcaaa atactgcagg tggtgacttg | 120 |
| caagcgacct catccataat tgcatattgg ccctatctgg cggcgggtgg cggtttctta | 180 |
| ctgattatca ttatctttgc catcttctac tgttgtaagg ctaaagttaa agcagacgct | 240 |
| gcgcggagtg ttttcaccg tgaacttgta gcactgagtt ctggtaagca caatgcaatg | 300 |

```
gctccgccat acgacgtttg aagtacgacg ctttgatttc tgcccaatat cccttcgtga      360
gcttgctact ccatcattta ctgctgtaac tgggattgac ccatcgcagt attttaacat      420
tgagcttccg catactcatc ctctctactc taaactgccg actctgttat ctcagccctg      480
cagagttcac gtgcgtttaa ttcgccgatt cgctctccgc tcaacgttgt cgggcatctg      540
tgagtacgat tgtgcgttac tgttctcccc acacgccatc gttccattat cctcatccga      600
ccagcagtct tatcttatag ttcattggga tggcgggtct cagtccatca cagcgaagag      660
aggtcgtcag cttgatactg tcattgactt cgaacgcgac tataaatcct ggcgatctga      720
tgtcaatcca tgagcggttg aacaatttgg aagcgtctac agaatcacta tatcgctcca      780
tttccagcat gtccactacc gtttccgaca tttccgcaga tttgcagaac gtgactcgcg      840
ctttggatga tgtgaccgtt aacttaaatg gtatgagagt caccattact acgtttcaag      900
attctatttc cactctctca acaactgtga ctgacttatc cagtacttct tctgcgcact      960
cggaagctct atcttcactc cgaactacag ttaatgggaa ctccaccatc attaacaatt     1020
tgaaaagtga tgtatcgtca acggtctag ctattacaga cctgcagaat cgcgttaaat      1080
ccttggagtc tacttcgagt catggactgt ccttttctcc tccccttagt gtcgctgacg     1140
gcgtagtgtc gttgaatatg gacccgtact tttgctctca gcgagtctct ttgacgtctt     1200
actcagcaga ggcacaacta atgcggttcc aatggatggc cagaggcact aacggatcgt     1260
cggacgacat tgacatgaac gttaatgctc actgtcatgg gagacgcacg gattacataa     1320
tgtcgtccac gggaggtctt acagtcactc gtaatgccgt gtctttaacc ttcgacttga     1380
gttacattac aagcctccca tcagacctct cgcgtcttat tcctagtgca ggatttcaag     1440
tcgcgtcgtt tcctgtggat gtatccttca ccagagattc cacaatccat acgtatcaag     1500
cttatggagt atactctagt tcgcgtgtgt ttactattac tttcccgact ggtggtgacg     1560
gtcccgcaaa tattcgtttc ctgaacgtgc gtaccggcat cgacacttaa ggtgtggcgc     1620
cgtacgggga ttggttattc atc                                             1643

<210> SEQ ID NO 8
<211> LENGTH: 1324
<212> TYPE: DNA
<213> ORGANISM: Artificial Sequence
<220> FEATURE:
<223> OTHER INFORMATION: Synthetic Sequence

<400> SEQUENCE: 8
gctttttctc ccacgatggc gcgtgccgta tacgacttct tttctacgcc tttcgggaat       60
cgtggtctag caacgaatcg tactcaactg tcatcactac tatcaagctc gaattcccca      120
tggcaacgat ttctatcatc aatgactcca ttgacagcgc caggtatagt ctcaacacct      180
gaagcaccct atccaggctc gttaatgtat caagagtcta tgcttcacag tgccactgtc      240
cccggagtgc tcggcaatcg cgatgcttgg cgtacattta atgtcttcgg actttcatgg      300
actgatgaag gactgtcagg actggtagct gcccaagatc ctcctcccgc tgccccgtat      360
cagccagcct ctgctcagtg gtcggacctc ctcaactacc ctagatgggc gaacagacgt      420
cgtgagctgc aatctaaata ccctcttctg cttcgatcta cgcttctttc tgccatgcga      480
gccggtcctg ttctttatgt tgagacgtgg ccgaacatga tctcaggccg attggctgat      540
tggtttatgt cccaatatgg caacaatttc gttgacatgt gtgctaggct gacccaatct      600
tgttcgaaca tgcctgttga gcctgatgga aattatgatc agcagatgcg tgccttaatt      660
```

```
agtttgtggc tcctttcata catcggggta gttaaccaga caaataccat cagcggtttc    720
tacttctcct cgaagactag gggtcaagcg ttggacagtt ggactctatt ttatgccacc    780
aacactaacc gtgtccaaat tacgcagagg catttcgctt acgtctgcgc gcggtctcct    840
gactggaatg tagataaatc gtggatagct gcagcaaact taaccgctat cgtcatggct    900
tgccgtcaac cgccgatgtt cgccaatcaa ggtgttatca atcaggcaca aaaccgacct    960
ggcttctcca tgaatggggg gactcccgtc cacgagctca acttgttaac taccgcacag   1020
gaatgcatcc ggcagtgggt ggtggccggt ctggtgtcag cagcgaaggg gcaagcacta   1080
acgcaggagg ctaatgattt ctcaaacctt atccaggcgg atctaggaca gattaaggcg   1140
caggatgatg cactgtacaa ccagcagcca ggatacgcaa gaagaatcaa acccttcgtt   1200
aacggtgatt ggacaccagg tatgactgcg caagctctgg ccgttctagc cacttttacc   1260
gcttaggcgt agggtcgtac gctgcccgag tccagccctc cggcagcacg tggatgtatt   1320
catc                                                                1324
```

<210> SEQ ID NO 9
<211> LENGTH: 1202
<212> TYPE: DNA
<213> ORGANISM: Artificial Sequence
<220> FEATURE:
<223> OTHER INFORMATION: Synthetic Sequence

<400> SEQUENCE: 9

```
gcttttgag tccttagcgt gcaagccgca atggaggtac gtgtgccaaa ctttcactcg     60
ttcgttgaag gaataacgtc tagctactta aagactcctg cttgttggaa tgcacaaacg    120
gcctgggaca ctgtaacctt tcacgttcct gacgtaatta gagtcggtaa tgcgtactgt    180
tgctctcagt gttgtggcgt actttactac ggaaccctgc catccgacgg aaattacttc    240
ccgcatcaca agtgccacca gcaacagttt aggactgata ccccgctact acgatacgtg    300
agaatcggta ggacaactga gcagttgctg gatcaatatg ctgtcgctct ggagtctatc    360
gccgagcact atgatgagat tagccaacgt atggttgacg agcctgagaa tgatgaagtt    420 acgcccttg acatcgtaac gcgtaccgag tccatcagaa gtgacaaggc agtagacccg    480
gatttctgga ctcacccct tgagcgacgc tctgatgatt ctcgtcgaga catcgcctca    540
gcatgttgga ggatgattga cgcatcatca cgtagtttga ctcttcccaa ttgtcttgtt    600
tccccatctg tgcatccacg ctccgtcttt ggtcaaatgc aaacgaccac caccatatat    660
gacgtcgctg cgtccggaaa ggctgttaag ttttccccga tggttgctac ccttgctcaa    720
cgcgatgccg gacctgtgat gctcgcgaac gctgatccag ccgacggcgt atattcattt    780
tggacatctc atttcgcagt ttcgccgcta attggaggag tcgggattac gggacagtac    840
gctcgtgagt cctaccacca cgtgggtcat ccagtcgttg ggagtggtaa gaaggcgtcg    900
cactacagaa acctgttcat ggaagcgtgg cgtggatggt caaagtcagc ttttgcatgc    960
gctacaggaa tggaaccagc cgaatgcgag tctcgtttga ggggtcacgc tcgcactatg   1020
ctcggacggt ctctgccgaa tgtctgtgat gatgacgtct ctcaacagtc tggtgctgtg   1080
ctagcgtctc tgcagaagac taccaaattc actgttgtgg agtgcagttg gtaagtacct   1140
ccgggtcaaa atgcacatag gctcccacct atgtgacggt tagcgggact cacctattca   1200
tc                                                                   1202
```

<210> SEQ ID NO 10
<211> LENGTH: 1192

<212> TYPE: DNA
<213> ORGANISM: Artificial Sequence
<220> FEATURE:
<223> OTHER INFORMATION: Synthetic Sequence

<400> SEQUENCE: 10

| | | | | | |
|---|---|---|---|---|---|
| gcttttttgag | tccttgtgca | gccatggaca | acacagtgcg | tgttggagtt | tcccgcaaca | 60 |
| catccggcgc | agctggtcag | actgttttta | gaaactttta | cttactacga | tgcaacatct | 120 |
| cagccgacgg | tcgtaatgca | acaaaagctg | tgcaatccca | ctttccattc | ctttctcgtg | 180 |
| ctgttcgctg | cttatctcct | ctagctgctc | attgcgctga | taggactcta | cgtcgtgaca | 240 |
| atgtgaagca | gattcttact | cgtgagatgc | catttccatc | ggacctaatt | aattacgcgc | 300 |
| accatgtgaa | ttcatcctcc | cttactactt | ctcagggtgt | cgaggcagca | cgtctagtgg | 360 |
| cccaagttta | cggagaacaa | ctgtcgtttg | accatatcta | ccccactggt | tctgcgactt | 420 |
| actgccctgg | agcgattgcg | aacgcgattt | cccgcatcat | ggctggtttc | gttccccatg | 480 |
| aaggcgataa | ctttacccca | gacggttcta | ttgactatct | cgctgcagac | ctggttgcgt | 540 |
| acaaatttgt | gcttccttac | atgctagata | ttgtggacgg | acgtccgcag | attgtacttc | 600 |
| catcgcacac | tgtcgaggag | atgctgtcca | acacgagctt | gcttaattcc | attgacgctt | 660 |
| catttggtat | tgaatctaag | agcgatcaac | gcatgacccg | tgatgcggct | gaaatgagtt | 720 |
| ctcgttcact | taatgagctt | gaggatcacg | agcagagggg | tcgaatgcct | tggaaaatca | 780 |
| tgacggcaat | gttcgcggcg | caattgaagg | tggagttgga | tgctctggct | gatgaacggg | 840 |
| ttgagtctca | ggctaatgct | catgtgacat | cttttgggtc | tcgtctgttc | aaccagatgt | 900 |
| ctgcttttgt | cccaattgat | cgcgagttga | tggagctggc | tctactcatt | aaggaacaag | 960 |
| gtttcgcgat | gaatccaggc | caagtcgcat | ctaaatggtc | gctgatacga | cgatctggtc | 1020 |
| ccactcgccc | actgtcaggc | gctcgccttg | agatcagaaa | tggcaactgg | acgattcgtg | 1080 |
| aaggcgacca | gacgcttctg | tctgtctctc | cagctaggat | ggcgtaaacg | ggacccatgg | 1140 |
| tgcgggtgag | gggccgccac | accctctgcc | gcgacctgga | ctcttattca | tc | 1192 |

<210> SEQ ID NO 11
<211> LENGTH: 3959
<212> TYPE: DNA
<213> ORGANISM: Artificial Sequence
<220> FEATURE:
<223> OTHER INFORMATION: Synthetic Sequence

<400> SEQUENCE: 11

| | | | | | |
|---|---|---|---|---|---|
| gcttttctc | cgaacgccga | aatgagttcg | cgcaaagtgg | ctagacgtcg | tcataaggat | 60 |
| gctactgaat | ctaaggacac | taaagacact | aataaatcta | agccatcttc | tattgatgct | 120 |
| aaagaatcta | cggatagcgc | tacgataag | aaagtcactg | ctccaccacc | aaataatccg | 180 |
| gctgcttcta | ctccctcctc | cactgatggg | gcttcccaaa | catctgtcgc | taagcagacg | 240 |
| aatgataatg | acgcctcagt | taaggaatca | gctcccaagc | ctactgtctc | cagcgacggg | 300 |
| aaagatggga | tgcacggtgc | tgtgaagtcg | caagacgcta | aggctaccgt | agctgtagat | 360 |
| aataataagg | atagagatgt | agtatttggt | ggtgcaggtt | ctggtgacaa | aaatgctatc | 420 |
| acgaaaactg | gctccgttga | caatgatggg | ggtgttaagg | tcgttccagc | caaggatgct | 480 |
| acgatatctt | cggccaaagc | catgatggag | caaaagcagt | tagtcgctgg | tcttccgaaa | 540 |
| caaccgaagt | ctgctaatca | tctgtgtacc | gtctgcatgg | ctcagtttgc | gtcagctgac | 600 |
| gctcttacta | ttcaccaaac | tacgcattct | attggttcca | acgcggctct | gacgagtttt | 660 |

```
tcgatctcta ctgctgttga agaattcatt caatcatggg ctgctgccac atccacggct    720
aacaccaaga cggctttgac tgtgtctgac gttgactcac tgatgatgac tgaaggaata    780
cgccttataa cttgggattc tgggttatgc acgtcttttg agcttgtccc gatcgtccat    840
tcaaacactg ttcaagatgt tatttcatat tcatggttta cgtcaagcta taacatcacg    900
actcccttcc cacaagcgac tgtcgtgcgg attgtcttgc gtactaactg ggctgccaaa    960
ttggattctc cctcttcgtc gcgtgaatgt gatcttcgtc ttgctccacc tacagagagc   1020
aatgctcgat cattctcaat gctactcaat acgggtgcga ctccagaagg cactttcaac   1080
cccaacaccc ttcgtatgaa cgtgctgcag atgtgtcttc agtatgttct agctaacttg   1140
cacctgaacc gtagcactca gtttaccatg gatttgactg ccgcggctcc caatctatct   1200
gcgtctcaac tccgtatcgt tccagaggat aaggagggta aatggtttcc tgtcatgtat   1260
ccatcccgag tgaacatccc actgttcaac aagacggctg attttgttaa tcagtgcatt   1320
cgtgatagag ttggtcgata cgatcgcgcc cagacttttg ctggtgcacc ttctgaatgg   1380
gctgacatgt gggaaacagc agacgcgtta actctctccg tccgcgaaat gtggatgtca   1440
cgcatttctc aaatgaacat tactcccgct gatattgctg acgctatctc cagatgttct   1500
cagtctttgc tcactgttgc cgcgccgaca gctccttctg tggctcgttt gttaccttgg   1560
cgggttagtt ctgatgagag gcagctgctc caactgctga tgtacttaaa tgttggtact   1620
agtgctgact acgttcaacc gattctgtct gcgttcgctc gaactctgtc tcgtgtgtca   1680
ccactgcgaa ttaatcctac cctaatcgct aatgctatgt cgacaattgt cgagagcact   1740
actaatactc agagtcctgc tgcggctatc ttgtcaaagc ttaaacctgt cgcatctgat   1800
ttttccgact ttaggttggc atgtgccgct tggttatata atggttgtgt ccagacatac   1860
ttgtctgagg attcgtatcc gagcagcggt gggtctgtca ctagcatcga cacgttgatt   1920
gatatgtttg tgtgtttgct ggcgttgcct ctggttactg atcctaacgc tccttgtcaa   1980
gcctttatgg ttgtcgctaa tgctatggtt ggttacgaga acctgcctat ggacgaccct   2040
aattttactc agcagagact ggctgcagcg ttcaataatc ctactacctg gcctcaatgc   2100
ttcctccacc ctcaaaatat tgatcggcgc cagtgtccga ttctttcatg gtgggctcag   2160
cagattcatc gtaattggcc tacaccatct cagattactt atggtgcgcc tgatatcatc   2220
ggctccgcta acttgttcac tcccctgat gtgttgctga ttccattaca acataggccc   2280
atccgtatca ccaatcccac cctgaacttc gataatgagt tgacgacttg gcgtaacacc   2340
gtggttgatt tagtcctgcg cattattgac agtggtcggt accagcctaa ttggaatcag   2400
tctattcgtg cgtctatgcg gaatgcgatg acgaatttca ggattattaa gtcctataca   2460
cctgcttaca tagcggaatt gctacctgtg gaactgcgg ctatcgctcc aactctaccc   2520
ttccagcctt tccaggtgcc gtttgctcgc ttagatcgtg acgctatcgt cacccatgtc   2580
aatgtgtcca gacaagctcc caacaatctt gctcaacctg cattgaacat gtccatgacg   2640
taccagcgca caggagttcc aatctctctt agtgcccgtc ccttggccgt cgctctttta   2700
tcaggtcagt atcctactga tcctcctctt cagaccaatg tttggtacgt gaacactctc   2760
acacctctat attccaatga tggtctcttt aacagcgtgc agcatgctat ggttgcttct   2820
gaagcttacg caactttgat cactatgctg gctcagtgca ctgacatgca gtaccccgtg   2880
gatcggccat tgaactggct tcgtcagatt aatttggctg ccaatgaagc gacgattttt   2940
ggtcgctcaa ttaactcact tttccaaacc gcttttgacc tctcaccctc tactgtgttg   3000
cttcagcctt tcttggagtc tgatccacgt gcaacgcagc tcgccatttc ttacgtccgt   3060
```

```
tataatggtg atagtgagac cttcgtgcca acagtgcgtc cgtctatgat ctcagaggcg   3120
acattgctcg ttgagcgtac tctctcgcac gaatacaacc ttttcggttt atgtcgtggt   3180
gacatcattc tggggcagca catgactcct actgcgttca atcctctggc tccgcctccc   3240
tctgtcattt ttaatagggg tgatgctgac gtttatgagt ttggcccacg tagcttcgcc   3300
aacttcggta tgaatgggga ggagatcttg gtcatggatg cgaacggcgt gcgtcgtcca   3360
ttacttggcc gttgggttat gccactgcag cttctgatgg tgaatattgg cgtctttccc   3420
aagttgttgt tggatcgtat cttgaaggga cgcttataca tccgacttga agttggcgcg   3480
tatccctaca ctgtgcagta ttaccaggga cgtgagttca cagatggttt cactctgctt   3540
gagcaatgga tgtctaaggt gtcacccatg ggtatccctc ccgtcccttt cctcatgcca   3600
cagtccgaag gacacaacat cacttcaggc atggttactc attacatctg gtccactgaa   3660
tacaatgacg ggtcactctt cgccacgaac actgacctgc cggttactgt gtttggtcct   3720
gaccgtacca tcccaatcga acgctaccgg gcactcgttg atccaggcgc tcttcctgct   3780
accaaccaac tgccgcacac catcgacctt tactgctcac tgagacggta ttatctggaa   3840
acacctccta tcaccgctac tgttaccact tatggcgatg gactccccgc gctgaaccat   3900
tagagcggcg aggctagacg cgagttgatc gcgtcgactc tcgttggaga ttattcatc   3959

<210> SEQ ID NO 12
<211> LENGTH: 3830
<212> TYPE: DNA
<213> ORGANISM: Artificial Sequence
<220> FEATURE:
<223> OTHER INFORMATION: Synthetic Sequence

<400> SEQUENCE: 12 gcttttttcct caccatgcat gtcaacgggt ttgatgatgc tactctctct tacgcacaat     60
ccatctcggg ggttattcca atgacaaata agttatttga gcaagcatct gcatcgatac    120
gtgccttacc gcgctcacac gtttatgctc tattagatga tgtgaatttt tctgttacat    180
gtgtgatccc gaatcgcatc ttccatcacc ctgatcactc tgagtatttt tatgttgatg    240
cagttaatag ggttagacga aaacaagtta tcgatcctga tgatgtattc gttccaaatt    300
gtaacctgca gggtcttatc actccaatgg agaggttacc aaattatggt cagttgtctg    360
agattatttc atcgaacgct cgggatggct tgccatctgc acgcatagca gctacatttt    420
ataacatttc ggtatctcag gctcgtcaag ttaaagctcc acttgaatca tttttgttac    480
ctttgctgtt atctgaaacc tgcccattat cggatgatcc ttgcggattt gacaccacag    540
cttctccccc aatccatgca aatctggcgt tatgggtgct acgtgaaatc agtcggacta    600
tttgtggatc ctcgaaagac cgttcaccct ggttattgct tgattcaggg gtcgcgtggt    660
tcatgtctcc gttaatgtca tcagccattc cgcctctcat ggctgactta acgaatctag    720
caatctataa acaaatttgt tctgtgtcgg acgagcttca ttctcttgcg gttcaagtgg    780
tgttgcaggc tgcagcgtca caatcatatg gccactacat attgcagacg aagtcaatat    840
ttccccagaa tacattgcat aacatgtttc gtacactcac cgatggcatc gttccggtta    900
tagattggct ggaaccgcgt tctaactatc gctttatgct tcaaggtgcg cgtaaagtga    960
cttcagacga tgcgaatcaa gctccggata acacagacgc tgccgagcaa cttggccgta   1020
gaatggggtg ccttgatgtc gtacgctctc tacgcaagat gtcttcatct atcactgtcc   1080
attcacacga tgctatgacc tttgtacgtg atgctatgtc gtgcactagt ggcatattta   1140
```

```
ttacgcgaca acctactgag actgttttaa aagagtacac gcaagcccct accattgaag    1200
ttcctattcc acagtcagat tggtcaccgc ctattggatc tttgcgatat ctctcggatg    1260
cctgctctct ccccgctgta tatttggcta gggcttggcg aagagctgct tctgctgtag    1320
tggataaccc acgtacctgg gacccttat atcaggccat ccttcgctct cagtatgtga     1380
cgtcacgtgg tgggtctggt gctgcgttaa gagatgcttt gaaggctgca gaagttgaac    1440
ttcctcagta tcctggggtc agtgttaagg tggcgaccaa gatttatcag gcggctcaga    1500
ctgcggacgt acctttttgac aagttatctc gggctgttct agctccgttg tcaatgggct   1560
tacgtaacca agttcagcga cgtccaagga ccattatgcc tatgaatgtc gttcaacagc    1620
agatctcagc ggctcacact ctctccgctg actacatcaa ttatcacatg aacttgtcga    1680
cgacatcggg tagcgctgtt attgagaagg tggttccatt aggtatgtat gcgtcctgtc    1740
cccctgctca agcggttaac attgatatca aagcttgtga cgcgtctatc acgtaccagt    1800 atttcttc cgttatagtc ggtgctatc atgagggtgc agcaggccgc cgcgtctcgt       1860
cctcattcat gggagttcca ccaagtgtgc tatctgttgt tgatgctagc ggagtaacgt    1920
cctcaatgcc tatctcaggt ttccaggtta tgtgtcagtg gttggctaag ctctaccagc    1980
gaggttttga gtatcaagta acggacacgt tctcgccagg caatatttc actcatcata     2040 ccactacttt tccctctggc tcaacagcga cgtctacaga acatactgca ataatagta    2100 cgatgatgga tggattttg cgtgcttgga ttccttcctc cggtgcgtct gatgtgctga    2160
agaagttctg caaatccatt tcaatacaac ggaattacgt ttgtcagggt gacgacggtt    2220
taatggtcgt tgatgggcta tcaacaggta aattatcagg cgagataatc gatgaattcg    2280
tcaaagagtt gagagcctat ggtaaatcgt ttgggtggaa ctacgacata gagtttaccg    2340
gaaatgctga gtacctaaaa ttatatttcc taaatggttg ccgtataccg aatgtttctc    2400
ggcatccgat ctgtggcaaa gagcgcgctt caggggataa gttagaaatg tggccatcca    2460
ctattgacat cttcaatggc atatttgtga acgtgtgca tgatggttta ccgtggcgca    2520
gatggttgcg ttattgttgg gctctcgctc tcatgtgttc tgggaaaaacc gtacgtcacg    2580 acgattctga ggtgctgatc caatacccta tgtggtcctt tgtgtattgg ggtttgcctc    2640
ccgtgagtgc gtttgggtct gatccatgga tcttttctcc atacatgccc actggtgatc    2700
atggttttta ctcaatgtta actttagtgc gtcctctgat cactaacttg tcccgtctt     2760 cagacacttc aggattattt tgtcaatgtg atcataacgt cttgttcaac tctgagctgg    2820
tttatcaggg ctattacatg gctcaatgcc cacggcaacc ctctcgttcg aatcgtaggg    2880
atgatcctgg ctctgtacag cgtttcgtta aggctttaga gtcttatctt tatatttccc    2940
ctgagctaaa gtctcgagtg cgacttggtc gcgaccgatg gcaaaagttg gttgggtata    3000
cagaaaaatc tcctccgtcg cttgatgacg tggctttcaa atggtcccgg agtgcacagg    3060
aagctgatct tccaactgct acagagattc aaagcatgga tctggcttta ctggcagcca    3120
gacgtcggac gtatcaaggt ttctccaagt tgttaaacac ctacttgagg gtgacttggg    3180
atttatctga tcctgttgaa cacgctgtag atcctcgtgt tctcttgtgt gctggtgttt    3240
ctccatcgaa tagcgaaccg tttccttaaac tgtactccgt tggtccaatg atgcaatcta    3300
cgcgtaaata tttcagcaat acgctattca tccatcggac tgtgtctggt cttgacgtcg    3360
atgtcgttga tcgtgcgctt ctcaggttgc gtgctcttaa tgcgcctgat gatgtggttg    3420
tggctcaact tttgatggta gggttgtctg aagccgaagc tgctacgttg gcagcgaaaa    3480
tacggacgat ggatattaac gccgtgcaat tggccagagt tgttaatcta tctattcctg    3540
```

```
actcgtggat gaccatggac ttcgatcgct tgatacgaga tatcgtgtct atcactcctc    3600
taaccgtccg gtccctaacc accgatctac cctctggtgt gccgtgggct cgcgcgatac    3660
tgcagttcct aggtgcgggt gttgctatga cggctgttgg acccttgcgt cgtccttact    3720
tgcactcagt tgccggaggt atgtcctcat ttattaagca gttccgccgg tggatgcgtg    3780
ccgaaacgag gtagcgtccg tgctcggcat ggctcgagga attactcatc               3830
```

<210> SEQ ID NO 13
<211> LENGTH: 3907
<212> TYPE: DNA
<213> ORGANISM: Artificial Sequence
<220> FEATURE:
<223> OTHER INFORMATION: Synthetic Sequence

<400> SEQUENCE: 13

```
gcttttccac ccatggctca gattcgaggc cttcggttgt ctacgacact ctcagctcca      60
ccaccaagaa agattgtaac ctcgcatacg tatgatgaac taatctccgc tttaaagctg     120
acaaccaaac cttggcgctc tttaaagtca cgcggcaatg actcaatcac agcagtccgg     180
cttctatttc cccttaatgg ttacattgag cccatgctta tgttagagaa ggacatgaca     240
tacgatgctt ttgagtcttg gattacgccc cttctttctg ctctagctga ccagttgctt     300
agacactacc ctattgctgc ttatcacggg cggttgatta cccgttgtt aaccaatgct      360 gttgttgccg ctttcttatc gaatgtgccc tatgcgcatg cattggatca tcttttttctg   420 gttcgtggga acgttgagga tattatggat gcaggaatca caattcagaa tcatttatgg     480
tttgaccgtg gtgctatagt aactccggcc gggcagaagt tgttcagtt gactggctat      540 aatttttcat ccaatgatcc gtgcttattt tctaagcaat tgcgttgtta tggtcttgtt     600
tactattttc ttaacatgtc cgattgtctg acgtactgtt ggcgtcatct ctctaactcg     660
actcctctga tacattttga tcgtccgtcc aacgggattc attgcttggt gccctccgaa     720
tccacgacac ctatcgccgg ttcattacct gtgtcagctc tcagctccat tctgctggag    780
tcttgtcttc agcaatcctc acttaatgct cttactccta ctggctcacc agtcgttagg    840
caggtggagg tgttgctacc tctatcgtca ccattttttcg aacgtcaaaa tactctggaa    900
tattctcttt ttgctctttc gaatgctctg attaatggtt atcaattcgt tgatttacgt     960
cccggacatc cagattgcgc taccgttgct gctgttttag ctaggttaac tgattttctcg    1020 aaaggtatca ctgttattca accacgccct gctcttctca ctgttaatca tgatagtcct    1080
ctgacgtaca gtggagagaa tgctaatttc atccaacgct tagcttctat gtctggaaga    1140
tctattggtc ccgtcgttat tgggaaatct gtcgatcatg ccgtcggttg gatgcctcag    1200
tttgatcccg ctacatcgta caatcctgat ttatcattag attcactctc acgagctacg    1260
acactgccac tccgtgctaa gtattctact ttctggtctg gccccgcgct cttttccttt     1320
gcttcgtgtg acaggcacaa tggcgtgtat gacattcagt tcatgcccca atttcctcct    1380
acgtatttca gcgatgatga tgccttttct aggtccaggt tttcttccta tcgtgctgtt    1440
aaagatcgat cgttgttaaa agatactgcc aatctgatgt acatttcaaa cttatcgagc    1500
tcgcatgacc atcgtcttgt ccctgattct aagaccatga tttacgtagg gtcttccggt    1560
acgcatgcag ataaccaacc ttccattatt aaacctcttt tagctgggtc tcttccaggt    1620
gttttccgcc cctatccgt gaagcagatt ggttgggagg ttactaacgg gactatttgt     1680
gacattgagc tgcctttagc taccggcaca ttcttcttcg tgtacagtga cgtagaccag    1740
```

```
gttcagtcag gcgattccga cctagacgct tcctcccgac gcttttgctc tcaattggat    1800
atgttaatga aattgacgtt tactggcggt tccttagttg tcaagtgcaa ttttccgact    1860
aacttggttt ggcgtcatat cttttctacc atttctccct atttctcgtc cattcatctg    1920
atgaagcctc ttgtgtcgaa taatttggag ttgtacttat tatttgcaga gcgtttgcct    1980
gtccctgatg ccgcattccg tccgtcggcg gatgttgtcg ttttctggcg atctcaactg    2040
caacgctacc gggtattgcg cgactcattc tctaatgtac cctctatcgg ctctactctt    2100
accttagatg actcattgac tgtatctgtt ctgaattttg tcgatgtcac ttcccttcc    2160 tccattgagg atcaacgagc tttatccgct ttctcagtcc ttacctcctt ggggtctcag    2220
aagttatcgc ttcatcccta ctttgatagt tatcgcacac agctcactgg aataatcact    2280
ccccattctc gtaacatctt aaatagatta gcgtacgtcc cgcgtgtctt cccttcaacg    2340
atcgacgttc aacatcgtgt catggctgcc tcagatcccg agattttgg ttttcgctcc    2400 aattcgtgga ctcaattgtc cttcttctac gatgctacgt tgactgcgac ggattttact    2460
gatgtgaagc attggttgga tctgggaact ggacccgaag cgcgaccgtt gtcttttctg    2520
ccgactgatc ttcctgtcac attgtgcgac actcggcctt tcgttttcc gtctggctgt    2580 tgggccacgt tcactgactt cttaagttat gattacctcg ttacgaacgt cgttttatca    2640
actggtgccg atgttgtgtc ctgcattctc tccctagggg cagcctgcgc tgacgctaac    2700
atgactctac atgagggcgt gcgtcaacta atttcccagt gcgtagatgc tagtgttaaa    2760
acgctgtttt tgcagcttaa ttgtcccctt ccatcagcgg gtgatatgtc tcgggagatc    2820
ctcgagttgg ttcagactaa ttcaacctac gtattccata ccttaggtcg cattgagccg    2880
ttcatcccat attccgctct cttggaaata gtcgaggatt tgtgccctgg catcgtcgtt    2940
gagattaaaa cgatggattc ttctctttca tggcttgact acgctgtcca atctaatgca    3000
tcagtgacgt cggacgacat tgtcttagcg atgcgtttgt ctcacttctg tcctcttttt    3060
gtgtttcatt ttgaccgtca ttctgctcaa ttcccggatg atgcgcgtgt tggtgctccc    3120
ttcaccgtca cattgttgga ttatgaagat actcgatcat atgaggtgac tttagacaat    3180
gtcactattg ctactattac tgcaggcgct ctggtcggat tttcatctgg tgtaagtgtc    3240
acctcatcca acaatcagct ggttatgact attgatcctg cgagtccagg aattctttct    3300
gtcattcagg tactccccgc tcgcatctca ttaggcagct gcgtgataga ggcgccggac    3360
ccatcccttt ctctgatttt tcctgctaca ttagatactt cctgtcagg gaccgacctg    3420 gagttacgtc tgtctgactg gtatgacgtc gctctcttct acgtcgacga agcgcactct    3480
cgactgctgc ccgtatccga taccaagtac gagatttatc gtaaggatca agcgccgaat    3540
agtcgagtaa tcaactatat ctttgatcgt tctgacgtgt tctttaaatt ggtgctgtgc    3600
gacgtctctc catctggaat aggtcgcttc atctatcgtg agttaccgga gctaagttcc    3660
cctgtatggc ctgatgatgc gcgtactttc ttatccatac catttgaatc ccctatggtg    3720
attgtatcgc cggacggacc cgttaactat gacggtgcca atttcactcc tccaacttca    3780
tggcttacag ttgacggcag cacctgcgtc atagatggcc gtccctcatt ttacgtgccc    3840
cctggccgat atggtctggt gagagtctaa acgaccgcgg gcctccagta aagggtgtt    3900 attcatc                                                              3907
```

<210> SEQ ID NO 14
<211> LENGTH: 2283
<212> TYPE: DNA
<213> ORGANISM: Artificial Sequence
<220> FEATURE:
<223> OTHER INFORMATION: Synthetic Sequence

<400> SEQUENCE: 14

```
gctttctcg acatggccta tctagccaca cctgtgctag gagtcggttc tcgtattacc    60
gccttagatc gtactattga tgccatcacg ttgaaacctc gaatcgacct ccaagatgtg   120
tacacaattg atcctacact gactctgcgc cagatagagt taatctcttc gggcacttca   180
atggacgaca ttgctcgtgg attgttgcat cgggactggc gtcgtcaatc taccatcatc   240
ttgcttcctt ctcgtcgttc tcttcttgag tacctattgt caaatccttc tgtctgtcca   300
gacggtttag atcgttctcg acttaaagga ttccaaaagc gtccaaacga ttttcgtgtt   360
caagacttct tttctccact gattacggat tcaacgtcaa ttgctacata ctctcggtgg   420
cttaatgctc atcctattgt gtactctact acttacaagg tcgctggcgc tcgggtgcgt   480
ctctttggac ctgccaaatt gtacattctg tcgcctgatg ctcttcgtga attatccatt   540
ttgaaatcca ctgatcgcat cttcgttgta cctacagcac gtgtatatgt cggttgtttt   600
cctagcgctt ctactagcaa ttgtgtcctt actgcacgcg aacgctggaa tgcccctgac   660
gttcatcccg tcgtaaaagc aatccaatta gcctatgacc atcaatatcg tgtcactgct   720
cgttatctct cagaccctct tatctcagct cttcttcttg ggaaccggtc ggtgaagacg   780
ttgaaggtac agccagtaga agccagagca gcacggtcag ttggcatccg cgttcaagcg   840
atgacacctc ctcgtggtat caacacatca atcatccagg tcgttgatct taagttgcaa   900
tgtcggcatt ccctcattcc caccgaaagg ccattcccac taacgtttat cggcctccca   960
tcctgtttgc ttcaacattt ggatctaaca ttatctgatg attgggtgcc cattcgtgat  1020
catacaggta tgtttgaaat gtggtttatg attcttacgc tcacttgtga caagatcctt  1080
gatggacggg ggaacgctgt ttttctcatt cccagttcta ctaatgcact atcagttaat  1140
tatgtacagc tcacgtcaac tgtatcccca cgtcctcagt cactggcggc taatgcgtcc  1200
gggtggatag attccattgg actgtgtatg cctaaaggtt ctttcaagtc aactatgatt  1260
aaatttctca ctggattgga gatttgtggt acgcgagtaa tgtattcaga cgtcgtgatg  1320
gacagtgatg atgtgggtga tgctttggat cccacttttg agaccgcact atatgacgca  1380
ctgttggctc ttgatccgcc ctttgacgtt gataagttgg ctagtcccac cgatttagtt  1440
gatcaggagt atgtcgcatc tcacatgtac ccaacatttt tacggcttgt caatgagttg  1500
ctaacgccta agcttcaga attatactca gagcgtagtg tggagtttcg gtctcttact  1560
tacgcgcatg ctgactctga atttcttaac gcttgctgga ccgctcgctt gatgcgctgc  1620
ttcatcaact atcacgaaga gcagaatatc ctactccgtc ctggacgcgt tggtggtgtg  1680
ctattccagg tcgcgttgag tcgctgctac aagatgtttg ctacttctac tcctgcttcc  1740
cctctgtcat tgttcctcaa gtcgttgttt gttccttgga ttgaatctgc acctttgtta  1800
gcgagtctga cgccgaacga gtcctctcgt gtgttagcat ggtatattcc ttcctcgtac  1860
tggagtgaca atggctggtg cacttgtgac actcatcgtc acgtcacctt ctctttcatt  1920
cgcggtcttc cagcagacct atcggtgtta gatctgtttg actggtctcg attccgcgcg  1980
actataaacg tagacacgtc tctagtcgag ctaggcgctg acattcgtgc ggttaaggtg  2040
tcggttcatt ggacatccca gaagcccact gtggacgtct ttgacaatcg cgcgcttttc  2100
actcccttcc agcactacca cttgagtctc cattgtaatt gcgcgcctgg tcgccctttt  2160
ttcgcaaaaa atatgaaact gtatctgtcg acggttggag gcgagcactg acgggccgtg  2220
```

| | |
|---|---|
| gggcggtgac acccagggggg ggtatgctgg taaccctggg ttagtcgtct tgagatattc | 2280 |
| atc | 2283 |

<210> SEQ ID NO 15
<211> LENGTH: 2158
<212> TYPE: DNA
<213> ORGANISM: Artificial Sequence
<220> FEATURE:
<223> OTHER INFORMATION: Synthetic Sequence
<400> SEQUENCE: 15

| | |
|---|---|
| gcttttcag tgccagtctt tctcacaaaa tgggaaacgc aacgtctgtc gtgcagaact | 60 |
| ttaacatcca aggtgatggc aatcattttg ccccatccgc tgagactact tcatccgcag | 120 |
| taccctcgtt atctctgaat cctggactgt tgaatccagg tggtaaggcg tgggttctga | 180 |
| ttgactcatc gctaaatgct tcggatcctt catcattaag attgatgact tcggctgatc | 240 |
| tatcgacgct ctctcagtcg ctattggta attctactgg gtctcttctc acctccggta | 300 |
| tgtacgccgt gactgctaaa gagacgttaa gtgtaataac tgagcatgca atttcccagt | 360 |
| ttgataagtt gcaaatggcc tgtgagttgg accgtgatta cctggatgcc agaggcgttt | 420 |
| ctcccgagtc cgtgaatatt cataattaca tcgtctatgt tgattgtttt gtgggtgtgt | 480 |
| ccgcgaggca ggccgcgtcg aatttcagac agcacgtgcc cgttatcaca aaatctcgta | 540 |
| tgacacaatt catgacatct gctcagaacg tgttacaagt gctcggacct tgggaacgtg | 600 |
| acgttcgtga actactcact attcttccca cttctactac cgctggcaag atcacatgcg | 660 |
| acatgaggtc cgttgtcact ttcattgatg atcagctttc cgacaccagt ttatgccgta | 720 |
| tgtaccctga atgtgctgct gcggcggtgg ctagacgtaa tggtggcatc cgatggaaga | 780 |
| cacctgagac cgacgaggct ccttcacttg ctactaatga cattgctgcc tcgaccatgg | 840 |
| gtgcacttgc aaataccacg ccgttagctg agaaatcgaa ttctggtgag aatcaatgc | 900 |
| gcttggtgaa tgatgttggc gtcgatatcg tttgttcccg ggccccgatt agctcctcgg | 960 |
| tctggtcacg tacagttgaa ccgagatcat acaacattag aacacttcgc gtagaagaag | 1020 |
| ctctctggtt gcgtgagtgt caggcaacta ctggctttga cgtgcagtac acgctccctg | 1080 |
| accaagctac tcataaacat ttctggctcc agaagggtc agttgtcatt aatctagagc | 1140 |
| aaacgggcag catgatgttt gatgtaaaca tagcaggtaa agattacaag aagggcactt | 1200 |
| ttaatcctga taatcgtaaa ctagttcttc tggttatgca gtcgaaaata ccttttgaat | 1260 |
| cttggactgt cgcttctcag atcactggta tcgcccaagt ggctgaagtc actgtgcacg | 1320 |
| ccgctgatag ctcgactccc aaccaaaaga taattggtgg gacttcgctg tcgtatctgt | 1380 |
| ttgagagaga gacagtgacc acgtccgata ccgaaatcaa tacataccta ctgtgcactt | 1440 |
| ggcaacttga cgataaacaa agcaatgacg caaatgtctg gccagatgca tgggatggaa | 1500 |
| ttacaacatt gacgccactc acttctggta ccgtaactat taaggggact tcggtggact | 1560 |
| ctgtcgtacc gtctgatctc gttggcgctt atactcctga gtccttggcc gctgcacttc | 1620 |
| ctaatgatgc tggtttgatc ttggctaaca aagcaactaa actggctgac gctatcaaaa | 1680 |
| aagaggatga ctctgtggtc gatgagtctt ctcccttag cactcctatt caagggtcc | 1740 |
| tggccgttca acaacttgac accgtaggga cacgtggagc acgcgcactc caacctcctt | 1800 |
| cgattctgaa gcgcattgct tcgcgagctc ttcacatgtt cttgggtgac ccgcgttcca | 1860 |
| ttttgaaaca ggcgataccc gtgttgagag accctgacgt atggactggt tttgtccaag | 1920 |
| gcgttagaga tggcattcgg actaagtcgt tgtccgctgg ggtgcggtcg gtgtacaaca | 1980 |

| | | |
|---|---|---|
| acgttaccgc cacgcaatct gtccaaacat ggaagcaggg gttcctgaca aaaatacaga | 2040 | |
| cgttgttcaa accatcgtga ggtgctaagg cctctctcta cggcgggtcg gtgggcacgt | 2100 | |
| cgtggtgatg ctgaatgcac ggggaggtga cgctccctgg attggcacgt tattcatc | 2158 | |

<210> SEQ ID NO 16
<211> LENGTH: 1996
<212> TYPE: DNA
<213> ORGANISM: Artificial Sequence
<220> FEATURE:
<223> OTHER INFORMATION: Synthetic Sequence

<400> SEQUENCE: 16

| | |
|---|---|
| gcttttgag tcctagcgtg gatcatggcg tcaaccaagt ggggagacaa gccgatgtcg | 60 |
| ctctcaatgt ctcacgatgg atcatctatc cgcagtgctg cctcacaatt cttatcggtt | 120 |
| cctctgtctc actcaacgcc tatcccacct caacggaaga ctgtgctgtt gaagtttatg | 180 |
| attggtgacg aactggttac cgttcagggt gctctcgctc cgttcgacga atattggtat | 240 |
| gacaaccagc ccctgttagc tcaggctgtt gagatgctcg cctctgcaga tcgtttgcgt | 300 |
| caatttgagc attatgagaa attcctactc aagaaaggtc accagataac tgagatcatg | 360 |
| aacaggttac gtctctttt tacggatgtt ctcaaagtta agatggaagc tgacgcttta | 420 |
| cccgctttag cccaatatct gatggttgga accttggagg ctgtttccac cgctgattcc | 480 |
| cccgatgcct gcgtcccagt cacctcaaag atcttagcta agcagcagac tattgctaag | 540 |
| tctcctggac gtctcgacga ggaagaatat aatgttattc gatcacgttt cctcacgcat | 600 |
| gaagtcttcg acttaacgtc cgatttaccc ggagtacaac cgtttatgga catgtactac | 660 |
| gccactgtcc cccgtgctga ttctacagga tggtgtgtgt atcgtcgaaa gggtctgctt | 720 |
| atctacgctc ctgatgagca attctcggat ctgactatct tctccacacg tcttactgca | 780 |
| tcacgtgagc tgcagcttgt ggctggagat gttgtcgtag cctgctttga tctcatggac | 840 |
| gtctctgaca ttgctccatc tcatcatgca tcagtgcagg aagagcgtac tctcgggacc | 900 |
| agtaagtatt cgaatgtgac ggctaatgat catcctctgg tattcttctc acccagtgcg | 960 |
| ctccgttggg caattgacca tgcttgtact gactccttgg tttctacccg gaatattcgt | 1020 |
| gtctgcgttg gcatcgatcc tctggtaact cggtggaccc gagatggtgt gcaagaggct | 1080 |
| gctattctca tggatgacaa gctaccctca gcaggtcgtg cgcgtatggc gttgcgaaca | 1140 |
| ttgcttctcg ctagacggtc tccaatgcca tccttcttac tcggtgcgct aaaacagtca | 1200 |
| ggcggtcagt tactggagca ctaccgatgc gatgcagcta atagatatgg atctcccacc | 1260 |
| gttccgatct cccatccgcc accatgctca aagtgtcctg agctaaaaga acaaattgcc | 1320 |
| aagctctcgt catcgcctat acccaaagtc gattcgtccg ttggtccagc cgtactgctg | 1380 |
| tctaaaattg ctgaccttca gcgtgctaat agagaactgt cactgaaact ggttgatgtt | 1440 |
| caacctgctc gggaagatca cttgttggct tatctcaatg aacacgtgtg tgtaaacgct | 1500 |
| aaagatcatg aaaagggcct gctcgctcgt tgtaacgtat ctggtgattc aatctcctct | 1560 |
| atccttggcc agcgcatgaa gaatcgggaa aggtttgaaa ctcgactgcg tcatgaggct | 1620 |
| agtgctgagt gggaaccccg tgtggaagcg ttaaccaag aattggctaa agctcgtgtc | 1680 |
| gaacagcagg acatgatgac tcaatcccta cagtacctga acgagcgtga tgaactactc | 1740 |
| caggaagtgg atgagcttaa gcgtgagctg actaccctgc gttccgctaa cgtacgcttg | 1800 |
| aatgctgaca tcatcggat gagtcgtgcg acacgtgtcg gagacgcctt cgtcagtgac | 1860 |

```
gtcgagccgc taccctctgg cataccyggt gaatcgaaac catctatgga agaattggtg   1920
gatgatctgt gagctttgac ctgtgactcg acttctctct gattccatgt acccacggcg   1980
gactcggtta ttcatc                                                    1996
```

<210> SEQ ID NO 17
<211> LENGTH: 1643
<212> TYPE: DNA
<213> ORGANISM: Artificial Sequence
<220> FEATURE:
<223> OTHER INFORMATION: Synthetic Sequence

<400> SEQUENCE: 17

```
gcttttttcaa tcccttgttc gtcgatgctg cgtatgcctc ccggttcgtg taacggtgcg     60
actgctgtat ttggtaacgt tcattgtcag gcagctcaaa acacggcagg tggtgatttg    120
caagctacgt catccataat tgcatattgg ccttatctag cggcgggtgg tggtttctta    180
ttaattgtta tcattttcgc tcttctatac tgttgtaagg ctaaggtcaa ggcggacgct    240
gcacgtagtg tcttccatcg tgagctagta gcgttgagtt ctggtaagca caatgcaatg    300
gctccgccat acgacgtttg aagtgcaacg atttaatttc tgtccgctat cacttcgcga    360
acttgctatc ccatcattta ctgctataac tggggctgac ccatcacagt attttaacat    420
tgagctccca cacactcatc ctctctattc caaattgcct actctgttat ctcaaccttg    480
tagggtccac gtgcggctga ttcgccggtt cgctctctat tcaacattgt caagtatttg    540
tgagtacgat tgtgctgtac tattctcccc acacgctatc gttccattgc ctgcatccga    600
tcggcggtct tgtcttatag ttcattggga tggcgggtct caatccatcg cagcgaagag    660
aggtcgtcag cttgatactg tcattgactt cgaacgtgac tataagtcat ggcgatttga    720
cgccgatcta tgaacggctg accaatctag aagcgtctac ggagttatta catcgctcca    780
tttccgatat atccactact gtctcaaata tttctgcaag tttacaagac atgacccata    840
ccttggatga tgtaactgct aatttagacg gtttgaggac cactgttact gcacttcagg    900
attccgtctc cattctgtct acaaatgtga ctgacttaac gaacacatcc tctgcgcacg    960
cggcgacact atcttcactt caaactacgg ttgacgaaaa cttcactgcc atctccaatt   1020
tgaagagtga tgtatcgtcg aacggtttag ctattacaga tctgcaggat cgtgttaaat   1080
cattggagtc taccgcgagt catggtctat ctttttcgcc tccacttagt gtcgctgacg   1140
gcgtggtttc attagacatg gaccectact tctgttctca acgagtttct ttaacatcat   1200
actcggcgga ggctcaacta atgcaatttc ggtggatggc acggggtact aacggatcat   1260
ctgataccat tgacatgacc gttaacgctc actgtcatgg aagacgcact gattatatga   1320
tgtcgtccac gggaaatctc acggtcacta gtaacgtcgt gttattaacc ttcgatttaa   1380
gttacataac gcctatccca tcagacctag cacgtcttgt tcccagtgcg ggattccaag   1440
ctgcgtcgtt ccctgtggac gtatcattca cccgcgattc tgcgactcat gcgtaccaag   1500
cgtatggggt gtactcgagc tcacgtgtct tcacaattac tttcccaacc ggaggtgatg   1560
gtgcagcgaa cattcgttcc ttgaccgtgc gtaccggcat cgacacctaa ggtgtggcgc   1620
cgtacgggga ttggttattc atc                                           1643
```

<210> SEQ ID NO 18
<211> LENGTH: 1324
<212> TYPE: DNA
<213> ORGANISM: Artificial Sequence
<220> FEATURE:
<223> OTHER INFORMATION: Synthetic Sequence

<400> SEQUENCE: 18

```
gcttttctc ccacgatggc gcgtgccata tacgacttct tttcaacgcc tttcgggaat    60
cgtggtctag cgacgaatcg tactcaactg tcatcactac tatcgagctc gaattcccca   120
tggcaacggt ttctatcatc aatgactcca ttgacagcgc caggtatcgt ttcaacgcct   180
gaagcaccct atccaggttc gttgatgtat caagagtcta tgctccacag tgctactgtc   240
cctggagtac tcggtagtcg tgatgcttgg cgtacattta atgtcttcgg gctttcgtgg   300
actgatgaag gattgtcagg actagtagct gcccaagatc ctcccctgc cgccccgtat    360
cagccagcct ctgctcagtg gtcggatctc tcaactacc ctagatgggc aaacagacgt    420
cgtgagctgc aatctaaata cccacttctg cttcggtcca cgctgctttc tgccatgcga   480
gctggtcctg ttctctacgt tgagacgtgg ccgaatatga tctcaggacg attagctgac   540
tggttcatgt cccaatatgg caacaatttc gttgacatgt gcgccaggtt gacccagtct   600
tgttcgaaca tgcctgttga gcctgatgga aattatgatc agcagatgcg tgctttaatt   660
agtttgtggc ttctttcata cattgggtg gtcaatcaga ccaacaccat cagcggcttc    720
tacttctcct cgaagactcg gggtcaagcg ttggacagtt ggactttatt ctacactaca   780
aacactaatc gtgttcaaat tacgcagagg catttcgctt acgtgtgtgc tcggtctccc   840
gactggaacg tggataaatc atggatcgct gcagcgaact taaccgctat cgtcatggct   900
tgccgtcaac cgccggtgtt cgccaatcaa ggcgttatta accaagcgca gaaccgacct   960
ggcttttcca tgaatggggg gacgcccgtc catgagctca acttactgac taccgcgcag  1020
gaatgtattc ggcagtgggt gatggccggt ttggtgtcag cagcgaaggg gcaagcctta  1080
acgcaggagg ctaatgactt ctcaaacctc atccaggcgg atctaggaca aatcaaagcg  1140
caggatgatg ctctgtacaa ccagcagcca gggtacgcga ggagaataaa acccttcgtt  1200
aacggtgact ggacaccagg tatgaccgcg caagctctgg ccgttctagc cacttttacc  1260
gcctaggcgt agggtcgtac gctgcccgag tccagccctc cggcagcacg tggatgtatt  1320
catc                                                               1324
```

<210> SEQ ID NO 19  
<211> LENGTH: 1202  
<212> TYPE: DNA  
<213> ORGANISM: Artificial Sequence  
<220> FEATURE:  
<223> OTHER INFORMATION: Synthetic Sequence

<400> SEQUENCE: 19

```
gcttttgag tccttagcgt gcaagccgca atggaggtac gtgtgccaaa ctttcactcg     60
ttcgttgaag gaataacatc tagctatttg aagactcctg cttgctggaa tgcacagaca   120
gcctgggaca ctgtgacttt tcacgtccct gatgtaatta gagttggcaa tgcgtattgt   180
tgctctcaat gttgtggtgt actttattac gggactctgc ccgcggatgg aaattacttc   240
cctcatcaca aatgccatca gcaacagtac aggaccgata ccccactgct ccggtatgtg   300
cgaattggca gaacgactga gcatctgttg gaccaatatg ctgttgcgct ggagtctatt   360
gctgatcact atgatgaaat cagtcaacgc atggtcgatg agccagagaa cgatgaagtc   420
gcgccccttg acattgtaac gcgtactgaa tctatccgaa gtgataagac ggttgacccg   480
gacttttgga cttacccgct tgagcgacgt tctgatgatt tctgtcgaga catcgccgca   540
tcatgctgga gaatgattga tgcatcatca cgtagtctca ctcttccaaa ttgtcttgtg   600
```

```
tccccgtctt tgcattctcg ttccgtctt ggtcaaatgc aaacgaccac caccatatac    660
gatgttgcgg cgtcgggaaa ggccgttaaa tttctccga tggtggctac actatcgcaa    720
cgtgatgctg gccctgtaaa gcttgcgaat gctgacccag cggaaggtgt atattcattt   780
tggacgtcgc acttcgcctt ctcaccgctc attggtggag ttgggattac gggacagtac   840
gctcgtgagt cataccatca cgtgggtcat ccagtgattg ggagtggtaa aaggcgtca    900 cactacaaaa atctgtttat ggaatcatgg cgtgggtggt caaagtcagc tttcgcatgc   960
gctacaggaa tggagccagc tgaatgtgaa tctcgtctga ggggacatgc tcgcactatg  1020
cttggacgct ctctgccgaa cgtctgtgac gacgaggttg ctcagcagtc tggcgccgtg  1080
ctaacgtccc tgcagaagac taccaagttc actgttgtgg agtgtggttg gtaagtacct  1140
ccgggtcaaa atgcacatag gctcccacct atgtgacggt tagcgggact cgcctattca  1200
tc                                                                 1202
```

<210> SEQ ID NO 20
<211> LENGTH: 1192
<212> TYPE: DNA
<213> ORGANISM: Artificial Sequence
<220> FEATURE:
<223> OTHER INFORMATION: Synthetic Sequence

<400> SEQUENCE: 20

```
gcttttgag tccttgtgca gccatggaca acaccgtgcg tgttggagtt tcccgcaaca     60
catccggcgc agctggtcag acactcttta gaaacttcta tttactacga tgtaatattt   120
cagctgatgg ccgtaatgca acgaaggcgg tacaatccca ctttccattc ctttcacgtg   180
ctgtgcgatg cctatcgcct cttgccgctc actgtgctga tagaacccct cgccgtgaca   240
acgtgaaaca gattcttact cgtgaactgc cattttcctc ggatctaatc aactacgcac   300
accatgtcaa ttcatcatcc cttactacct ctcaaggcgt cgaagcggct cgtttggtag   360
ctcaagttta tggggaacaa gtaccgttcg atcacattta tcctactggt tcagcgacat   420
actgtcctgg tgcaatcgca aatgctattt ctcgcattat ggctggcttt gtacctcgtg   480
aaggtgatga ctttgctccg agtggcccta ttgactacct cgctgctgac ctgatcgcgt   540
ataagtttgt gctcccttac atgcttgaca tggtagatgg tcgtcctcag attgtcctgc   600
cgtctcatac cgtagaagaa atgttgacca acaccagctt gctgaactcg attgatgctt   660
catttggtat cgaagcgcgc agtgatcaaa ggatgactcg tgatgctgct gagatgagtt   720
ctcgctccct caatgaactt gaggatcatg atcagagagg tcgtatgcct tggaagatca   780
tgctagcgat gatggcggcc caattgaagg ttgagttgga cgcgctggcg gacgagcgta   840
cggagtcaca agctaatgct cacgttacat ccttcggatc ccgtttattt aatcagatgt   900
cggcgtttgt tactattgat cgtgaactga tggaactggc ccttctcatc aaggaacagg   960
gcttcgccat gaatccgggt cagattgcat ctaagtggtc gctgatacgt cgttccggtc  1020
ctactcgtcc actttcaggt gcccgtcttg aaatcaggaa tggtaattgg atgatccgtg  1080
agggtgacca aacgctactg tctgtctctc cagctaggat ggcgtagacg ggacccatgg  1140
tgcgggtgag ggtcgccac accctctgcc gcgacttgga ctcttattca tc           1192
```

<210> SEQ ID NO 21
<211> LENGTH: 3959
<212> TYPE: DNA
<213> ORGANISM: Artificial Sequence
<220> FEATURE:
<223> OTHER INFORMATION: Synthetic Sequence

<400> SEQUENCE: 21

```
gctttttctc cgaacgccga aatgagttcg cgcaaagtgg ctagacgtcg tcataaggat      60
gctactgaat ctaaggacac taaagacact aataaatcta agccatcttc tattgatgct     120
aaagaatcta cggatagcgc tacgataag aaagtcactg ctccaccacc aaataatccg      180
gctgcttcta ctccctcctc cactgatggg gcttcccaaa catctgtcgc taagcagacg     240
aatgataatg acgcctcagt taaggaatca gctcccaagc ctactgtctc agcgacggg      300
aaagatggga tgcacggtgc tgtgaagtcg caagacgcta aggctaccgt agctgtagat     360
aataataagg atagagatgt agtatttggt ggtgcaggtt ctggtgacaa aaatgctatc     420
acgaaaactg gctccgttga caatgatggg ggtgttaagg tcgttccagc caaggatgct     480
acgatatctt cggccaaagc catgatggag caaaagcagt tagtcgctgg tcttccgaaa     540
caaccgaagt ctgctaatca tctgtgtacc gtctgcatgg ctcagtttgc gtcagctgac     600
gctcttacta ttcaccaaac tacgcattct attggttcca acgcggctct gacgagtttt     660
tcgatctcta ctgctgttga agaattcatt caatcatggg ctgctgccac atccacggct     720
aacaccaaga cggcttttgac tgtgtctgac gttgactcac tgatgatgac tgaaggaata     780
cgccttataa cttgggattc tgggttatgc acgtcttttg agcttgtccc gatcgtccat     840
tcaaacactg ttcaagatgt tatttcatat tcatggttta cgtcaagcta taacatcacg     900
actcccttcc cacaagcgac tgtcgtgcgg attgtcttgc gtactaactg ggctgccaaa     960
ttggattctc cctcttcgtc gcgtgaatgt gatcttcgtc ttgctccacc tacagagagc    1020
aatgctcgat cattctcaat gctactcaat acgggtgcga ctccagaagg cacttttcaac   1080
cccaacaccc ttcgtatgaa cgtgctgcag atgtgtcttc agtatgttct agctaacttg    1140
cacctgaacc gtagcactca gtttaccatg gatttgactg ccgcggctcc caatctatct    1200
gcgtctcaac tccgtatcgt tccagaggat aaggagggta atggtttcc tgtcatgtat     1260
ccatcccgag tgaacatccc actgttcaac aagacggctg atttttgttaa tcagtgcatt    1320
cgtgatagag ttggtcgata cgatcgcgcc cagacttttg ctggtgcacc ttctgaatgg    1380
gctgacatgt gggaaacagc agacgcgtta actctctccg tccgtgaaat gtggatgtca    1440
cgcatttctc aaatgaacat tactcccgct gatattgctg acgctatctc cagatgttct    1500
cagtctttgc tcactgttgc cgcgccgaca gctccttctg tggctcgttt gttaccttgg    1560
cgggttagtt ctgatgagag gcagctgctc caactgctga tgtacttaaa tgttggtact    1620
agtgctgact acgttcaacc gattctttct gcgttcgctc gaactctgtc tcgtgtgtca    1680
ccactgcgaa ttaatcctac cctaatcgct aatgctatgt cgacaattgt cgagagcact    1740
actaatactc agagtcctgc tgcggctatc ttgtcaaagc ttaaacctgt cgcatctgat    1800
ttttccgact ttaggttggc atgtgccgct tggttatata atggttgtgt ccagacatac    1860
ttgtctgagg attcgtatcc gagcagcggt gggtctgtca ctagcatcga cacgttgatt    1920
gatatgtttg tgtgtttgct ggcgttgcct ctggttactg atcctaacgc tccttgtcaa    1980
gcctttatgg ttgtcgctaa tgctatggtt ggttacgaga acctgcctat ggacgaccct    2040
aattttactc agcagagact ggctgcagcg ttcaataatc ctactacctg gcctcaatgc    2100
ttcctccacc ctcaaaatat tgatcggcgc cagtgtccga ttctttcatg gtgggctcag    2160
cagattcatc gtaattggcc tacaccatct cagattactt atggtgcgcc tgatatcatc    2220
ggctccgcta acttgttcac tccccctgat gtgttgctgc ttccattaca acataggccc    2280
```

-continued

| | |
|---|---|
| atccgtatca ccaatcccac cctgaacttc gataatgagt tgacgacttg gcgtaacacc | 2340 |
| gtggttgatt tagtcctgcg cattattgac agtggtcggt accagcctaa ttggaatcag | 2400 |
| tctattcgtg cgtctatgcg gaatgcgatg acgaatttca ggattattaa gtcctataca | 2460 |
| cctgcttaca tagcggaatt gctacctgtg gaactggcgg ctatcgctcc aactctaccc | 2520 |
| ttccagcctt tccaggtgcc gtttgctcgc ttagatcgtg acgctatcgt cacccatgtc | 2580 |
| aatgtgtcca gacaagctcc caacaatctt gctcaacctg cattgaacat gtccatgacg | 2640 |
| taccagcgca caggagttcc aatctctctt agtgcccgtc ccttggccgt cgctctttta | 2700 |
| tcaggtcagt atcctactga tcctcctctt cagaccaatg tttggtacgt gaacactctc | 2760 |
| acacctctat attccaatga tggtctcttt aacaacgtgc agcatgctat ggttgcttct | 2820 |
| gaagcttacg caactttgat cactatgctg gctcagtgca ctgacatgca gtaccccgtg | 2880 |
| gatcggccat tgaactggct tcgtcagatt aatttggctg ccaatgaagc gacgattttt | 2940 |
| ggtcgctcaa ttaactcact tttccaaacc gcttttgacc tctcaccctc tactgtgttg | 3000 |
| cttcagcctt tcttggagtc tgatccacgt gcaacgcagc tcgccatttc ttacgtccgt | 3060 |
| tataatggtg atagtgagac cttcgtgcca acagtgcgtc cgtctatgat ctcagaggcg | 3120 |
| acattgctcg ttgagcgtac tctctcgcac gaatacaacc ttttcggttt atgtcgcggt | 3180 |
| gacatcattc tggggcagca catgactcct actgcgttca atcctctggc tccgcctccc | 3240 |
| tctgtcattt ttaatagggg tgatgctgac gtttatgagt ttggcccacg tagcttcgcc | 3300 |
| aacttcggta tgaatgggga ggagatcttg gtcatggatg cgaacggcgt gcgtcgtcca | 3360 |
| ttacttggcc gttgggttat gccactgcag cttctgatgg tgaatattgg cgtcttcc | 3420 |
| aagttgttgt tggatcgtat cttgaaggga cgcttataca tccgacttga agttggcgcg | 3480 |
| tatccctaca ctgtgcagta ttaccaggga cgtgagttca cagatggttt cactctgctt | 3540 |
| gagcaatgga tgtctaaggt gtcacccatg gtatccctc ccgtccctt cctcatgcca | 3600 |
| cagtccgaag gacacaacat cacttcaggc atggttactc attacatctg gtccactgaa | 3660 |
| tacaatgacg ggtcactctt cgccacgaac actgacctgc cggttactgt gtttggtcct | 3720 |
| gaccgtacca tcccaatcga acgctaccgg gcactcgttg atccaggcgc tcttcctgct | 3780 |
| accaaccaac tgccgcacac catcgacctt tactgctcac tgagacggta ttatctggaa | 3840 |
| acacctccta tcaccgctac tgttaccact atggcgatg gactccccgc gctgaaccat | 3900 |
| tagagcggcg aggctagacg cgagttgatc gcgtcgactc tcgttggaga ttattcatc | 3959 |

<210> SEQ ID NO 22
<211> LENGTH: 3830
<212> TYPE: DNA
<213> ORGANISM: Artificial Sequence
<220> FEATURE:
<223> OTHER INFORMATION: Synthetic Sequence

<400> SEQUENCE: 22

| | |
|---|---|
| gcttttcct caccatgcat gtcaacgggt ttgatgatgc tactctctct tacgcacaat | 60 |
| ccatctcggg ggttattcca atgacaaata agttatttga gcaagcatct gcatcgatac | 120 |
| gtgccttacc gcgctcacac gtttatgctc tattagatga tgtgaatttt tctgttacat | 180 |
| gtgtgatccc gaatcgcatc ttccatcacc ctgatcactc tgagtatttt tatgttgatg | 240 |
| cagttaatag ggttagacga aaacaagtta tcgatcctga tgatgtattc gttccaaatt | 300 |
| gtaacctgca gggtcttatc actccaatgg agaggttacc aaattatggt cagttgtctg | 360 |
| agattattc atcgaacgct cgggatggct tgccatctgc acgcatagca gctacatttt | 420 |

```
ataacatttc ggtatctcag gctcgtcaag ttaaagctcc acttgaatca tttttgttac    480
ctttgctgtt atctgaaacc tgcccattat cggatgatcc ttgcggattt gacaccacag    540
cttctccccc aatccatgca aatctggcgt tatgggtgct acgtgaaatc agtcggacta    600
tttgtggatc ctcgaaagac cgttcaccct ggttattgct tgattcaggg gtcgcgtggt    660
tcatgtctcc gttaatgtca tcagccattc cgcctctcat ggctgactta acgaatctag    720
caatctataa acaaatttgt tctgtgtcgg acgagcttca ttctcttgcg gttcaagtgg    780
tgttgcaggc tgcagcgtca caatcatatg ccactacat attgcagacg aagtcaatat    840
ttccccagaa tacattgcat aacatgtttc gtacactcac cgatggcatc gttccggtta    900
tagattggct ggaaccgcgt tctaactatc gctttatgct tcaaggtgcg cgtaaagtga    960
cttcagacga tgcgaatcaa gctccggata acacagacgc tgccgagcaa cttgccgta   1020 gaatggggtg ccttgatgtc gtacgctctc tacgcaagat gtcttcatct atcactgtcc   1080
attcacacga tgctatgacc tttgtacgtg atgctatgtc gtgcactagt ggcatattta   1140
ttacgcgaca acctactgag actgttttaa aagagtacac gcaagcccct accattgaag   1200
ttcctattcc acagtcagat tggtcaccgc ctattggatc tttgcgatat ctctcggatg   1260
cctgctctct ccccgctgta tatttggcta gggcttggcg aagagctgct tctgctgtag   1320
tggataaccc acgtacctgg gacccttat atcaggccat ccttcgctct cagtatgtga    1380
cgtcacgtgg tgggtctggt gctgcgttaa gagatgcttt gaaggctgca gaagttgaac   1440
ttcctcagta tcctggggtc agtgttaagg tggcgaccaa gatttatcag gcggctcaga   1500
ctgcggacgt acctttgac aagttatctc gggctgttct agctccgttg tcgatgggct    1560
tacgtaacca agttcagcga cgtccaagga ccattatgcc tatgaatgtc gttcaacagc   1620
agatctcagc ggctcacact ctctccgctg actacatcaa ttatcacatg aacttatcga   1680
cgacatcggg tagcgctgtt attgagaagg tggttccatt aggtatgtat gcgtcctgtc   1740
cccctgctca agcggttaac attgatatca aagcttgtga cgcgtctatc acgtaccagt   1800
attttctttc cgttatagtc ggtgctattc atgagggtgc agcaggccgc cgcgtctcgt   1860
cctcattcat gggagttcca ccaagtgtgc tatctgttgt tgatgctagc ggagtaacgt   1920
cctcaatgcc tatctcaggt ttccaggtta tgtgtcagtg gttggctaag ctctaccagc   1980
gaggttttga gtatcaagta acggacacgt tctcgccagg caatattttc actcatcata   2040
ccactacttt tccctctggc tcaacagcga cgtctacaga acatactgca aataatagta   2100
cgatgatgga tggattttg cgtgcttgga ttccttcctc cggtgcgtct gatgtgctga    2160
agaagttctg caaatccatt tcaatacaac ggaattacgt ttgtcagggt gacgacggtt   2220
taatggtcgt tgatgggcta tcaacaggta aattatcagg cgagataatc gatgaattcg   2280
tcaaagagtt gagagcctat ggtaaatcgt ttgggtggaa ctacgacata gagtttaccg   2340
gaaatgctga gtacctaaaa ttatatttcc taaatggttg ccgtataccg aatgtttctc   2400
ggcatccgat ctgtggcaaa gagcgcgctt cagggataa gttagaaatg tggccatcca    2460
ctattgacat cttcaatggc atatttgtga acggtgtgca tgatggttta ccgtggcgca   2520
gatggttgcg ttattgttgg gctctcgctc tcatgtgttc tgggaaaacc gtacgtcacg   2580
acgattctga ggtgctgatc caatacccta tgtggtcctt tgtgtattgg ggtttgcctc   2640
ccgtgagtgc gtttgggtct gatccatgga tcttttctcc atacatgccc actggtgatc   2700
atggttttta ctcaatgtta actttagtgc gtcctctgat cactaacttg tccccgtctt   2760
```

| | |
|---|---|
| cagacacttc aggattattt ggtcaatgtg atcataacgt cttgttcaac tctgagctgg | 2820 |
| tttatcaggg ctattacatg gctcaatgcc cacggcaacc ctctcgttcg aatcgtaggg | 2880 |
| atgatcctga ctctgtacag cgtttcgtta aggctttaga gtcttatctt tatatttccc | 2940 |
| ctgagctaaa gtctcgagtg cgacttggtc gcgaccgatg gcaaaagttg gttgggtata | 3000 |
| cagaaaaatc tcctccgtcg cttgatgacg tggctttcaa atggttccgg agtgcacagg | 3060 |
| aagctgatct tccaactgct acagagattc aaagcatgga tctggcttta ctggcagcca | 3120 |
| gacgtcggac gtatcaaggt ttctccaagt tgttaaacac ctacttgagg gtgacttggg | 3180 |
| atttatctga tcctgttgaa cacgctgtag atcctcgtgt tcccttgtgt gctggtgttt | 3240 |
| ctccatcgaa tagcgaaccg tttcttaaac tgtactccgt tggtccaatg atgcaatcta | 3300 |
| cgcgtaaata tttcagcaat acgctattca tccatcggac tgtgtctggt cttgacgtcg | 3360 |
| atgtcgttga tcgtgcgctt cttaggttgc gtgctcttaa tgcgcctgat gatgtggttg | 3420 |
| tggctcaact tttgatggta gggttgtctg aagccgaagc tgctacgttg gcagcgaaaa | 3480 |
| tacggacgat ggatattaac gccgtgcaat tggccagagt tgttaatcta tctattcctg | 3540 |
| actcgtggat gaccatggac ttcgatcgct tgatacgaga tatcgtatct atcactcctc | 3600 |
| taaccgtccg gtccctaacc accgatctac cctctggtgt gccgtgggct cgcgcgatac | 3660 |
| tgcagttcct aggtgcgggt gttgctatga cggctgttgg accctcgcgt cgtccttact | 3720 |
| tgcactcagt tgctggaggt atgtcctcat ttattaagca gttccgccgg tggatgcgtg | 3780 |
| ccgaaacgag gtagcgtccg tgctcggcat ggctcgagga attactcatc | 3830 |

<210> SEQ ID NO 23
<211> LENGTH: 3907
<212> TYPE: DNA
<213> ORGANISM: Artificial Sequence
<220> FEATURE:
<223> OTHER INFORMATION: Synthetic Sequence

<400> SEQUENCE: 23

| | |
|---|---|
| gcttttccac ccatggctca gattcgaggc cttcggttgt ctacgacact ctcagctcca | 60 |
| ccaccaagaa agattgtaac ctcgcatacg tatgatgaac taatctccgc tttaaagctg | 120 |
| acaaccaaac cttggcgctc tttaaaatca cgcggcaatg actcaatcac agcagtccgg | 180 |
| cttctatttc cccttaatgg ttacattgag cccatgctta tgttagagaa ggacatgaca | 240 |
| tacgatgctt ttgagtcttg gattacgccc cttctttctg ctctagctga ccagttgctt | 300 |
| agacactacc ctattgctgc ttatcacggg cggttgatta cccgttgtt aaccaatgct | 360 |
| gttgttgccg ctttcttatc gaatgtgccc tatgcgcatg cattggatca tcttttttctg | 420 |
| gttcgtggga acgttgagga tattatggat gcaggaatca caattcagaa tcatttatgg | 480 |
| tttgaccgtg gtgctatagt aactccggcc gggcagaagt tgttcagtt gactggctat | 540 |
| aatttttcat ccaatgatcc gtgcttattt tctaagcaat tgcgttgtta tggtcttgtt | 600 |
| tactattttc ttaacatgtc cgattgtctg acgtactgtt ggcgtcatct ctctaactcg | 660 |
| actcctctga tacattttga tcgtccgtcc aacgggattc attgcttggt gccctccgaa | 720 |
| tccacgacac ctatcgccgg ttcattacct gtgtcagctc tcagctccat tctgctggag | 780 |
| tcttgtcttc agcaatcctc acttaatgct cttactccta ctggctcacc agtcgttagg | 840 |
| caggtggagg tgttgctacc tctatcgtca ccatttttcg aacgtcaaaa tactctggaa | 900 |
| tattctcttt ttgctctttc gaatgctctg attaatggtt atcaattcgt tgatttacgt | 960 |
| cccggacatc cagattgcgc taccgttgct gctgtttag ctaggttaac tgatttctcg | 1020 |

```
aaaggtatca ctgttattca accacgccct gctcttttca ctgttaatca tgatagtcct   1080
ctgacgtaca gtggagagaa tgctaatttc atccaacgct tagcttctat gtctggaaga   1140
tctattggtc ccgtcgttat tgggaaatct gtcgatcatg ccgtcggttg gatgcctcag   1200
tttgatcccg ctacatcgta caatcctgat ttatcattag attcactctc acgagctacg   1260
acactgccac tccgtgctaa gtattctact ttctggtctg gccccgcgct ctttccttt    1320
gcttcgtgtg acaggcacaa tggcgtgtat gacattcagt tcatggccca atttcctcct   1380
acgtatttca gcgatgatga tgccttttct aggtcaaggt tttcttccta tcgtgctgtt   1440
aaagatcgat cgttgttaaa agatactgcc aatctgatgt acatttcaaa cttatcgagc   1500
tcgcatgacc atcgtcttgt ccctgattct aagaccatga tttacgtagg tcttccggt    1560
acgcatgcag ataaccaacc ttccattatt aaacctcttt tagctgggtc tcttccaggt   1620
gttttccgcc ccctatccgt gaagcagatt ggttgggagg ttactaacgg gactatttgt   1680
gacattgagc tgcctttagc taccggcaca ttcttcttcg tgtacagtga cgtagaccag   1740
gttcagtcag gcgattccga cctagacgct tcctcccgac gcttttgctc tcaattggat   1800
atgttaatga aattgacgtt tactggcggt tccttagttg tcaagtgcaa ttttccgact   1860
aacttggttt ggcgtcatat cttttctacc atttctccct atttctcgtc cattcatctg   1920
atgaagcctc ttgtgtcgaa taatttggag ttgtacttat tatttgcaga gcgtttgcct   1980
gtccctgatg ccgcattccg tccgtcggcg gatgttgtcg ttttctggcg atctcaactg   2040
caacgctacc gggtattgcg cgactcattc tctaatgtac cctctatcgg ctctactctt   2100
accttagatg actcattgac tgtatctgtt ctgaattttg tcgatgtcac ttcccttcc    2160
tccattgagg atcaacgagc tttatccgct ttctcagtcc ttacctcctt ggggtctcag   2220
aagttatcgc ttcatcccta cttgatagt  tatcgcacac agctcactgg aataatcact   2280
ccccattctc gtaacatctt aaatagatta gcgtacgtcc cgcgtgtctt cccttcaacg   2340
atcgacgttc aacatcgtgt catggctgcc tcagatcccg agattttgg  ttttcgctcc   2400
aattcgtgga ctcaattgtc cttttctac  gatgctacgt tgactgcgac ggattttact   2460
gatgtgaagc attggttgga tctgggaact ggacccgaag cgcgaccgtt gtcttttctg   2520
ccgactgatc ttcctgtcac attgtgcgac actcggcctt tcgttttcc  gtctggctgt   2580
tgggccacgt tcactgactt cttaagttat gattacctcg ttacgaacgt cgttttatca   2640
actggtgccg atgttgtgtc ctgcattctc tccctagggg cagcctgcgc tgacgctaac   2700
atgactctac atgagggcgt gcgtcaacta atttcccagt gcgtagatgc tagtgttaaa   2760
acgctgtttt tgcagcttaa ttgtcccctt ccatcagcgg gtgatgtgtc tcgggagatc   2820
ctcgagttgg ttcagactaa ttcaacatac gtattccata ccttaggtcg cattgagccg   2880
ttcatcccat attccgctct cttggaaata gtcgaggatt tgtgccctgg catcgtcgtt   2940
gagattaaaa cgatggattc ttctctttca tggcttgact acgctgttca atctaatgca   3000
tcagtgacgt cggacgacat tgtcttagcg atgcgtttgt ctcacttctg tcctcttttt   3060
gtgtttcatt ttgaccgtca ttctgctcaa ttcccggaag atgcgcgtgt tggtgctccc   3120
ttcaccgtca cactgttgga ttatgaagat actcgatcat atgaggtgac tttagacaat   3180
gtcactattg ctactattac tgcaggcgct ctggtcggat tttcatctgg tgtaagtgtc   3240
acctcatcca acaatcagct ggttatgact attgatcctg cgagtccagg aattctttct   3300
gtcattcagg tactccccgc tcgcatctca ttaggcagct gcgtgataga ggcgccggac   3360
```

```
ccatcccttt ctctgatttt tcctgctaca ttagatactt ccttgtcagg gaccgacctg    3420
gagttacgtc tgtctgactg gtatgacgtc gctctcttct acgtcgacga agcgcactct    3480
cgactgctgc ccgtatccga taccaagtac gagatttatc gtaaggatca agcgccgaat    3540
agtcgagtaa tcaactatat ctttgatcgt tctgacgtgt tctttaaatt ggtgctgtgc    3600
gacgtctctc catctggaat aggtcgcttc atctatcgtg agttaccgga gctaagttcc    3660
cctgtatggc ctgatgatgc gcgtactttc ttatccatac catttgaatc ccctatggtg    3720
attgtatcgc cggacggacc cgttaactat gacggtgcca atttcactcc tccaacttca    3780
tggcttacag ttgacggcag cacctgcgtc atagatggcc gtccctcatt ttacgtgccc    3840
cctggccgat atggtctggt gagagtctaa acgaccgcgg gcctccagta aaagggtgtt    3900
attcatc                                                              3907

<210> SEQ ID NO 24
<211> LENGTH: 2283
<212> TYPE: DNA
<213> ORGANISM: Artificial Sequence
<220> FEATURE:
<223> OTHER INFORMATION: Synthetic Sequence

<400> SEQUENCE: 24
gcttttctcg acatggcctc tctagccaca cctgtgctag gagtcggttc tcgtattacc      60
gccttagatc gtactattga tgccatcacg ttgaaacctc gaatcgacct ccaagatgtg     120
tacacaattg atcctacact gactctgcgc cagatagagt taatctcttc gggcacttca     180
atggacgaca ttgctcgtgg attgttgcat cgggactggc gtcgtcaatc taccatcatc     240
ttgcttcctt ctcgtcgttc tcttcttgag tacctattgt caaatccttc tgtctgtcca     300
gacggtttag atcgttctcg acttaaagga ttccaaaagc gtccaaacga ttttcgtgtt     360
caagacttct tttctccact gattacggat tcaacgtcaa ttgctacata ttctcggtgg     420
cttaatgctc atcctattgt gtactctact acttacaagg tcgctggcgc tcgggtgcgt     480
ctctttggac ctgccaaatt gtacattctg tcgcctgatg ttcttcgtga attatccatt     540
ttgaaatcca ctgatcgcat cttcgttgta cctacagcac gtgtatatgt cggttgtttt     600
cctagcgctt ctactagcaa ttgtgtcctt actgcacgcg aacgctggaa tgcccctgac     660
gttcatcccg tcgtaaaagc aatccaatta gcctatgacc atcaatatcg tgtcactgct     720
cgttatctct cagaccctct tatctcagct cttcttcttg ggaaccggtc ggtgaagacg     780
ttgaaggtac agccagtaga agccagagca gcacggtcag ttggcatccg cgttcaagcg     840
atgacacctc ctcgtggtat caacacatca atcatccagg tcgttgatct taagttgcaa     900
tgtcggcatt ccctcattcc caccgaaagg ccattcccac taacgtttat cggcctccca     960
tcctgtttgc ttcaacattt ggatctaaca ttatctgatg attgggtgcc cattcgtgat    1020
catacaggta tgtttgaaat gtggtttatg attcttacgc tcacttgtga caagatcctt    1080
gatggacggg ggaacgctgt ttttctcatt cccagttcta ctaatgcact atcagttaat    1140
tatgtacagc tcacgtcaac tgtatcccca cgtcctcagt cactggcggc taatgcgtcc    1200
gggcggatag attccattgg actgtgtatg cctaaaggtt ctttcaagtc aactatgatt    1260
aaatttctca ctggattgga gatttgtggt acgcgagtaa tgtattcaga cgtcgtgatg    1320
gacagtgatg atgtgggtga tgcttttgga cccacttttg agaccgcact atatgacgca    1380
ctgttggctc ttgatccgcc ctttgacgtt gataagttgg ctagtcccac cgatttagtt    1440
gatcaggagt atgtcgcatc tcacatgtac ccaacatttt tacggcttgt caatgagttg    1500
```

```
ctaacgccta aagcttcaga attatactca gagcgtagtg tggagtttcg gtctcttact    1560
tacgcgcatg ctgactctga atttcttaac gcttgctgga ccgctcgctt gatgcgctgc    1620
ttcatcaact atcacgaaga gcagaatatc ctactccgtc ctggacgcgt tggtggtgtg    1680
ctattccagg tcgcgttgag tcgctgctac aagatgtttg ctacttctac tcctgcttcc    1740
cctctgtcat tgttcctcaa gtcgttgttt gttccttgga ttgaatctgc acctttgtta    1800
gcgagtctga cgccgaacga gtcctctcgt gtgttagcat ggtatattcc ttcctcgtac    1860
tggagtgaca atggctggtg cacttgtgac actcatcgtc acgtcacctt ctctttcatt    1920
cgcggtcttc cagcagacct atcggtgtta gatctgtttg actggtctcg attccgcgcg    1980
actataaacg tagacacgtc tctagtcgag ctaggcgctg acattcgtgc ggttaaggtg    2040
tcggttcatt ggacatccca gaagcccact gtggacgtct tgacaatcg cgcgttttc     2100 actcccttcc agcactacca cttgagtctc cattgtaatt gcgcgcctgg tcgcccttt    2160 ttcgcaaaaa atatgaaact gtatctgtcg acggttggag gcgagcactg acgggccgtg   2220
gggcggtgac acccaggggg ggtatgctgg taaccctggg ttagtcgtct tgagatattc   2280
atc                                                                  2283

<210> SEQ ID NO 25
<211> LENGTH: 2158
<212> TYPE: DNA
<213> ORGANISM: Artificial Sequence
<220> FEATURE:
<223> OTHER INFORMATION: Synthetic Sequence

<400> SEQUENCE: 25 gcttttcag tgccagtctt tctcacaaaa tgggcaacgc aacgtctgtc gtgcagaact      60
ttaacatcca aggtgatggc aatcattttg ccccatccgc tgagactact tcatccgcag   120
taccctcgtt atctctgaat cctggactgt tgaatccagg tggtaaggcg tgggttctga   180
ttgactcatc gctaaatgct tcggatcctt catcattaag attgatgact tcggctgatc   240
tatcgacgct ctctcagtcg gctattggta attctactgg gtttcttccc acctccggta   300
tgtacgccgt gactgctaaa gagacgttaa gtgtaataac tgagcatgca atttcccagt   360
ttgataagtt gcaaatggcc tgtgagttgg accgtgatta cctggatgcc agaggcgttt   420
ctcccgagtc cgtgaatatt cataattaca tcgtctatgt tgattgtttt gtgggtgtgt   480
ccgcgaggca ggccgcgtcg aatttcagac agcacgtgcc cgttatcaca aaatctcgta   540
tgacacaatt catgacatct gctcagaacg tgttacaagt gctcggacct tgggaacgtg   600
acgttcgtga actactcact attcttccca cttctactac cgctggcaag atcacatgcg   660
acatgaggtc tgttgtcact ttcattgatg atcagctttc cgacaccagt ttatgccgta   720
tgtaccctga atgtgctgct gcggcggtgg ccagacgtaa tggtggcatc cgatggaaga   780
cacctgagac cgacgaggct ccttcacttg ctactaatga cattgctgcc tcgaccatgg   840
gtgcacttgc aaataccacg ccgttagctg agaaatcgga ttctggtgag gaatcaatgc   900
gcttggtgaa tgatgttggc gtcgatatcg tttgttcccg ggccccgatt agctcctcgg   960
tctggtcacg tacagttgaa ccgagatcat acaacattag aacacttcgc gtagaagaag  1020
ctctctggtt gcgtgagtgt caggcaacta ctggctttga cgtgcagtac acgctccctg  1080
accaggctac tcataaacat ttctggctcc agaaggggtc agttgtcatt aatctagagc  1140
aaacgggcag catgatgttt gatgtaaaca tagcaggtaa agattacaag aagggcactt  1200
```

```
ttaatcctga taatcgtaaa ctagttcttc tggttatgca gtcgaaaata ccttttgaat    1260
cttggactgt cgcttctcag atcactggta tcgcccaagt ggctgaagtc actgtgcacg    1320
ccgctgatag ctcgactccc aaccaaaaga taattggtga acttcgctg tcgtatctgt     1380 ttgagagaga gacagtgacc acgtccgata ccgaaatcaa tacatacca ctgtgcactt     1440 ggcaacttga cgataaacaa agcaatgacg caaatgtctg gccagatgca tgggatggaa    1500
ttacaacatt gacgccactc acttctggta ccgtaactat taaggggact tcggtggact    1560
ctgtcgtacc gtctgatctc gttggcgctt atactcctga gtccttggcc gctgcactcc    1620
ctaatgatgc tggtttgatc ttggctaaca agcaactaa actggctgac gctatcaaga     1680
aagaggatga ctctgtggtc gatgagtctt ctcccttag cactcctatt caagggtcc      1740 tggccgttca acaacttgac accgtaggga cacgtggagc acgcgcactc caacctcctt    1800
cgattctgaa gcgcattgct tcgcgagctc ttcacatgtt cttgggtgac ccgcgttcca    1860
ttttgaaaca ggcgataccc gtgttgagag accctgacgt atggactggt tttgtccaag    1920
gcgttagaga tggcattcgg actaagtcgt tgtccgctgg ggtgcggtcg gtgtacaaca    1980
acgttaccgc cacgcaatct gtccaaacat ggaagcaggg gttcctgaca aaaatacaga    2040
tgttgttcaa accatcgtga ggtgctaagg cctctctcta cggcgggtcg gtgggcacgt    2100
cgtggtgatg ctgaatgcac ggggaggtga cgctccctgg attggcacgt tattcatc     2158

<210> SEQ ID NO 26
<211> LENGTH: 1996
<212> TYPE: DNA
<213> ORGANISM: Artificial Sequence
<220> FEATURE:
<223> OTHER INFORMATION: Synthetic Sequence

<400> SEQUENCE: 26 gcttttgag tcctagcgtg gatcatggcg tcaaccaagt ggggagacaa gccgatgtcg      60
ctctcaatgt ctcacgatgg atcatctatc cgcagtgctg cctcacaatt cttatcggtt     120
cctctgtctc actcaacgcc tatcccacct caacggaaga ctgtgctgtt gaagttcatg     180
attggtgacg aactggttac cgttcagggt gctctcgctc cgttcgacga atattggtat     240
gacaaccagc ccctgttagc tcaggctgtt gagatgctcg cctctgcaga tcgtttgcgt     300
caatttgagc attatgagaa attcctactc aagaaaggtc accagataac tgagatcatg     360
aacaggttac gtctcttttt tacggatgtt ctcaaagtta gatggaagc tgacgcttta      420 cccgctttag cccaatatct gatggttgga accttggagg ctgttccac cgctgattcc     480 cccgatgcct gcgtcccagt cacctcaaag atcttagcta agcagcagac tattgctaag    540
tctcctggac gtctcgacga ggaagaatat aatgttattc gatcacgttt cctcacgcat    600
gaagtcttcg acttaacgtc cgatttaccc ggagtacaac cgtttatgga catgtactac    660
gccactgtcc cccgtgctga ttctacagga tggtgtgtgt atcgtcgaaa gggtttggtt    720
atctacgctc ctgatgagca attctcggat ctgactatct tctccacacg tcttactgca    780
tcacgtgagc tgcagcttgt ggctggagat gttgtcgtag cctgctttga tctcatggac   840
gtctctgaca ttgctccatc tcatcatgca tcagtcagg aagagcgtac tctcgggacc     900
agtaagtatt cgaatgtgac ggctaatgat catcctctgg tattcttctc acccagtgcg    960
ctccgttggg caattgacca tgcttgtact gactccttgg tttctacccg gaatattcgt    1020
gtctgcgttg gcatcgatcc tctgtaact cgatggaccc gagatggtgt gcaagaggct    1080
gctattctca tggatgacaa gctacccctca gcaggtcgtg cgcgtatggc gttgcgaaca    1140
```

```
ttgcttctcg ctagacggtc tccaatgcca tccttcttac tcggtgcgct aaaacagtca    1200
ggcggtcagt tactggagca ctaccgatgc gatgcagcta atagatatgg atctcccacc    1260
gttccgacct cccatccgcc accatgctca aagtgtcctg agctaaaaga acaaattgcc    1320
aagctctcgt catcgcctat acccaaagtc gattcgtccg ttggtccagc cgtactgctg    1380
tctaaaattg ctgaccttca gcgtgctaat agagaactgt cactgaaact ggttgatgtt    1440
caacctgctc gggaagatca cttgttggct tatctcaatg aacacgtgtg tgtaaatgct    1500
aaagatcatg aaaagggcct gctcgctcgt tgtaacgtat ctggtgattc aatctcctct    1560
atccttggcc agcgcatgaa gaatcgggaa aggtttgaaa ctcgactgcg tcatgaggct    1620
agtgctgagt gggaaccccg tgtggaagcg ttaaaccaag aattggctaa agctcgtgtc    1680
gaacagcagg acatgatgac tcaatcccta cagtacctga acgagcgtga tgaactactc    1740
caggaagtgg atgagcttaa gcgtgagctg actaccctgc gttccgctaa cgtacgattg    1800
aatgctgaca atcatcggat gagtcgtgcg acacgtgtcg gagacgcctt cgtcagtgac    1860
gtcgagccgc taccctctgg catacctggt gaatcgaaac catctatgga agaattggtg    1920
gatgatctgt gagctttgac ctgtgactcg acttctctct gattccatgt acccacggcg    1980
gactcggtta ttcatc                                                    1996
```

<210> SEQ ID NO 27
<211> LENGTH: 1643
<212> TYPE: DNA
<213> ORGANISM: Artificial Sequence
<220> FEATURE:
<223> OTHER INFORMATION: Synthetic Sequence

<400> SEQUENCE: 27

```
gcttttcaa tcccttgttc gtcgatgctg cgtatgcctc ccggttcgtg taacggtgcg      60
actgctgtat ttggtaacgt tcattgtcag gcagctcaaa acacggcagg tggtgatttg    120
caagctacgt catccataat tgcatattgg ccttatctag cggcgggtgg tggcttctta    180
ttaattgtta tcattttcgc tcttctatac tgttgtaagg ctaaggtcaa ggcggacgct    240
gcacgtagtg tcttccatcg tgagctggta gcgttgagtt ctggtaagca caatgcaatg    300
gctccgccat acgacgtttg aagtgcaacg atttaatttc tgtccgctat cacttcgcga    360
acttgctatc ccatcatttta ctgctataac tggggctgac ccatcacagt attttaacat    420
tgagctccca cacactcatc ctctctattc caaattgcct actctgttat ctcaaccttg    480
tagggtccac gtgcggctga ttcgccggtt cgctctctat tcaacattgt caagtatttg    540
tgagtacgat tgtgctctac tattctcccc acacgctatc gttccattgc ctgcatccga    600
tcggcggtct tgtcttatag ttcattggga tggcgggtct caatccatcg cagcgaagag    660
aggtcgtcag cttgatactg tcattgactt cgaacgtgac tataagtcat ggcgatttga    720
cgccgatcta tgaacggctg accaatctag aagcgtctac ggagttatta catcgctcca    780
tttccgatat atccactact gtctcaaata tttctgcaaa tttacaagac atgacccata    840
tcttggatga tgtaactgct aatttagacg gtttgaggac cactgttact gcacttcagg    900
atttcgtctc cattctgtct acaaatgtga ctgacttaac gaacacatcc tctgcgcacg    960
cggcgacact atctttactt caaactacgg ttgacggaaa ctccactgcc atctccaatt   1020
tgaagagtga tgtatcgtcg aacggtttag ctattacaga tctgcaggat cgtgttaaat   1080
cattggagtc tactgcgagt catggtctat cttttttcgcc tccgcttagt gtcgctgacg   1140
```

```
gcgtggtttc attagacatg gaccsctact tctgttctca acgagtttct ttaacatcat    1200
actcggcgga ggctcaacta atgcaatttc ggtggatggc acggggtact aacggatcat    1260
ctgataccat tgacatgacc gttaacgctc actgtcatgg aagacgcact gattatatga    1320
tgtcgtccac gggaaatctc acggtcacta gtaacgtcgt gttattaacc ttcgatttaa    1380
gtgacataac gcatatccca tcagacctag cacgtcttgt tcccagtgcg ggattccaag    1440
ctgcgtcgtt ccctgtggac gtatcattca cccgcgattc tgcgactcat cgtaccaag    1500 cgtatgggt gtactcgagc tcacgtgtct tcacaattac tttcccaacc ggaggtgatg    1560
gtacagcgaa cattcgttcc ttgaccgtgc gtaccggcat cgacacctaa ggtgtggcgc    1620
cgtacgggga ttggttattc atc                                           1643
```

<210> SEQ ID NO 28
<211> LENGTH: 1324
<212> TYPE: DNA
<213> ORGANISM: Artificial Sequence
<220> FEATURE:
<223> OTHER INFORMATION: Synthetic Sequence

<400> SEQUENCE: 28

```
gcttttctc ccacgatggc gcgtgccata tacgacttct tttctacgcc tttcgggaat      60
cgtggtctag cgacgaatcg tactcaactg tcatcactac tatcgagctc gaattcccca    120
tggcaacgat ttctatcatc aatgactcca ttgacagcgc caggtatcgt ttcaacgcct    180
gaagcaccct atccaggttc gttgatgtat caagagtcta tgctccacag tgctactgtc    240
cctggagtac tcggtagtcg tgatgcttgg cgtacattta atgtcttcgg gctttcgtgg    300
actgatgaag gattgtcagg actagtagct gcccaagatc ctcccctgc cgccccgtat    360 cagccagcct ctgctcagtg gtcggatctc ctcaactacc ctagatgggc aaacagacgt    420
cgtgagctgc aatctaaata cccacttctg cttcggtcca cgctgctttc tgccatgcga    480
gctggtcctg ttctctacgt tgagacgtgg ccgaatatga tctcaggacg attagctgat    540
tggttcatgt cccaatatgg caacaatttc gttgacatgt gcgccaggtt gacccagtct    600
tgttcgaaca tgcctgttga gcctgatgga aattatgatc agcagatgcg tgatttaatt    660
agtttgtggc ttctttcata cattggggtg gtcaatcaga ccaacaccat cagcggcttc    720
tacttctcct cgaagactcg gggtcaagcg ttggacagtt ggactttatt ctacactaca    780
aacactaatc gtgttcaaat tacgcagagg catttcgctt acgtgtgtgc tcggtctccc    840
gactggaacg tggataaatc atggatcgct gcagcgaact taaccgctat cgtcatggct    900
tgccgtcaac cgccggtgtt cgccaatcaa ggcgttatta accaagcgca gaaccgacct    960
ggcttttcca tgaatggggg gacgcccgtc catgagctca acttactgac taccgcgcag   1020
gaatgtattc ggcagtgggt gatggccggt ttggtgtcgg cagcgaaggg gcaagcctta   1080
acgcaggagg ctaatgactt ctcgaacctc atccaggcgg atctaggaca aatcaaagcg   1140
caggatgatg ctctgtacaa ccagcagcca gggtacgcga ggagaataaa acccttcgtt   1200
aacggtgact ggacaccagg tatgaccgcg caagctctgg ccgttctagc cacttttacc   1260
gcctaggcgt agggtcgtac gctgcccgag tccagccctc cggcagcacg tggatgtatt   1320
catc                                                                1324
```

<210> SEQ ID NO 29
<211> LENGTH: 1202
<212> TYPE: DNA
<213> ORGANISM: Artificial Sequence
<220> FEATURE:
<223> OTHER INFORMATION: Synthetic Sequence

<400> SEQUENCE: 29

| | | | | | |
|---|---|---|---|---|---|
| gcttttgag | tccttagcgt | gcaagccgca | atggaggtac | gtgtgccaaa | ctttcactcg | 60 |
| ttcgttgaag | gaataacatc | tagctatttg | aagactcctg | cttgctggaa | tgcacagaca | 120 |
| gcctgggaca | ctgtgacttt | tcacgtccct | gatgtaatta | gagttggcaa | tgcgtattgt | 180 |
| tgctctcaat | gttgtggtgt | actttattac | gggactctgc | ccgcggatgg | aaattacttc | 240 |
| cctcatcaca | aatgccatca | gcaacagtac | aggaccgata | ccccactgct | ccggtatgtg | 300 |
| cgaattggca | gaacgactga | gcatctgttg | gaccaatatg | ctgttgcgct | ggagtctatt | 360 |
| gctgatcact | atgatgaaat | cagtcaacgc | atggtcgatg | agccagagaa | cgatgaagtc | 420 |
| gcgccccttg | acattgtaac | gcgtactgaa | tctatccgaa | gtgataagac | ggttgacccg | 480 |
| gacttttgga | cttacccgct | tgagcgacgt | tctgatgatt | ctcgtcgaga | catcgccgca | 540 |
| tcatgctgga | gaatgattga | tgcatcatca | cgtagtctca | ctcttccaaa | ttgtcttgtg | 600 |
| tccccgtctt | tgcattctcg | ttccgtctttt | ggtcaaatgc | aaacgaccac | caccatatac | 660 |
| gatgttgcgg | cgtcgggaaa | ggccgttaaa | ttttctccga | tggtggctac | actatcgcaa | 720 |
| cgtgatgctg | gccctgtaaa | gcttgcgaat | gctgacccag | cggaaggtgt | atattcattt | 780 |
| tggacgtcgc | acttcgcctt | ctcaccgctc | attggtggag | ttgggattac | gggacagtac | 840 |
| gctcgtgagt | cataccatca | cgtgggtcat | ccagtgattg | ggagtggtaa | gaaggcatca | 900 |
| cactacagaa | atctgtttat | ggaatcatgg | cgtgggtggt | caaagtcagc | tttcgcatgc | 960 |
| gctacaggaa | tggagccagc | tgaatgtgaa | tctcgtctga | ggggacatgc | tcgcactatg | 1020 |
| cttggacgct | ctctgccgaa | cgtctgtgac | gacgaggttg | ctcagcagtc | tggcgccgtg | 1080 |
| ctaacgtccc | tgcagaagac | taccaagttc | actgttgtgg | agtgtggttg | gtaagtacct | 1140 |
| ccgggtcaaa | atgcacatag | gctcccacct | atgtgacggt | tagcgggact | cgcctattca | 1200 |
| tc | | | | | | 1202 |

<210> SEQ ID NO 30
<211> LENGTH: 1192
<212> TYPE: DNA
<213> ORGANISM: Artificial Sequence
<220> FEATURE:
<223> OTHER INFORMATION: Synthetic Sequence

<400> SEQUENCE: 30

| | | | | | |
|---|---|---|---|---|---|
| gcttttgag | tccttgtgca | gccatggaca | acaccgtgcg | tgttggagtt | tcccgcaaca | 60 |
| catccggcgc | agctggtcag | acactctta | gaaacttcta | tttactacga | tgtaatattt | 120 |
| cagctgatgg | ccgtaatgca | acgaaggcgg | tacaatccca | ctttccattc | ctttcacgtg | 180 |
| ctgtgcgatg | cctatcgcct | cttgccgctc | actgtgctga | tagaacccttt | cgccgtgaca | 240 |
| acgtgaaaca | gattcttact | cgtgaactgc | cattttcctc | ggatctaatc | aactacgcac | 300 |
| accatgtcaa | ttcatcatcc | cttactacct | ctcaaggcgt | cgaagcggct | cgtttggtag | 360 |
| ctcaagtta | tggggaacaa | gtaccgttcg | atcacattta | tcctactggt | tcagcgacat | 420 |
| actgtcctgg | tgcaatcgca | aatgctattt | ctcgcattat | ggctggcttt | gtacctcgtg | 480 |
| aaggtgatga | ctttgctccg | agtggcccta | ttgactacct | cgctgctgac | ctgatcgcgt | 540 |
| ataagtttgt | gctcccttac | atgcttgaca | tggtagatgg | tcgtcctcag | attgtcctgc | 600 |
| cgtctcatac | cgtagaagaa | atgttgacca | acaccagctt | gctgaactcg | attgatgctt | 660 |

-continued

```
catttggtat cgaagcgcgc agtgatcaaa ggatgactcg tgatgctgct gagatgagtt    720
ctcgctccct caatgaactt gaggatcatg atcagagagg tcgtatgcct tggaagatca    780
tgctagcgat gatggcggcc caattgaagg ttgagttgga cgcgctggcg gacgagcgta    840
cggagtcaca agctaatgct cacgttacat ccttcggatc ccgtttattt aatcagatgt    900
cggcgttcgt tactattgat cgtgaactga tggaactggc ccttctcatc aaggaacagg    960
gcttcgccat gaatccgggt cagattgcat ctaagtggtc gctgatacgt cgttccggtc   1020
ctactcgtcc actttcaggt gcccgtcttg aaatcaggaa tggtaattgg atgatccgtg   1080
agggtgacca aacgctactg tctgtctctc cagctaggat ggcgtagacg ggacccatgg   1140
tgcgggtgag gggtcgccac accctctgcc gcgacttgga ctcttattca tc           1192
```